US012668631B2

(12) United States Patent (10) Patent No.: US 12,668,631 B2
He et al. (45) Date of Patent: Jun. 30, 2026

(54) CD3-TARGETING ANTIBODY, BISPECIFIC ANTIBODY AND USE THEREOF

(71) Applicant: HARBOUR BIOMED (SHANGHAI) CO., LTD., Shanghai (CN)

(72) Inventors: Yun He, Suzhou (CN); Lei Shi, Suzhou (CN)

(73) Assignee: HARBOUR BIOMED (SHANGHAI) CO., LTD, Shanghai (CN)

( * ) Notice: Subject to any disclaimer, the term of this patent is extended or adjusted under 35 U.S.C. 154(b) by 1016 days.

(21) Appl. No.: 17/764,284

(22) PCT Filed: Sep. 29, 2020

(86) PCT No.: PCT/CN2020/118606
§ 371 (c)(1),
(2) Date: Mar. 28, 2022

(87) PCT Pub. No.: WO2021/063330
PCT Pub. Date: Apr. 8, 2021

(65) Prior Publication Data
US 2022/0348661 A1 Nov. 3, 2022

(30) Foreign Application Priority Data
Sep. 30, 2019 (CN) .......................... 201910941328.6

(51) Int. Cl.
*C07K 16/28* (2006.01)
*A61P 35/00* (2006.01)

(52) U.S. Cl.
CPC .......... *C07K 16/2809* (2013.01); *A61P 35/00* (2018.01); *C07K 16/2803* (2013.01); *C07K 16/2827* (2013.01); *C07K 2317/24* (2013.01); *C07K 2317/31* (2013.01); *C07K 2317/56* (2013.01); *C07K 2317/622* (2013.01)

(58) Field of Classification Search
CPC ............ C07K 16/2809; C07K 16/2803; C07K 16/2827; C07K 2317/24; C07K 2317/31; C07K 2317/56; C07K 2317/622; C07K 2317/52; C07K 2317/64; C07K 2317/70; C07K 2317/71; C07K 2317/73; C07K 2319/00; C07K 2319/21; A61P 35/00; A61K 2039/505
See application file for complete search history.

(56) References Cited

U.S. PATENT DOCUMENTS

| | | | |
|---|---|---|---|
| 6,750,325 B1 | 6/2004 | Jolliffe et al. | |
| 7,112,324 B1 | 9/2006 | Dorken et al. | |
| 8,846,042 B2 | 9/2014 | Zhou | |
| 9,777,073 B2 * | 10/2017 | Zhou ................. | C07K 16/2878 |
| 10,059,768 B2 | 8/2018 | Leong et al. | |
| 10,738,118 B2 | 8/2020 | Evnin et al. | |
| 10,870,701 B2 | 12/2020 | Cui et al. | |
| 10,889,653 B2 | 1/2021 | Bernett et al. | |
| 2016/0326249 A1 | 11/2016 | Ng et al. | |

FOREIGN PATENT DOCUMENTS

| | | |
|---|---|---|
| CN | 103842383 A | 6/2014 |
| CN | 106804108 A | 6/2017 |
| CN | 107207610 A | 9/2017 |
| CN | 108289949 A | 7/2018 |
| CN | 109476756 A | 3/2019 |
| EP | 3492591 A1 | 6/2019 |
| RU | 2228202 C2 | 5/2004 |
| RU | 2016132863 A | 2/2018 |
| WO | WO-2015001085 A1 | 1/2015 |
| WO | WO-2016040724 A1 | 3/2016 |
| WO | WO-2016071004 A1 | 5/2016 |
| WO | WO-2016071355 A1 | 5/2016 |
| WO | WO-2016094873 A2 | 6/2016 |
| WO | WO-2017136659 A2 | 8/2017 |
| WO | WO-2019008379 A1 | 1/2019 |
| WO | WO-2019075405 A1 | 4/2019 |

OTHER PUBLICATIONS

Baeuerle and Reinhardt Cancer Res 2009; 69: (12), 4941-4944 (Year: 2009).*
Apr. 18, 2024 First Office Action issued in Australian Patent Application No. AU2020359928.
Jun. 27, 2024 Second Office Action issued in European Patent Application No. EP20872856.8.
Dec. 9, 2024 Request for the Submission of an Opinion issued in Korean Application No. 10-2022-7014723.
Nov. 11, 2024 Second Office Action issued in Canada Patent Application No. 3,152,438.
Mar. 11, 2025 First Office Action issued in Japanese Patent Application No. 2024-000181.
Dec. 31, 2020 International Search Report issued in International Patent Application No. PCT/CN2020/118606.
Dec. 31, 2020 Written Opinion of the International Searching Authority issued in International Patent Application No. PCT/CN2020/118606.

(Continued)

*Primary Examiner* — Misook Yu
*Assistant Examiner* — Grace H Lunde
(74) *Attorney, Agent, or Firm* — Harness, Dickey & Pierce, P.L.C.

(57) ABSTRACT

Disclosed are a CD3-targeting antibody, a bispecific antibody and the use thereof. The CD3-targeting antibody comprises a light chain variable region (VL) and a heavy chain variable region (VH). The VL has the amino acid sequence as shown in SEQ ID NO: 56 or a mutation thereof. The VH has mutations on the amino acid sequence as shown in SEQ ID NO: 42, and the mutations occur at one or more of the sites of amino acid residues selected from positions 30, 73, 76, 78, 93 and 94. The bispecific antibody comprises a first protein functional region and a second protein functional region, wherein the first protein functional region comprises the CD3-targeting antibody as described above. The CD3-targeting antibody reduces the toxicity caused by cytokine release syndrome, and the bispecific antibody prepared therefrom is stable and has the ability to bind to T cells, and also reduces the difficulty of producing.

18 Claims, 18 Drawing Sheets

Specification includes a Sequence Listing.

(56) References Cited

OTHER PUBLICATIONS

Oct. 8, 2021 Chinese First Office Action issued in Chinese Patent Application No. 2020800061738.
Jan. 5, 2022 Taiwan First Office Action issued in Patent Application No. 109133808.
Salmeron, A. et al, J Immunol 147 (1991) 3047-3052.
Conrad M.L., et al, Cytometry A 71 (2007) 925-933.
Al-Lazikani et al, JMol Biol 273:927-48, 1997.
Schlothauer T, Herter S, Koller CF, et al. Protein Eng Des Sel. Oct. 2016;29(10):457-466.
Jun. 8, 2023 First Office Action issued in Canada Patent Application No. 3,152,438.
Aug. 2, 2021 Notice of Reasons for Refusal issued in Taiwan Patent Application No. 109133808.
Japanese Notice of Reasons for Refusal in Japanese Patent Application No. 2022-520343 dated Mar. 8, 2023.
Russia 2nd Office Action in Russia Patent Application No. 2022110535 dated Apr. 28, 2023.
Oct. 25, 2022 Notice of First Office Action issued in European Patent Application No. 20872856.8.
Dec. 2, 2022 Notice of First Office Action issued in Russian Patent Application No. 2022110535.
Sep. 4, 2023 Decision of Refusal issued in Japanese Patent Application No. 2022-520343.
Jan. 30, 2026 Third Office Action issued in European Patent Application No. 20872856.8.

* cited by examiner

(A)

(B)

(A)

(B)

(A)

(B)

(A)

(B)

(A)

(B)

(A)

(B)

(A)    CD3 monoclonal antibody    TAA monoclonal antibody

(B)     TAA × CD3 bispecific antibody

(C)     TAA × CD3 bispecific antibody

CD3-TARGETING ANTIBODY, BISPECIFIC ANTIBODY AND USE THEREOF

REFERENCE TO SEQUENCE LISTING

The Sequence Listing is submitted concurrently with the specification as an ASCII formatted text file via EFS-Web, with a file name of "17424-113-NP English Translation of Sequence Listing.TXT", a creation date of Mar. 24, 2022, and a size of 121,432 bytes. The Sequence Listing filed via EFS-Web is part of the specification and is incorporated in its entirety by reference herein.

This application is a National Stage of International Application No. PCT/CN2020/118606, filed on Sep. 29, 2020, which claims the priority of Chinese patent application 2019109413286 filed on Sep. 30, 2019, the contents of which are incorporated herein by its entirety.

TECHNICAL FIELD

The present invention belongs to the field of biopharmaceuticals, in particular to a CD3-targeting antibody, bispecific antibody and use thereof.

BACKGROUND

T-lymphocytes are an important class of cells involved in the adaptive immune response, and T cells recognize antigens through the T cell receptor (TCR). The TCR does not recognize antigen surface epitopes directly, but specifically recognizes antigen-peptide-MHC molecular complexes (pMHC) presented on the surface of antigen-presenting cells (APCs) or target cells. The specificity of the T cell response is mediated by the recognition of pMHC by molecular complexes of the TCR and CD3. TCR is a heterodimer composed of two different transmembrane polypeptide chains with four peptide chains including α, β, γ and δ; according to the different combinations of peptide chains, TCR is divided into TCRαβ and TCRγδ. CD3 has different transmembrane polypeptide chains, i.e., γ, δ, ε, and ζ, which interact to form homodimers or heterodimers as part of the TCR-CD3 complexes. For example, the TCR-CD3 complexes include TCRαβ dimer, CD3γε dimer, CD3δε dimer, and CD3ζζ dimer. Since the cytoplasmic region of the TCR peptide chain is very short, it is generally assumed that the activation signal generated by antigen recognition by the TCR is transduced into the T cell by the CD3 peptide chain.

Due to the important role of CD3 in initiating the immune response, the signal transduction targeting TCR-CD3 signaling, particularly monoclonal antibodies targeting CD3, are considered to be effective agents that can modulate the immune process and be used to treat inflammatory or autoimmune diseases. In fact, the anti-CD3 antibody Orthoclone OKT3 was the first approved therapeutic antibody. OKT3 was first approved by the US FDA in 1985 for the treatment of acute rejection after organ transplantation. Although the immunosuppressive capacity resulting from repeated administration of OKT3 provided an effective treatment for rejection after kidney transplantation, its application was limited by the first toxic dose response syndrome; the syndrome thought to be associated with OKT3-mediated T cell activation and cytokine release. Subsequently, OKT3 was withdrawn from the market in 2010 due to severe cytokine storm and immunogenicity problems associated with murine antibodies, among other factors.

Another problem with CD3 antibodies is that many CD3 antibodies have been found to be species-specific, for example, OKT3 reacts with CD3 of chimpanzee but not with CD3 of other primates, such as macaque CD3 homologs, or murine CD3 homologs. The species specificity of CD3 monoclonal antibodies is a significant barrier to their development as antibody drugs for the treatment of human diseases. Any new candidate drug must undergo rigorous preclinical validation before it can be used in clinical trials in human patients. The purpose of preclinical testing is to confirm that the candidate drug has the desired activity and, most importantly, that the candidate drug is safe. Preclinical safety testing involves the administration of the candidate drug to the species of interest, preferably Non-Human Primates. However, higher primates, particularly chimpanzees, are considered endangered species and the use of such animals for drug safety testing is highly restricted. The species described in the art suitable for safety evaluation testing may be macaques, in particular cynomolgus monkeys. However, it is difficult to provide valid preclinical safety evaluation data of CD3 antibodies that lack primate species-specific cross-reactivity. Among the known antibodies that bind to human CD3, SP34 is one of the very few that can bind to multiple primate CD3s (e.g., human and cynomolgus monkey CD3) (See, Salmeron, A. et al, J Immunol 147 (1991) 3047-3052; Conrad M. L., et. al, Cytometry A71 (2007) 925-933).

Although monoclonal antibodies of CD3 have been clinically validated for their effectiveness in certain diseases, however, in recent years, CD3 antibodies have been more often used in the development of bispecific antibody drugs. Currently, CD3-based Bi-specific T cell engager antibodies (BsTCE) account for more than half of the bispecific antibody programs in the clinical or preclinical stage worldwide. The CD3 bispecific antibodies BsTCE, on the one hand, show the same strong efficacy as CAR-T cell therapy, and on the other hand, they can be produced and commercialized like traditional monoclonal antibodies. Among the bispecific antibodies currently approved for marketing worldwide, the earliest Catumaxomab (approved by Europe EMA in 2009, and withdrawn from the US in 2013) and Blinatumomab (approved by FDA in 2014) are both BsTCEs. CD3 antibody is an important component in the construction of BsTCE. BsTCE bispecific antibody can bind to two targets at the same time, one end recognizes Tumor-associated antigen (TAA) on the surface of tumor cells, while the other end binds to the CD3 molecule on T cells. In the presence of tumor cells, the binding of BsTCE bispecific antibody to the surface of tumor cells can recruit and activate T cells near the tumor cells, which in turn kills the tumor cells. When designing and constructing various structures of BsTCE bispecific antibodies, the selection and optimization of CD3 antibodies is of paramount importance. First, the species specificity of CD3 monoclonal antibodies is very important, especially monkey cross-reaction. Second, the affinity of the CD3 antibody to the CD3 complex is also very important; CD3 antibody with high affinity may confine the antibody to the spleen and other areas, making it difficult to contact with the tumor; and high affinity may also over stimulate T cells, resulting in high level of cytokine release. Third, CD3 antibody binding valence bonds also play an important role, it was previously found that multivalent forms of CD3 bispecific antibodies may cause side effects by activating T cells without binding tumor-associated antigens, and thus the vast majority of CD3 bispecific antibodies under investigation are in the form of monovalent CD3.

In addition to CD3 antibodies, the structural design of BsTCE bispecific antibodies is also very important. There are various structures of BsTCE bispecific antibodies, which can be divided into two main categories: IgG-like structures containing Fc and antibody fragment structures without Fc. For example, Blinatumomab is a single polypeptide chain structure consisting of two single-chain variable region antibody fragments (scFv) in series, but this structure has a short half-life, requireing continuous intravenous perfusion, and is very inconvenient to use. Fc-containing structures are used in many BsTCE bispecific antibodies therefore to improve molecular stability and pharmacokinetic properties. However, since the CD3-binding domain in BsTCE usually requires a monovalent form, Fc-containing structures are often asymmetric. There are many technical difficulties to be overcome in these asymmetric structures containing Fc, such as the heavy chain homodimerization problem in the asymmetric structure, the light chain mismatch problem, the molecular cross-linking caused by Fcγ receptor and the functional effects such as ADCC or CDC, etc. Different asymmetric structures can be chosen for the construction of BsTCE bispecific antibodies from anti-TAA IgG antibodies and anti-CD3 IgG antibodies [FIG. 16 (A)], one of the commonly used structures is an IgG-like structure that retains two independent Fab domains, which contains four different polypeptide chains [two different heavy chains and two different light chains, structure shown in FIG. 16 (B)], with an approximate molecular weight to that of a conventional monoclonal antibody; this structure may bring about by-products containing multiple combinations due to containing many different polypeptide chains, which poses a great challenge to the expression purification and production process of the antibody. If the Fab of the CD3 antibody is modified into a scFv structure, the "four-chain" structure can be changed into a "three-chain" structure [shown in FIG. 16 (C)], further reducing the number of by-product combinations and thus the complexity of its production. In order to construct BsTCE bispecific antibody, the present inventors tried to convert SP34 mouse anti-IgG into scFv, but no matter which (VH/VL) arrangement mode was adopted or the length of the linking peptide was changed, no stable scFv could be obtained, so a stable anti-CD3 monoclonal antibody, especially its stable scFv structure, is urgently needed in the art.

In summary, there is an urgent need in the art for a CD3 antibody that is capable of binding to primate CD3, has a suitable CD3 binding capacity, and has a stable single-chain scFv structure.

Content of the Present Invention

The technical problem to be solved in the art is to overcome the defect of lacking low-antigenic, effective and safe anti-CD3 antibodies and bispecific antibodies with asymmetric structures, the present invention provides a CD3-targeting antibody, bispecific antibody and use thereof.

To solve the above-mentioned technical problem, the technical solution provided by the first aspect of the present invention is: a CD3-targeting antibody, comprising a light chain variable region (VL) and a heavy chain variable region (VH); wherein the amino acid sequence of the VL is set forth in SEQ ID NO: 56 or a mutant thereof, the VH is a mutant of the amino acid sequence set forth in SEQ ID NO: 42 comprising one or more mutations at positions 30, 73, 76, 78, 93 and 94 (according to Chothia numbering scheme). The mutation can cause addition, deletion or substitution of one or more amino acid residues in the original amino acid sequence. The CD3-targeting antibody of the present invention alters the binding capacity to T cells and reduces the level of cytokine release, and thus is expected to reduce the toxicity associated with cytokine release syndrome.

In a preferred example, the VH has mutations at positions selected from the following groups:
(a) position 30;
(b) positions 30, 73 and 76;
(c) positions 30, 93 and 94;
(d) positions 30, 73 and 93;
(e) positions 30 and 93;
(f) positions 30, 76 and 78;
(g) positions 73, 76, 93 and 94;
(h) positions 76, 78 and 93;
(I) positions 30, 73, 76, 93 and 94;
(j) positions 30, 76, 78 and 93.

In a preferred example, the VH has mutations selected from the following groups:
(a) N30S;
(b) N30S, D73N and S76N;
(c) N30S, V93A, and R94K;
(d) N30S, D73N, and V93A;
(e) N30S and V93T;
(f) N30S, S76N and L78A;
(g) D73N, S76N, V93A, and R94K;
(h) S76N, L78A, and V93T;
(i) N30S, D73N, S76N, V93A, and R94K;
(j) N30S, S76N, L78A, and V93T.

Provided that the VH of the antibody has the above-defined mutations, the antibody of the present invention is further mutated on the amino acid sequence of the VL set forth in SEQ ID NO: 56, or on the amino acid sequence of the VH set forth in SEQ ID NO: 42, and the resulted amino acid sequence has 80%, 85%, 90%, 95%, 98%, 99% or more identity with the original amino acid sequence, and the amino acid sequences that maintain or improve the function of the antibody are also within the scope of protection of the present invention.

In a preferred example, the amino acid sequence of the VH is set forth in any one of SEQ ID NOs: 43-55, and/or, the amino acid sequence of the VL is set forth in any one of SEQ ID NOs: 57-60.

In a preferred example,
the amino acid sequence of the VH is set forth in SEQ ID NO: 44, and the amino acid sequence of the VL is set forth in SEQ ID NO: 58; or,
the amino acid sequence of the VH is set forth in SEQ ID NO: 51, and the amino acid sequence of the VL is set forth in SEQ ID NO: 58; or,
the amino acid sequence of the VH is set forth in SEQ ID NO: 44, and the amino acid sequence of the VL is set forth in SEQ ID NO: 60; or,
the amino acid sequence of the VH is set forth in SEQ ID NO: 51, and the amino acid sequence of the VL is set forth in SEQ ID NO: 60; or,
the amino acid sequence of the VH is set forth in SEQ ID NO: 45, and the amino acid sequence of the VL is set forth in SEQ ID NO: 58; or,
the amino acid sequence of the VH is set forth in SEQ ID NO: 52, and the amino acid sequence of the VL is set forth in SEQ ID NO: 58; or,
the amino acid sequence of the VH is set forth in SEQ ID NO: 43, and the amino acid sequence of the VL is set forth in SEQ ID NO: 58; or,
the amino acid sequence of the VH is set forth in SEQ ID NO: 43, and the amino acid sequence of the VL is set forth in SEQ ID NO: 60; or,
the amino acid sequence of the VH is set forth in SEQ ID NO: 50, and the amino acid sequence of the VL is set forth in SEQ ID NO: 58; or, the amino acid sequence of the VH is set forth in SEQ ID NO: 47, and the amino acid sequence of the VL is set forth in SEQ ID NO: 58; or, the amino acid sequence of the VH is set forth in SEQ ID NO: 48, and the amino acid sequence of the VL is set forth in SEQ ID NO: 58; or, the amino acid sequence of the VH is set forth in SEQ ID NO: 49, and the amino acid sequence of the VL is set forth in SEQ ID NO: 58; or, the amino acid sequence of the VH is set forth in SEQ ID NO: 53, and the amino acid sequence of the VL is set forth in SEQ ID NO: 58; or, the amino acid sequence of the VH is set forth in SEQ ID NO: 54, and the amino acid sequence of the VL is set forth in SEQ ID NO: 58; or, the amino acid sequence of the VH is set forth in SEQ ID NO: 43, and the amino acid sequence of the VL is set forth in SEQ ID NO: 57; or, the amino acid sequence of the VH is set forth in SEQ ID NO: 44, and the amino acid sequence of the VL is set forth in SEQ ID NO: 57; or, the amino acid sequence of the VH is set forth in SEQ ID NO: 43, and the amino acid sequence of the VL is set forth in SEQ ID NO: 59; or, the amino acid sequence of the VH is set forth in SEQ ID NO: 44, and the amino acid sequence of the VL is set forth in SEQ ID NO: 59; or, the amino acid sequence of the VH is set forth in SEQ ID NO: 51, and the amino acid sequence of the VL is set forth in SEQ ID NO: 57; or, the amino acid sequence of the VH is set forth in SEQ ID NO: 55, and the amino acid sequence of the VL is set forth in SEQ ID NO: 58; or, the amino acid sequence of the VH is set forth in SEQ ID NO: 46 and the amino acid sequence of the VL is set forth in SEQ ID NO: 58.

In a preferred example, the antibody comprises a single chain variable antibody (scFv) of VL-Linker-VH or VH-Linker-VL; preferably, the Linker (i.e., linker peptide) is $(GGGGS)_n$ [abbreviation $(G_4S)_n$] or a variant thereof, wherein n is a non-zero natural number, preferably 1 to 20, more preferably the amino acid sequence of the Linker is set forth in SEQ ID NO: 65, SEQ ID NO: 66, or SEQ ID NO: 67; more preferably, the amino acid sequence of the scFv is set forth in SEQ ID NO: 73, SEQ ID NO: 74, SEQ ID NO: 75, SEQ ID NO: 78, SEQ ID NO: 79 or SEQ ID NO: 80; further preferably, the antibody further comprises fragment crystallizable (Fc), the Fc linked to the scFv by a Hinge.

In a preferred example, the antibody further comprises a constant region, preferably a human constant region; preferably, the human constant region comprises a human light chain constant region and a human heavy chain constant region, and the human light chain constant region is preferably a human κ light chain constant region as shown in SEQ ID NO: 61 or a human λ light chain constant region as shown in SEQ ID NO: 62; more preferably, the human heavy chain constant region is hIgG1, hIgG2, hIgG3, hIgG4, or a variant thereof, preferably a heavy chain constant region as shown in SEQ ID NO: 63 or SEQ ID NO: 64.

To solve the above-mentioned technical problem, the technical solution provided by the second aspect of the present invention is: a bispecific antibody. The bispecific antibody of the present invention has a three-chain structure, which can reduce the number of by-product combinations and thus the complexity of its production; but it is not possible to develop the bispecific antibody by slightly modifying the antibody of the existing technology. As described in the background, in order to construct BsTCE bispecific antibody, the present inventors tried to convert SP34 mouse anti-IgG into scFv, but no matter which (VH/VL) arrangement mode was adopted or the length of the linker peptide was changed, no stable scFv could be obtained. After several mutation designs and validations, the inventors found that only some of these mutations could keep the scFv in a stable structure. The bispecific antibody of the present invention comprising a first protein functional region and a second protein functional region, wherein the first protein functional region comprises the CD3-targeting antibody of the first aspect of the present invention; preferably, the bispecific antibody comprises the following three chains: (1) VL1-Linker-VH1-Hinge-CH2-CH3 (knob) or VH1-Linker-VL1-Hinge-CH2-CH3 (knob) of the first protein functional region, (2) VH2-CH1-Hinge-CH2-CH3 (hole) of the second protein functional region, and (3) VL2-CL of the second protein functional region; the second protein functional region is a non-CD3-targeting antibody, preferably a B7H4-targeting antibody or a ROR1-targeting antibody, and the linker is preferably $(G_4S)_n$, wherein n is a non-zero natural number, preferably 1 to 20, and more preferably the amino acid sequence of the Linker is set forth in SEQ ID NO: 65, SEQ ID NO: 66, or SEQ ID NO: 67; more preferably, the bispecific antibody comprises VL1-Linker-VH1-Hinge-CH2-CH3 (knob) as shown in SEQ ID NO: 88, VH2-CH1-Hinge-CH2-CH3 (hole) as shown in SEQ ID NO: 86, and VL2-CL as shown in SEQ ID NO: 83, or, VL1-Linker-VH1-Hinge-CH2-CH3 (knob) as shown in SEQ ID NO: 88, VH2-CH1-Hinge-CH2-CH3 (hole) as shown in SEQ ID NO: 87, and VL2-CL as shown in SEQ ID NO: 85. The bispecific antibody of the present invention overcome the defect of instability of the CD3-targeting single chain antibody arm, which is stable and has the ability to bind to T cells. The bispecific antibody containing only three chains is easily to be prepared, the production difficulty of which is reduced.

To solve the above-mentioned technical problem, the technical solution provided by the third aspect of the present invention is: an isolated nucleic acid, encoding the CD3-targeting antibody of the first aspect of the present invention or the bispecific antibody of the second aspect of the present invention.

To solve the above-mentioned technical problem, the technical solution provided by the forth aspect of the present invention is: an expression vector, comprising the isolated nucleic acid of the third aspect of the present invention; preferably, the expression vector is selected from a retroviral vector, a lentiviral vector, an adenovirus vector, and an adeno-associated virus vector.

To solve the above-mentioned technical problem, the technical solution provided by the fifth aspect of the present invention is: a genetically modified cell, transfected with the expression vector of the forth aspect of the present invention; preferably, the genetically modified cell is a eukaryotic cell.

To solve the above-mentioned technical problem, the technical solution provided by the sixth aspect of the present invention is: a pharmaceutical composition, comprising the CD3-targeting antibody of the first aspect of the present invention, the bispecific antibody of the second aspect of the present invention, the genetically modified cell of the fifth aspect of the present invention, and a pharmaceutically acceptable carrier; preferably, the pharmaceutical composition further comprises an immune checkpoint antibody.

To solve the above-mentioned technical problem, the technical solution provided by the seventh aspect of the present invention is: a use of the CD3-targeting antibody of the first aspect of the present invention, the bispecific antibody of the second aspect of the present invention, the isolated nucleic acid of the third aspect of the present invention, the expression vector of the forth aspect of the present invention, the genetically modified cell of the fifth aspect of the present invention or the pharmaceutical composition of the sixth aspect of the present invention in the manufacture of a medicament for the treatment of tumor.

To solve the above-mentioned technical problem, the technical solution provided by the eighth aspect of the present invention is: a kit combination, comprising a kit A and a kit B; the kit A comprises the CD3-targeting antibody of the first aspect of the present invention, the bispecific antibody of the second aspect of the present invention, the genetically modified cell of the fifth aspect of the present invention or the pharmaceutical composition of the sixth aspect of the present invention; the kit B comprises other antibodies, bispecific antibodies, genetically modified cells or pharmaceutical compositions, the other antibodies, bispecific antibodies, genetically modified cells or pharmaceutical compositions targeting CD3, B7H4, ROR1 or other targets. The kit A and kit B can be used in any order, kit A can be used before kit B, or kit B can be used before kit A. The drug in kit A is present in an injectable form such as an injection, and the drug in kit B is present in an injectable form such as an injection, or in a swallowable form such as a tablet or pill.

The CD3-targeting antibody of the first aspect of the present invention, the bispecific antibody of the second aspect of the present invention, the genetically modified cell of the fifth aspect of the present invention, the pharmaceutical composition of the sixth aspect of the present invention or the kit combination of the eighth aspect of the present invention may be administered to a patient for the treatment of the relevant tumor.

On the basis of common sense in the art, the above-mentioned preferred conditions can be combined arbitrarily to obtain preferred examples of the present invention.

The reagents and raw materials used in the present invention are all commercially available.

The positive and progressive effects of the present invention are:

1. The monoclonal antibody of the present invention alters the binding capacity to T cells and reduces the level of cytokine release, and thus is expected to reduce the toxicity associated with cytokine release syndrome.
2. The bispecific antibody prepared from it overcome the defect of instability of the CD3-targeting single chain antibody arm, which is stable and has the ability to bind to T cells.
3. The bispecific antibody containing only three chains is easily to be prepared, the production difficulty of which is reduced.

BRIEF DESCRIPTION OF THE DRAWINGS

FIG. 7B: PR001848, PR001849 and PR000260 bind to human T cells, FIG. 7C: PR002467, PR002468, PR002469, PR002470, PR002471, PR002472, PR001848 and PR000260 bind to human T cells, FIG. 7D: PR001848, PR002742, PR002743 and PR000260 bind to human T cells, FIG. 7E: PR002833, PR002834, PR002835, PR002836, PR002837, PR002742, PR001848, PR002469 and PR000260 bind to human T cells, FIG. 7F: PR003886, PR001848 and PR002742 bind to human T cells, FIG. 7G: PR001848, PR002469 and PR004616 bind to human T cells.

FIG. 10A to FIG. 10G show the capacity of the CD3 antibody to activate human T cells to produce cytokine IFN-γ, wherein FIG. 10A: PR000511, PR000512, PR000513, PR000514 and PR000260 activate T cells, FIG. 10B: PR001848, PR001849 and PR000260 activate T cells, FIG. 10C: PR002468, PR002469, PR002471 and PR001848 activate T cells, FIG. 10D: PR002742, PR001848 and PR000260 activate T cells, FIG. 10E: PR002833, PR002834, PR002835, PR002836, PR002837 and PR000260 activate T cells, FIG. 10F: PR003886, PR001848 and PR002742 activate T cells, FIG. 10G: PR001848, PR002469 and PR004616 activate T cells.

DETAILED DESCRIPTION OF THE PREFERRED EMBODIMENT

Figure 1:
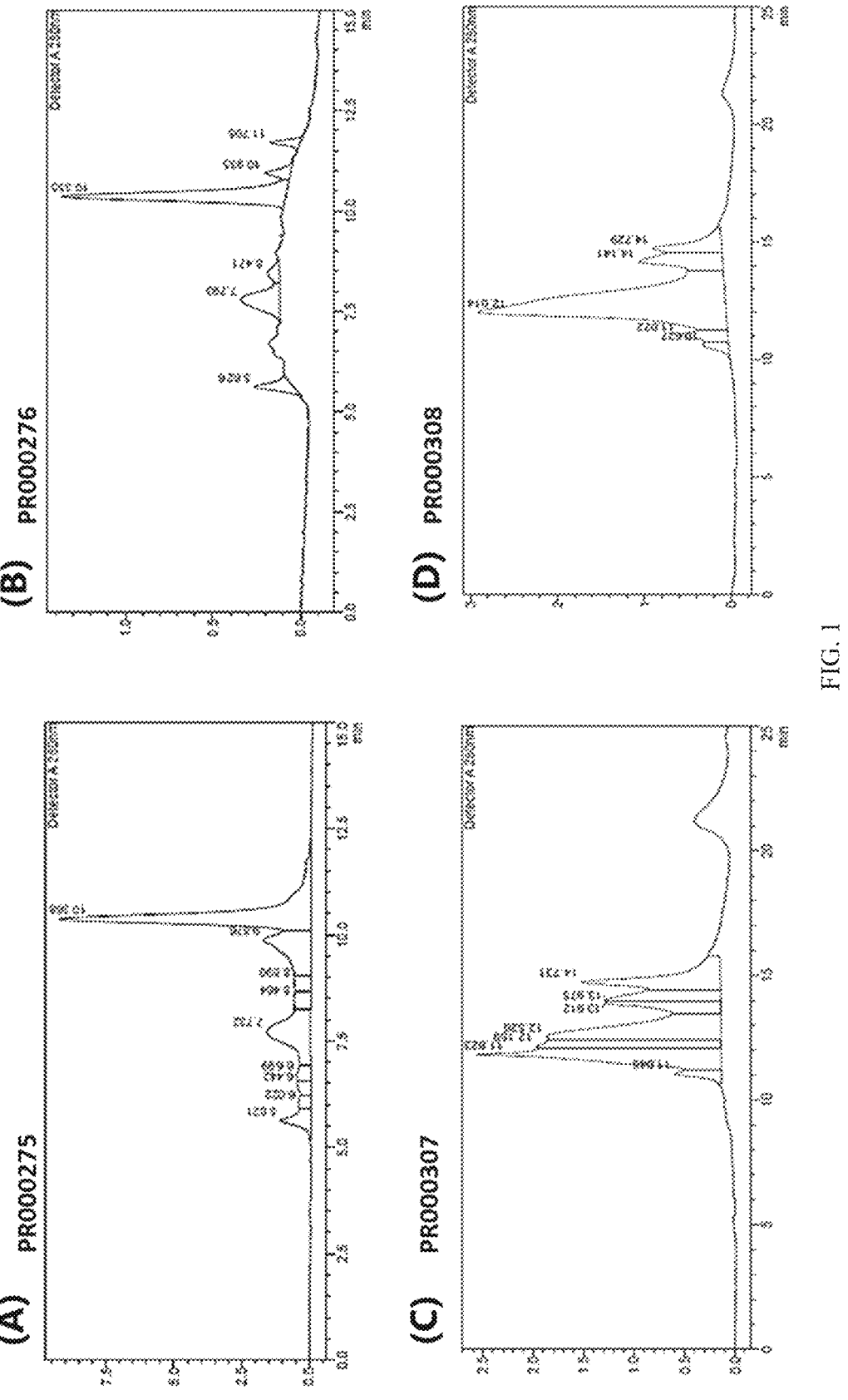
FIG. 1 shows the HPLC-SEC results of the CD3 single-chain antibody after one-step purification: (A) PR000275, (B) PR000276, (C) PR000307, and (D) PR000308.

The present invention is further illustrated below by way of examples, but the invention is not thereby limited to the scope of the described examples. The experimental methods for which specific conditions are not indicated in the following examples were selected according to the conventional methods and conditions, or according to the commodity specification.

In this application, the term "antibody" generally refers to a protein comprising a moiety that binds to an antigen and optionally allows the moiety that binds to the antigen to adopt a scaffold or skeleton moiety of the conformation that promotes binding of the antibody to the antigen. The antibody typically may comprise an antibody light chain variable region (VL), an antibody heavy chain variable region (VH), or both. The VH and VL regions may be further divided into hypervariable regions called complementarity determining regions (CDR), which are scattered in more conservative regions called framework regions (FR). Each of the VH and VL may consist of three CDR and four FR regions, which may be arranged in the following order from the amino end to the carboxyl end: FR1, CDR1, FR2, CDR2, FR3, CDR3, and FR4. The variable regions of the heavy and light chains contain binding domains that interact with the antigen. Examples of the antibody include, but are not limited to, antibody, antigen-binding fragment (Fab, Fab', F(ab)2, Fv fragment, F(ab')2, scFv, di-scFv and/or dAb), immunoconjugate, multispecific antibody (e.g., bispecific antibody), antibody fragment, antibody derivative, antibody analog or fusion protein, and the like, as long as they show the desired antigen-binding activity.

In this application, the term "variable" generally refers to the fact that certain parts of the sequence of the variable domain of the antibody differ substantially, which forms the binding and specificity of various specific antibodies to their particular antigen. However, the variability is not uniformly distributed throughout the variable region of the antibody. It is concentrated in three segments of the light and heavy chain variable regions, known as the complementary determining region (CDR) or high variability region (HVR). The more highly conserved part of the variable domain is known as the framework (FR). The variable structure domains of the natural heavy and light chains each contain four FR regions, most of which adopt the 3-fold conformation and are connected by three CDRs that form a loop linkage and, in some cases, form part of the 3-fold structure. The CDRs in each chain are in close proximity to each other through the FR region and form the antigen binding site of the antibody together with the CDR from the other chain, the constant regions are not directly involved in antibody-antigen binding, but exhibit different effector functions, such as involvement in antibody-dependent cytotoxicity of the antibody. In the present art, the CDR of an antibody can be defined by a variety of methods, such as the Kabat definition scheme based on sequence variability (see, Kabat et al., Sequences of proteins of immunological interest, Fifth Edition, National Institutes of Health, Bethesda, Maryland (1991)) and the Chothia definition scheme based on the location of structural loop regions (see, Al-Lazikani et al., JMol Biol 273:927-48, 1997). In the present application, the Combined definition scheme comprising the Kabat definition and the Chothia definition is also used to identify amino acid residues in variable domain sequences and full-length antibody sequences (Table 1).

TABLE 1

| The CDR definition rules of antibodies in the present application (see http://bioinf.org.uk/abs/) | | | |
|---|---|---|---|
| CDR region | Rabat definition | Chothia definition | Combined definition |
| LCDR1 | L24--L34 | L24--L34 | L24--L34 |
| LCDR2 | L50--L56 | L50--L56 | L50--L56 |
| LCDR3 | L89--L97 | L89--L97 | L89--L97 |
| HCDR1 | H31--H35 | H26--H32 | H26--H35 |
| HCDR2 | H50--H65 | H52--H56 | H50--H65 |
| HCDR3 | H95--H102 | H95--H102 | H95--H102 |

Wherein, Laa-Lbb may refer to the amino acid sequence from position aa (Chothia numbering scheme) to position bb (Chothia numbering scheme) starting from the N-terminal of the antibody light chain; Haa-Hbb may refer to the amino acid sequence from position aa (Chothia coding scheme) to position bb (Chothia numbering scheme) starting from the N-terminal of the antibody heavy chain. For example, L24-L34 may refer to the amino acid sequence from position 24 to position 34 starting from the N-terminal of the light chain of the antibody according to the Chothia numbering scheme; H26-H32 may refer to the amino acid sequence from position 26 to position 32 starting from the N-terminal of the heavy chain of the antibody according to the Chothia numbering scheme.

The antibody Fc domain-mediated effector functions such as ADCC and CDC also have very important biological functions, different IgG isoforms have different ADCC or CDC functions, for example, IgG1 and IgG3 have strong ADCC and CDC effects, while IgG2 and IgG4 have relatively weak effects. In addition, the original effector function of Fc can also be modulated by amino acid mutations or modifications to alter the binding ability of Fc to the Fc receptor. For example, the "LALA" double mutation (L234A/L235A) in IgG1 significantly reduces the affinity to FcγRIIIA (CD16A) and thus reduces the ADCC effect. In addition, the P329G mutation significantly reduces the binding of IgG1 multiple Fcγ receptors (see, Schlothauer T, Herter S, Koller C F, et al. Protein Eng Des Sel. 2016 October; 29(10):457-466). In this application, in order to reduce the binding of CD3 antibodies to the Fcγ receptor, "LALA" double mutation (L234A/L235A) or the "LALAPG" triple mutation (L234A/L235A/P329G) was introduced into the Fc of these CD3 antibodies.

Example 1 Preparation and Characterization Analysis of Recombinant Antibodies

1.1 Preparation of IgG Recombinant Antibodies

After obtaining the light and heavy chain variable domain sequences encoding the antibody molecule, the recombinant antibody molecule can be prepared by fusion expression of the light and heavy chain variable domain sequences with the corresponding human antibody light and heavy chain constant domain sequences using conventional recombinant DNA techniques. In this example, the antibody heavy chain variable domain sequence (VH) is genetically synthesized and cloned into the mammalian cell expression plasmid vector encoding the human IgG1 antibody heavy chain constant domain sequence to obtain the full-length heavy chain of IgG1 antibody by encoding, and the "LALA" double mutation (L234A/L234A)(SEQ ID NO: 63) or the "LALAPG" triple mutation (L234A/L235A/P329G)(SEQ ID NO: 64) is introduced in the IgG1 heavy chain constant region to reduce the antibody binding to the Fc7 receptor.

The sequence of antibody light chain variable domain (VL) is genetically synthesized and cloned into the mammalian cell expression plasmid vector encoding the sequence of human antibody κ light chain constant domain (SEQ ID NO: 61) to obtain the full length κ light chain of antibody by encoding; alternatively, VL is genetically synthesized and cloned into the mammalian cell expression plasmid vector encoding the sequence of human antibody λ light chain constant domain (SEQ ID NO: 62) to obtain the full length λ light chain to produce antibody by encoding.

By co-transfecting mammalian host cell (e.g., human embryonic kidney cell HEK293) with plasmids encoding the antibody heavy chain and plasmids encoding the antibody light chain, the purified recombinant antibody with correctly paired assembly of light and heavy chains can be obtained using conventional recombinant protein expression and purification techniques. Specifically, the HEK293 cells were expanded in medium FreeStyle™ F17 Expression Medium (Thermo, #A1383504). Before transient transfection, adjusted the cell concentration to $6\text{-}8\times10^5$ cells/ml and incubated them in shaker at 37° C. 8% $CO_2$ for 24 hours at the cell concentration of $1.2\times10^6$ cells/ml. 30 ml of cultured cells were prepared. The plasmid encoding the heavy chain and the plasmid encoding the light chain were mixed in a ratio of 2:3, a total of 30 g plasmid were dissolved in 1.5 mL Opti-MEM reduced serum medium (Thermo, #31985088) and filtered through the 0.22 μm membrane. Then 1.5 mL opti-MEM was dissolved into 120 μL 1 mg/mL PEI (Polysciences, #23966-2), and left standing for 5 minutes. PEI was slowly added to the plasmid, thereafter incubating for 10 minutes at room temperature. The mixed solution of plasmid PEI was slowly added into a culture flask dropwise while shaking the culture flask. The transfected cells were incubated at 37° C., 8% $CO_2$ in a shaker for 5 days. The cell viability were observed after 5 days. Then cultures were harvested by centrifugation at 3300 g for 10 minutes to collect the supernatant. Impurities in the supernatant was removed by centrifugation at high speed. The gravity column (Bio-Rad, #7311550) containing MabSelect™ (GE Healthcare Life Science, #71-5020-91 AE) was equilibrated with PBS (pH 7.4) and rinsed with 2-5 times of the column volume of PBS. The column was loaded with the supernatant sample and rinsed with 5-10 times of the column volume of PBS. Then the target protein was elutd with 0.1 M glycine at pH 3.5, later adjusted to neutral pH with Tris-HCl at pH 8.0, finally concentrated using the ultrafiltration tube (Millipore, #UFC901024) and exchanged to PBS buffer and to obtain the purified recombinant antibody solution. At last, measured the concentration by NanoDrop (Thermo Scientific™ NanoDrop™ One), dispensed and stored the purified recombinant antibody solution for backup.

1.2 Preparation of Monovalent scFv-his Recombinant Antibodies

The VH and VL sequences of the antibody were linked by a flexible peptide (Linker) to obtain a single polypeptide chain encoding both VH and VL, i.e., a single chain antibody variable region fragment (scFv). If a linker peptide of suitable length, such as $(G_4S)_3$ (SEQ ID NO: 65) or $(G_4S)_4$ (SEQ ID NO: 66), is selected, VH and VL can be correctly folded and assembled into functional antibodies. Different scFv structures (VH-linker-VL or VL-linker-VH) can be constructed depending on the different arrangements of VH and VL and difference of the linker peptide. A single scFv contains an antigen-binding region consisting of a pair of VH and VL, which usually binds only one antigen molecule and is thus called a monovalent binding molecule.

To facilitate purification, in this example, The C-terminal of the scFv was fused with His tag composed of 6-Histidine. The plasmid encoding the scFv and His tag was genetically synthesized and cloned into expression plasmid vector for mammalian cells to obtain the plasmid encoding scFv-his, which was transfected into mammalian host cell (e.g., human embryonic kidney cell HEK293), and then the recombinant protein can be purified using conventional recombinant protein expression and purification techniques. Specifically, the HEK293 cells were expanded in medium FreeStyle™ F17 Expression Medium (Thermo, #A1383504). Before transient transfection, adjusted the cell concentration to $6\text{-}8\times10^5$ cells/ml and incubated them in shaker at 37° C. 8% $CO_2$ for 24 hours at the cell concentration of $1.2\times10^6$ cells/ml. 30 ml of cultured cells were prepared. 30 g of the plasmid were dissolved in 1.5 mL Opti-MEM reduced serum medium (Thermo, #31985088) and filtered through the 0.22 μm membrane. Then 1.5 mL opti-MEM was dissolved into 120 μL 1 mg/mL PEI (Polysciences, #23966-2), and left standing for 5 minutes. PEI was slowly added to the plasmid, thereafter incubating for 10 minutes at room temperature. The mixed solution of plasmid-PEI was slowly added into a culture flask dropwise while shaking the culture flask. The transfected cells were incubated at 37° C., 8% $CO_2$ in a shaker for 5 days. The cell viability were observed after 5 days. Then cultures were harvested by centrifugation at 3300 g for 10 minutes to collect the supernatant. Impurities in the supernatant was removed by centrifugation at high speed. The gravity column (Bio-Rad, #7311550) containing Ni Sepharose excel (GE Healthcare Life Science, #17-3712-01) Ni Sepharose excel (GE Healthcare Life Science, #17-3712-01) was equilibrated with PBS (pH 7.4) and rinsed with 2-5 times of the column volume of PBS. The column was loaded with the supernatant sample; and rinsed with 5-10 times of the column volume of PBS. Non-specifically adsorbed heteroproteins was eluted with buffer A (containing 20 mM imidazole, 150 mM phosphate, pH 8.0) first, and then the target protein with buffer B (containing 500 mM imidazole, 150 mM phosphate, pH 8.0), finally using the ultrafiltration tube (Millipore, #UFC901024) to concentrate and exchange the solution to PBS buffer and to obtain the purified recombinant antibody solution. At last, measured the concentration by NanoDrop (Thermo Scientific™ NanoDrop™ One), dispensed and stored the purified recombinant antibody solution for backup.

1.3 Preparation of Bivalent scFv-Fc Recombinant Antibodies

In this example, the scFv-Fc recombinant molecule was constructed by fusing the sequence of human IgG1 constant region Fc (Glu216-Lys447, containing the hinge region, CH2 domain and CH3 domain) at the C-terminus of scFv, and through homodimerization of Fc, a bivalent scFv-Fc dimer molecule was formed, which is capable of binding two antigen molecules simultaneously. And the "LALA" double mutation (L234A/L235A) or the "LALAPG" triple mutation (L234A/L235A/P329G) was introduced into Fc to reduce the binding of the antibody to the Fcγ receptor. The polypeptide sequence encoding scFv-Fc was genetically synthesized and cloned into the expression plasmid vector for mammalian cells to obtain the plasmid encoding scFv-Fc, which was thereafter transfected into mammalian host cells (e.g., human embryonic kidney cell HEK293), and then using the protein expression purification method described in the Example 1.1 to obtain the purified recombinant protein.

1.4 Protein Purity Analysis by HPLC-SEC

The purity and aggregate form of protein samples were analyzed by molecular size exclusion chromatography (SEC). The analytical column TSKgel G3000SWx1 (Tosoh Bioscience, #08541, 5 μm, 7.8 mm×30 cm) was connected to the high pressure liquid chromatograph (HPLC) (Agilent Technologies, Agilent 1260 Infinity II) and equilibrated with PBS buffer at room temperature for at least 1 hour. An appropriate amount of protein sample (at least 10 μg) filtered through the 0.22 μm membrane were injected into the system, and the HPLC program was set: the column was loaded by the sample with PBS buffer at a flow rate of 1.0 ml/min for a maximum of 20 minutes. HPLC will generate Analytical reports of HPLC would be generated, which reports the retention time of the different molecular size components in the sample.

Example 2 Recombinant Expression of Murine-Human Chimeric Antibody of CD3 Antibody SP34

SP34 is a murine-derived anti-human CD3F antibody that binds a variety of primate CD3 and functions to activate T cells. The sequences of variable region VH and VL of SP34 have been disclosed in WO2016071004A1. In this application, the amino acid sequence of VH of SP34 is set for in SEQ ID NO: 42, and its corresponding murine germline V gene is IGHV10-1; the amino acid sequence of VL of SP34 is set forth in SEQ ID NO: 56, and its corresponding murine germline V gene is IGLV1. In this example, the VH sequence of SP34 was fused with the human IgG1 antibody heavy chain constant domain sequence (SEQ ID NO: 63) comprising a "LALA" double mutation(L234A/L235A) to produce the full-length heavy chain of SP34 murine-human chimeric IgG1 antibody; the amino acid sequence of VL of SP34 was fused with the human antibody λ light chain constant domain sequence (SEQ ID NO: 62) to produce the full length λ light chain of the SP34 murine-human chimeric antibody.

The SP34 murine-human chimeric recombinant antibody PR000260 was prepared according to the method of the Example 1.1. The following Table 2 shows the data of recombinant expression of PR000260.

TABLE 2

| Expression and purification of recombinant antibody PR000260 | | | | |
|---|---|---|---|---|
| Antibody number | Expression system (volume) | Purification method | Yield (mg/L) | HPLC-SEC (monomer purity %) |
| PR000260 | HEK293 (100 ml) | MabSelect | 19.30 | 99.75% |

Example 3 Convert Murine CD3 SP34 Antibody to Recombinant scFv Antibody

The VH sequence (SEQ ID NO: 42) and VL sequence (SEQ ID NO: 56) of SP34 were linked by the flexible peptide (Linker) to obtain the single polypeptide chain encoding both VH and VL, i.e., the single chain antibody variable region fragment (scFv). Depending on the different arrangements of VH and VL and different lengths of the linker peptides (SEQ ID NO: 65, SEQ ID NO: 66), different scFv structures can be constructed, and a His tag consisting of a 6-Histidine was fused at the C-terminus of the scFv for purification. The linker peptide as shown in SEQ ID NO: 67 can also be used for the construction of scFv in this application.

In this Example, four recombinant scFv antibody molecules (PR000275, PR000276, PR000307, PR000308) were prepared according to the method of the Example 1.2. The sequence numbers of these four recombinant scFv antibody molecules are listed in Table 3 below; the following Table 4 shows the expression data of of these four recombinant molecules; and the HPLC-SEC results of these four molecules after one-step purification are shown in FIG. 1, wherein (A) shows the result of PR000275, (B) shows the result of PR000276, (C) shows the result of PR000307, and (D) shows the result of PR000308. It can be seen that using the sequences of VH and VL of SP34 to construct scFv, no matter which (VH/VL) alignment pattern was used or the length of the linking peptide was changed, no stable scFv could be obtained.

TABLE 3

| Structure and sequence number of the four recombinant antibodies | | | | | | | | |
|---|---|---|---|---|---|---|---|---|
| Antibody number | VH Variant | VL Variant | Molecular structure | scFv Structure | VH | VL | Linker peptide (SEQ ID NOs:) | Full length sequence (SEQ ID NOs:) |
| PR000275 | SP34_VH | SP34_VL | scFv-his | VL-linker-VH | 42 | 56 | 65 | 68 |
| PR000276 | SP34_VH | SP34_VL | scFv-his | VH-linker-VL | 42 | 56 | 65 | 69 |
| PR000307 | SP34_VH | SP34_VL | scFv-his | VL-linker-VH | 42 | 56 | 66 | 70 |
| PR000308 | SP34_VH | SP34_VL | scFv-his | VH-linker-VL | 42 | 56 | 66 | 71 |

TABLE 4

| Expression and purification of recombinant scFv antibodies | | | | | |
|---|---|---|---|---|---|
| Antibody number | Structure | HEK293 Expression Volume | Purification method | Yield (mg/L) | HPLC-SEC (monomer purity %) |
| PR000275 | VL-(G4S)3-VH | 100 ml | Nickel | 2.60 | 46.61% |
| PR000276 | VH-(G4S)3-VL | 100 ml | Nickel | 0.26 | Weak signal |
| PR000307 | VL-(G4S)4-VH | 30 ml | Nickel | 3.33 | Weak signal |
| PR000308 | VH-(G4S)4-VL | 30 ml | Nickel | 3.67 | Weak signal |

Example 4 Sequence Optimization of SP34

4.1 Humanization of Variable Region Sequences and Mutation of Frame Region

The "CDR transplantation" method is used for sequence humanization in this example, i.e., transplantation of the CDR of the murine antibody VH to the frame region of the human antibody VH, and transplantation of the CDR of the murine antibody VL to the frame region of the human antibody VL. The sequence of the frame region of human antibody VH or VL can be derived from human germline gene sequences or antibody sequences that have been rearranged by V(D)J or the consensus sequences of the specific VH or VL gene family of the human antibody. In this example, the frame region sequences provided by human germline gene sequences are used as humanized template sequences, i.e., the human germline V gene fragment provides the sequences of the frame regions FR1, FR2, and FR3, and the human germline J gene fragment provides the sequence of the frame region FR4. Finally, the sequences of humanized variable region (VH or VL) were constructed in the arrangement of (human)FR1-(murine)CDR1-(human) FR2-(murine)CDR2-(human)FR3-(murine)CDR3-(human) FR4.

In this example, the sequence of the human germline V gene fragment IGHV3-73*01 or the human germline V gene fragment IGHV3-23*01 was used as the humanized template in combination with the sequence of the human germline J gene fragment IGHJ1*01 to provide the frame region sequence. Amino acid mutations at one or more sites were introduced in at the position 30, position 73, position 76, position 78, position 93 or position 94 (according to Chothia numbering rules) to obtain several different VH mutant sequences.

In this example, the sequence of the human germline V gene fragment IGLV7-46*02 combined with the sequence of the human germline J gene fragment IGLJ2*01 or the sequence of the human germline V gene fragment IGKV1-39*01 combined with the sequence of the human germline J gene fragment IGKJ4*01 was used as the humanized template to provide the frame region sequence. Amino acid mutations at zero or more sites were introduced in at the position 2, position 36, position 46, position 49, position 66, position 69, position 71 or position 87 (according to Chothia numbering scheme) to obtain several different VL mutant sequences.

The following Table 5 lists the sequence numbers of the antibody variable region, its optimized mutant sequences (FV) and the sequences of the CDR and FR regions defined by CHOTHIA.

TABLE 5

| | | | | Variable region of SP34 antibody and optimized mutant sequences (FV) thereof and the sequence list of CDR and FR regions defined by CHOTHIA | | | | |
|---|---|---|---|---|---|---|---|---|
| ID | FV | FR1 | CDR1 | FR2 | CDR2 | FR3 | CDR3 | FR4 |
| SP34_VH | 42 | 5 | 1 | 8 | 3 | 11 | 4 | 21 |
| VH3730 | 50 | 7 | 1 | 10 | 3 | 17 | 4 | 22 |
| VH3731 | 51 | 7 | 1 | 10 | 3 | 18 | 4 | 22 |
| VH3732 | 52 | 7 | 2 | 10 | 3 | 18 | 4 | 22 |
| VH3733 | 53 | 7 | 2 | 10 | 3 | 19 | 4 | 22 |
| VH3734 | 54 | 7 | 2 | 10 | 3 | 20 | 4 | 22 |
| VH3735 | 55 | 7 | 2 | 10 | 3 | 17 | 4 | 22 |
| VH3230 | 43 | 6 | 1 | 9 | 3 | 12 | 4 | 22 |
| VH3231 | 44 | 6 | 1 | 9 | 3 | 13 | 4 | 22 |

TABLE 5-continued

| | | | | Variable region of SP34 antibody and optimized mutant sequences (FV) thereof and the sequence list of CDR and FR regions defined by CHOTHIA | | | | |
|---|---|---|---|---|---|---|---|---|
| ID | FV | FR1 | CDR1 | FR2 | CDR2 | FR3 | CDR3 | FR4 |
| VH3232 | 45 | 6 | 2 | 9 | 3 | 13 | 4 | 22 |
| VH3233 | 46 | 6 | 2 | 9 | 3 | 12 | 4 | 22 |
| VH3234 | 47 | 6 | 2 | 9 | 3 | 14 | 4 | 22 |
| VH3235 | 48 | 6 | 2 | 9 | 3 | 15 | 4 | 22 |
| VH3236 | 49 | 6 | 2 | 9 | 3 | 16 | 4 | 22 |
| SP34_VL | 56 | 26 | 23 | 30 | 24 | 35 | 25 | 40 |
| VL7460 | 57 | 27 | 23 | 33 | 24 | 38 | 25 | 40 |
| VL7461 | 58 | 27 | 23 | 34 | 24 | 39 | 25 | 40 |
| VK1392 | 59 | 28 | 23 | 31 | 24 | 36 | 25 | 41 |
| VK1393 | 60 | 29 | 23 | 32 | 24 | 37 | 25 | 41 |

Figure 2:
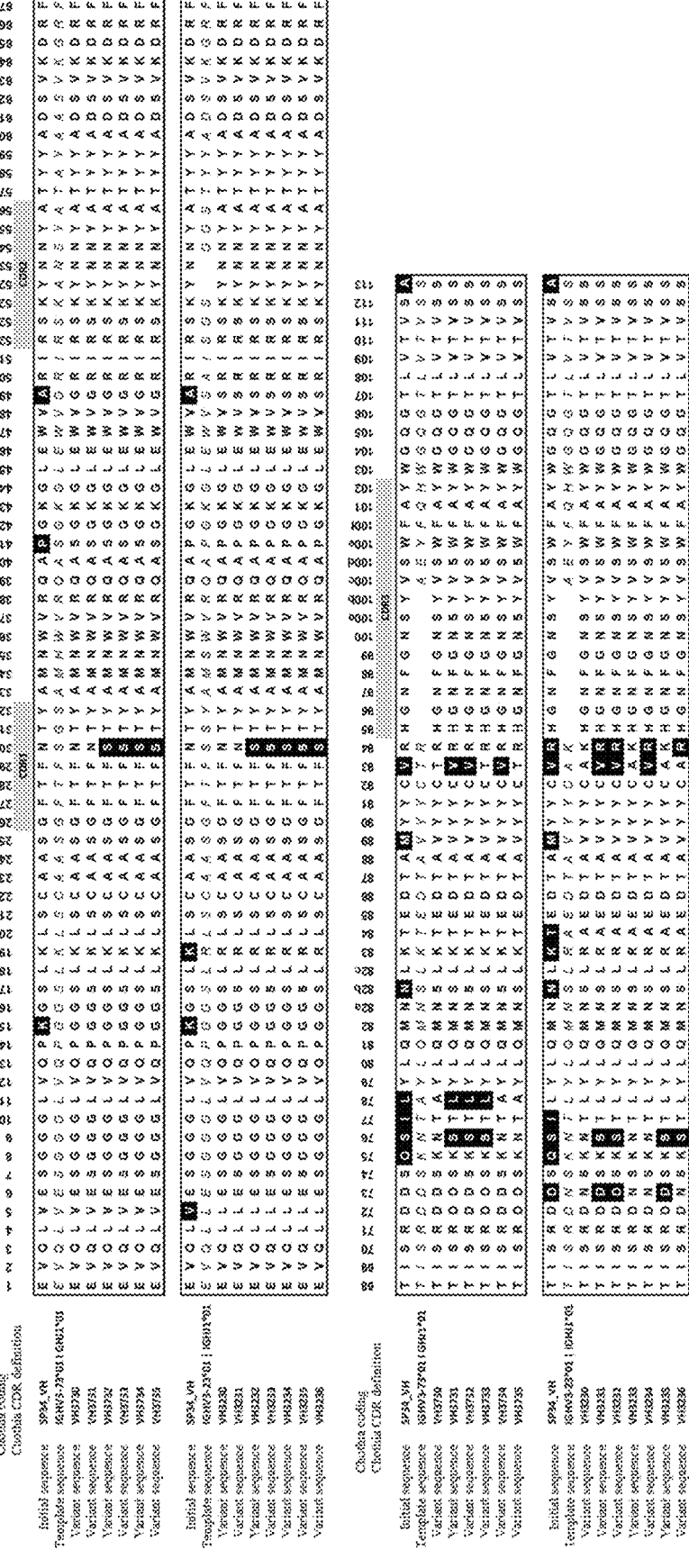
FIG. 2 shows the sequence alignment of the humanized mutants of SP34 VH.
Figure 3:
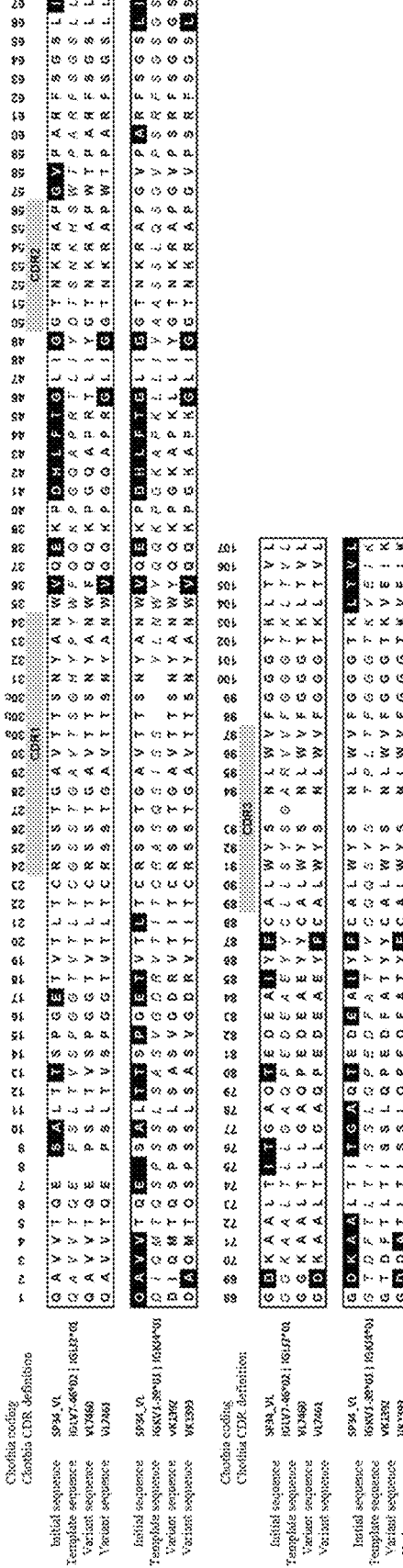
FIG. 3 shows the sequence alignment of humanized mutants of SP34 VL.
Figure 4:
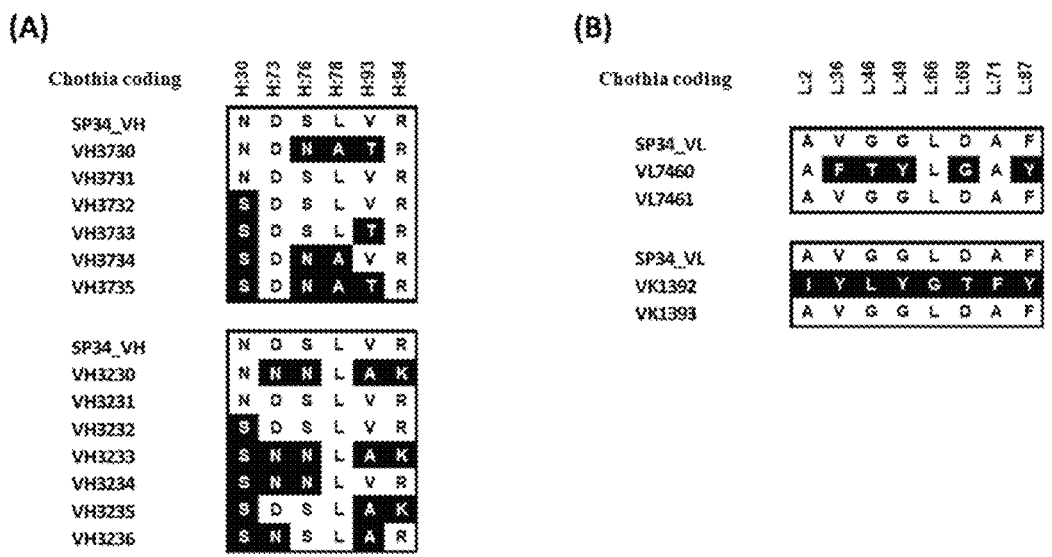
FIG. 4 shows the differences in significant sites of different VH/VL mutant sequences, wherein (A) shows the VH mutant sequence and (B) shows the VL mutant sequence.

FIG. 2 lists the comparison of VH mutant sequences. FIG. 3 lists the comparison of VL mutant sequences. The differences in the sequences of VH mutants and VL mutants at significant sites are listed in (A) and (B) of FIG. 4, respectively. As can be seen from FIG. 2 to FIG. 4, the mutations of the antibody of the present invention on VH occurred at one or more sites selected from position 30, position 73, position 76, position 78, position 93 or position 94 of the amino acid sequence as shown in SEQ ID NO: 42. The mutations on the VL occurred at position 2, position 36, position 46, position 49, position 66, position 69, position 71 and/or position 87 of the sequence as shown in SEQ ID NO: 56. More detailed mutation information can be found in Table 5 for sequence specifics of VH3730, VH3731, VH3732, VH3733, VH3734, VH3735, VH3230, VH3231, VH3232, VH3233, VH3234, VH3235, VH3236, VL7460, VL7461, VK1392, and VK1393.

4.2 Recombinant Antibodies of Mutants with Optimized Sequences

The sequences of VH mutants and VL mutants obtained in the Example 4.1 were paired and combined, and the IgG recombinant antibody constructed according to the method in the Example 1.1, wherein the "LALA" double mutation or the "LALAPG" triple mutation was introduced into the constant region of the IgG1 heavy chain to reduce the Fc effector function. Table 6 lists the sequences of recombinant antibody molecules that have been sequence optimized. Table 7 lists the expression data of the recombinant antibodies. Except for the three IgG molecules constructed with the VH mutant VH3230, which have very low expression yields, all other IgG molecules have reasonable expression yields.

TABLE 6

| | | | | | Sequence list of the SP34 chimeric antibodies or antibodies with optimized sequence | |
|---|---|---|---|---|---|---|
| Antibody number | VH Mutant | VL Mutant | VH | VL (SEQ ID NOs:) | Heavy chain constant region | Light chain constant region |
| PR000260 | SP34_VH | SP34_VL | 42 | 56 | 63 | 62 |
| PR000511 | VH3231 | VL7461 | 44 | 58 | 63 | 62 |
| PR000512 | VH3731 | VL7461 | 51 | 58 | 63 | 62 |
| PR000513 | VH3231 | VK1393 | 44 | 60 | 63 | 61 |
| PR000514 | VH3731 | VK1393 | 51 | 60 | 63 | 61 |
| PR001848 | VH3232 | VL7461 | 45 | 58 | 64 | 62 |
| PR001849 | VH3732 | VL7461 | 52 | 58 | 64 | 62 |

TABLE 6-continued

Sequence list of the SP34 chimeric antibodies
or antibodies with optimized sequence

| Antibody number | VH Mutant | VL Mutant | VH | VL | Heavy chain constant region | Light chain constant region |
|---|---|---|---|---|---|---|
| | | | | | (SEQ ID NOs:) | |
| PR002467 | VH3230 | VL7460 | 43 | 57 | 63 | 62 |
| PR002468 | VH3231 | VL7460 | 44 | 57 | 63 | 62 |
| PR002469 | VH3230 | VL7461 | 43 | 58 | 63 | 62 |
| PR002470 | VH3230 | VK1392 | 43 | 59 | 63 | 61 |
| PR002471 | VH3231 | VK1392 | 44 | 59 | 63 | 61 |
| PR002472 | VH3230 | VK1393 | 43 | 60 | 63 | 61 |
| PR002742 | VH3730 | VL7461 | 50 | 58 | 63 | 62 |
| PR002743 | VH3731 | VL7460 | 51 | 57 | 63 | 62 |
| PR002833 | VH3234 | VL7461 | 47 | 58 | 64 | 62 |
| PR002834 | VH3235 | VL7461 | 48 | 58 | 64 | 62 |
| PR002835 | VH3236 | VL7461 | 49 | 58 | 64 | 62 |
| PR002836 | VH3733 | VL7461 | 53 | 58 | 64 | 62 |
| PR002837 | VH3734 | VL7461 | 54 | 58 | 64 | 62 |
| PR003886 | VH3735 | VL7461 | 55 | 58 | 63 | 62 |
| PR004616 | VH3233 | VL7461 | 46 | 58 | 63 | 62 |

TABLE 7

Expression yield and purity of the recombinant antibodies

| Antibody number | VH Mutant | VL Mutant | Yield of HEK293 (mg/L) | HPLC-SEC monomer purity (%) |
|---|---|---|---|---|
| PR000260 | SP34_VH | SP34_VL | 64.33 | 99.75% |
| PR000511 | VH3231 | VL7461 | 48.33 | 99.88% |
| PR000512 | VH3731 | VL7461 | 150.00 | 100.00% |
| PR000513 | VH3231 | VK1393 | 45.00 | 100.00% |
| PR000514 | VH3731 | VK1393 | 48.33 | 100.00% |
| PR001848 | VH3232 | VL7461 | 38.50 | 99.03% |

TABLE 7-continued

Expression yield and purity of the recombinant antibodies

| Antibody number | VH Mutant | VL Mutant | Yield of HEK293 (mg/L) | HPLC-SEC monomer purity (%) |
|---|---|---|---|---|
| PR001849 | VH3732 | VL7461 | 43.50 | 99.10% |
| PR002467 | VH3230 | VL7460 | 0.60 | n/a |
| PR002468 | VH3231 | VL7460 | 107.25 | 98.84% |
| PR002469 | VH3230 | VL7461 | 10.20 | 96.85% |
| PR002470 | VH3230 | VK1392 | 0.60 | n/a |
| PR002471 | VH3231 | VK1392 | 62.50 | 94.96% |
| PR002472 | VH3230 | VK1393 | 0.30 | n/a |
| PR002742 | VH3730 | VL7461 | 14.25 | 100.00% |
| PR002743 | VH3731 | VL7460 | 44.25 | 100.00% |
| PR002833 | VH3234 | VL7461 | 18.00 | 98.92% |
| PR002834 | VH3235 | VL7461 | 24.60 | 95.88% |
| PR002835 | VH3236 | VL7461 | 13.50 | 95.58% |
| PR002836 | VH3733 | VL7461 | 26.25 | 94.68% |
| PR002837 | VH3734 | VL7461 | 17.20 | 97.36% |
| PR003886 | VH3735 | VL7461 | 116 | 98.49% |
| PR004616 | VH3233 | VL7461 | 22 | n/a |

4.3 Recombinant scFv Molecules Containing Mutants with Optimized Sequences

Figure 5:
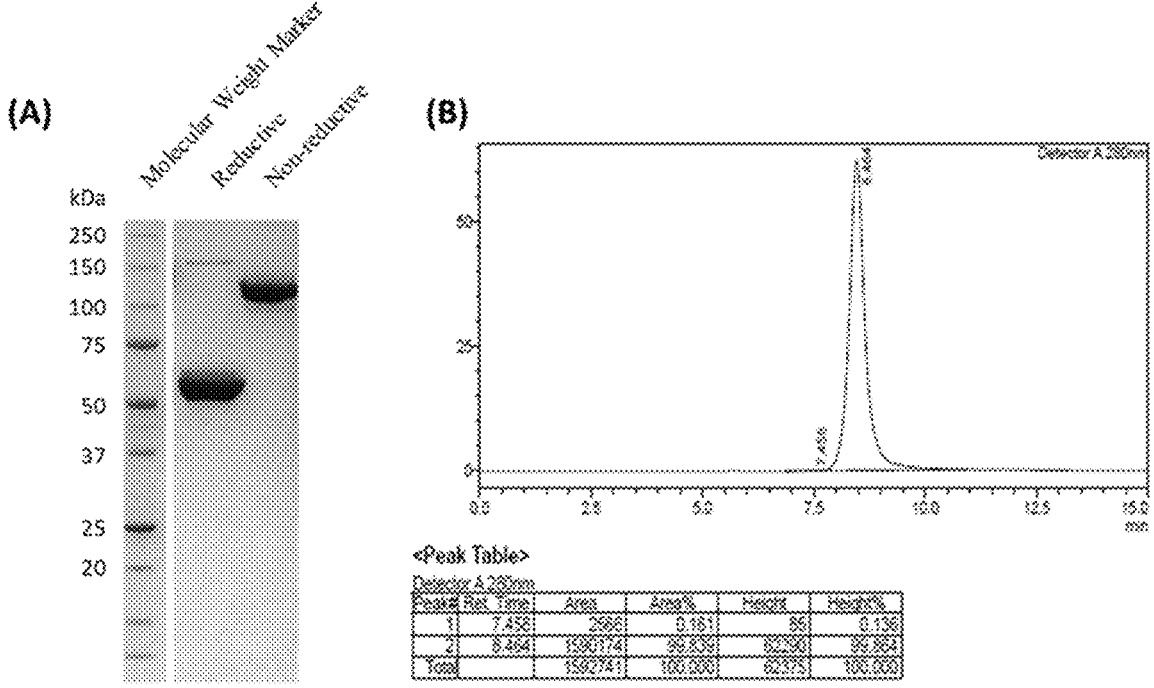
FIG. 5 shows (A) SDS-PAGE results and (B) HPLC-SEC results of the CD3 single chain antibody PR000510 after one-step purification.

The sequences of VH mutants and VL mutants obtained in the Example 4.1 were paired and combined, and a plurality of recombinant bivalent scFv antibody molecules were obtained according to the method in the Example 1.3. The following Table 8, 9 respectively lists the sequence information and protein expression of the scFv. As can be seen in Table 9, PRVH751 and PR000627 are especially better expressed and stable molecules. FIG. 5 shows the results of (A) SDS-PAGE and (B) HPLC-SEC of PR000510, which can be seen that it has a good monomeric purity with no obvious aggregates.

TABLE 8

Structure and sequence information of the scFv molecules
constructed based on the mutants with optimized sequences

| Antibody number | VH Mutant | VL Mutant | Molecular structure | scFv Structure | VH | VL | Linker peptide | Full length sequence |
|---|---|---|---|---|---|---|---|---|
| | | | | | (SEQ ID NOs:) | | | |
| PR000509 | VH3731 | VL7461 | scFv-Fc | VH-linker-VL | 51 | 58 | 67 | 72 |
| PR000510 | VH3731 | VL7461 | scFv-Fc | VL-linker-VH | 51 | 58 | 67 | 73 |
| PR000623 | VH3231 | VK1393 | scFv-Fc | VH-linker-VL | 44 | 60 | 67 | 74 |
| PR000624 | VH3731 | VK1393 | scFv-Fc | VH-linker-VL | 51 | 60 | 67 | 75 |
| PR000625 | VH3231 | VK1393 | scFv-Fc | VL-linker-VH | 44 | 60 | 67 | 76 |
| PR000626 | VH3731 | VK1393 | scFv-Fc | VL-linker-VH | 51 | 60 | 67 | 77 |
| PR000627 | VH3731 | VL7461 | scFv-Fc | VL-linker-VH | 51 | 58 | 67 | 78 |
| PR000914 | VH3231 | VL7461 | scFv-Fc | VH-linker-VL | 44 | 58 | 67 | 79 |
| PR000915 | VH3231 | VL7461 | scFv-Fc | VL-linker-VH | 44 | 58 | 67 | 80 |
| PR001850 | VH3732 | VL7461 | scFv-Fc | VL-linker-VH | 52 | 58 | 67 | 81 |

TABLE 9

Expression data of the scFv antibody after sequence optimization

| Antibody number | VH Mutant | VL Mutant | Yield of HEK293 (mg/L) | HPLC-SEC monomer purity (%) |
|---|---|---|---|---|
| PR000509 | VH3731 | VL7461 | 0.00 | n/a |
| PR000510 | VH3731 | VL7461 | 7.00 | 99.84% |
| PR000623 | VH3231 | VK1393 | 0.60 | 93.29% |
| PR000624 | VH3731 | VK1393 | 1.80 | 100.00% |
| PR000625 | VH3231 | VK1393 | 0.00 | n/a |
| PR000626 | VH3731 | VK1393 | 0.00 | n/a |
| PR000627 | VH3731 | VL7461 | 6.00 | 100.00% |
| PR000914 | VH3231 | VL7461 | 3.33 | 78.22% |
| PR000915 | VH3231 | VL7461 | 2.67 | 86.14% |
| PR001850 | VH3732 | VL7461 | 4.88 | 50.76% |

Example 5 Determination of the Binding Capacity
of CD3 Antibody to CD3 Expressing Cells by
FACs The flow cytometryFACS was used to analyse the binding of the CD3 antibody to CD3-expressing cells, where the CD3-expressing cells could be: CHOK1 cells overexpressing human CD3 or HEK 293cells (plasmids encoding the ORF of γ, δ, ε, and chains of human-derived CD3 and plasmids encoding the ORF of α and β chains of human TCR were co-transfected with host cells CHOK1 (ATCC, CCL-61) or HEK293 (ATCC, CRL-1573) to construct stable cell lines expressing the structure of the human TCR/CD3 complex); CHOK1 or HEK293 cells overexpressing cynomolgus monkey CD3; human pan-T cells (isolated with the human pan-T cell isolation kit (Miltenyi, #130-096-535) from PBMC); cynomolgus monkey pan-T cells. Specifically, the collected cells were washed twice with PBS containing 2% FBS (FACS buffer), and resuspended with FACS buffer, divided into 96 well plates with $1 \times 10^5$ cells per well, centrifuged at 500 g for 5 minutes. The supernatant was discarded, and 100 l of pre-gradient diluted CD3 antibody was added, then incubating for 1 hour at room temperature and washing twice with FACS buffer. The cells were resuspended with FACS buffer diluted with secondary antibody Alexa Fluor 488 AffiniPure Goat Anti-Human IgG, Fcγ fragment specific (Jackson ImmunoResearch, #109-545-098), then incubated at room temperature in the dark for 30 minutes. The cells were washed twice with FACS buffer, and resuspended with 200 µl FACS buffer. The fluorescent luminescence signal value were read by flow cytometry (BD FACS CANTOII or ACEA NovoCyte), and the resulted data were processed and analyzed by software FlowJo v10 (FlowJo, LLC). The software GraphPad Prism 8 was used for data processing and graphical analysis, and parameters such as binding curves and EC50 values can be obtained by four-parameter nonlinear fitting.

Figure 6:
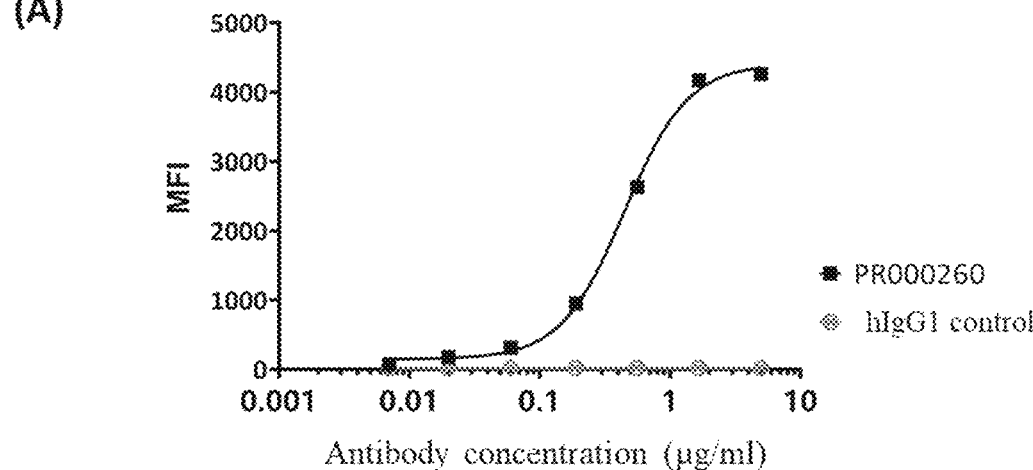
FIG. 6 shows the binding capacity of the CD3 antibody PR000260 to (A) recombinant CHOK1 cells overexpressing human CD3 and (B) recombinant CHOK1 cells overexpressing cynomolgus monkey CD3.
Figure 6:
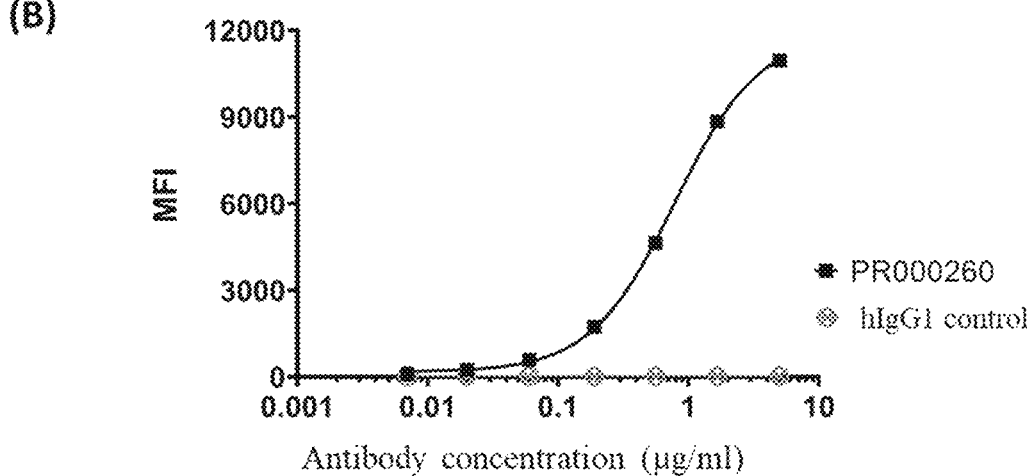
Figure 7A:
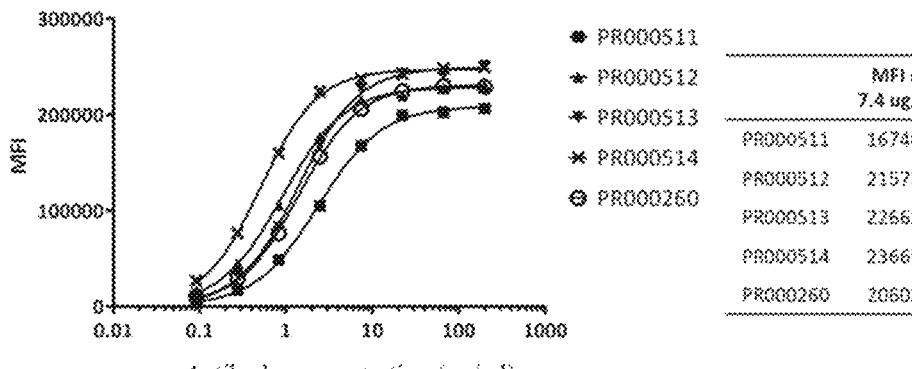
FIG. 7A to FIG. 7G show the binding capacity of the CD3 antibody to human T cells, including the binding curve and MFI relative intensity (fluorescence intensity MFI of the antibody binding to human T cells at specific concentrations, and relative ratio compared to the initial antibody PR000260 (SP34)) or MFI maximum, wherein FIG. 7A PR000511, PR000512, PR000513, PR000514 and PR000260 bind to human T cells.
Figure 7B:
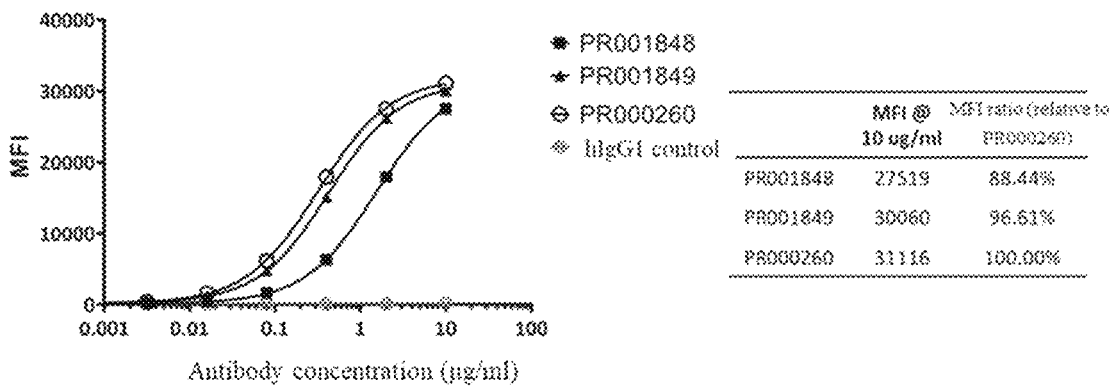
Figure 7C:
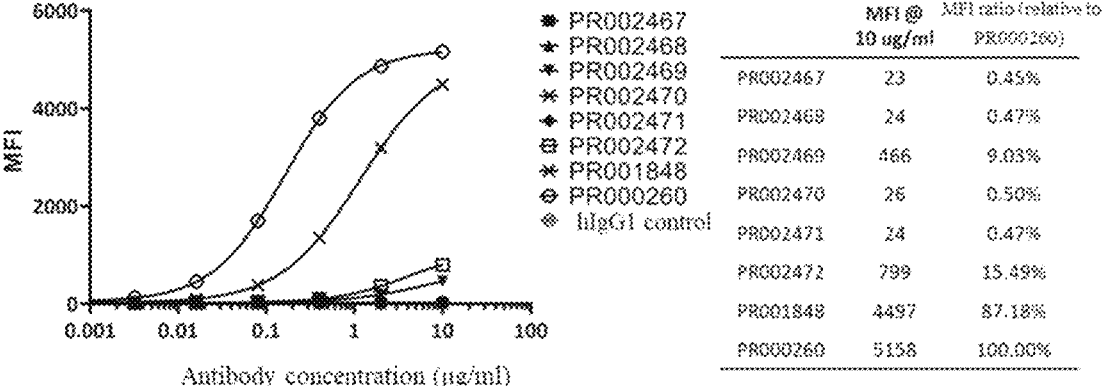
Figure 7D:
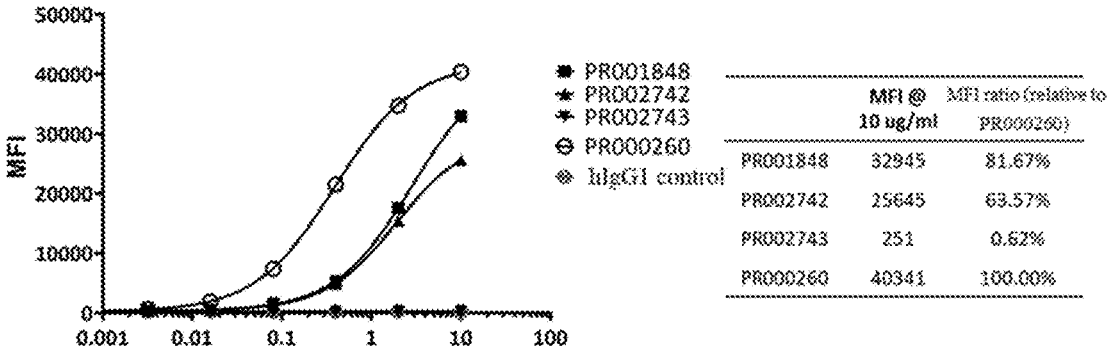
Figure 7E:
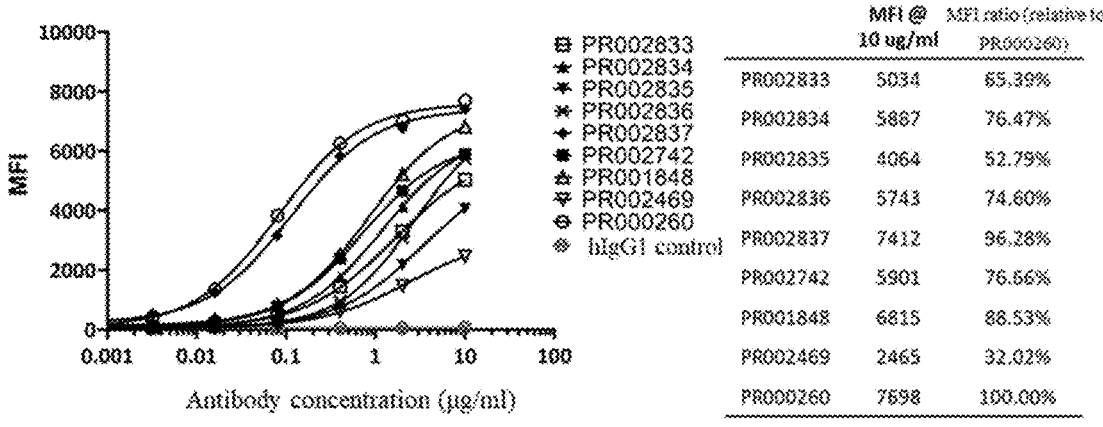
Figure 7F:
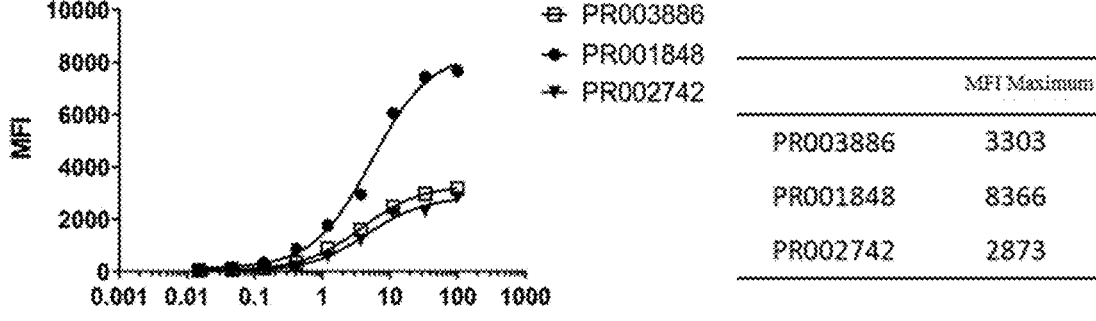
Figure 7G:
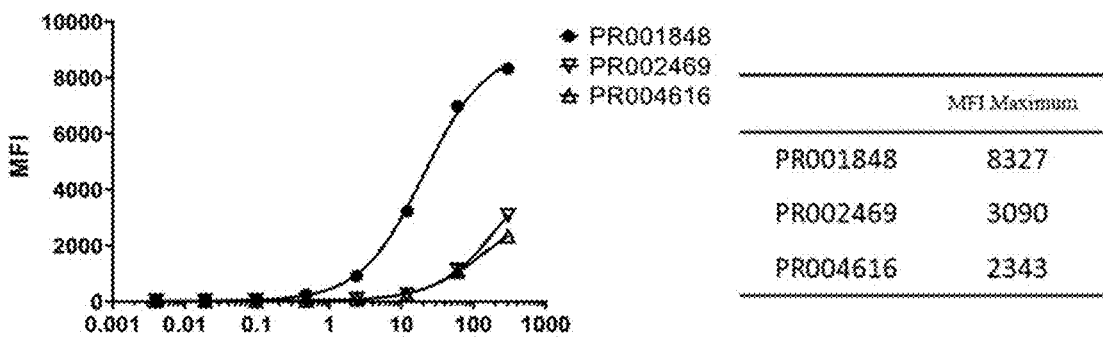

FIG. 6 shows the binding ability of the CD3 antibody obtained in the Example 2 to recombinant CHOK1 cells overexpressing human CD3 (FIG. 6 (A)) and recombinant CHOK1 cells overexpressing cynomolgus monkey CD3 (FIG. 6(B)). The results indicate that the SP34 chimeric antibody PR000260 has a strong binding ability to both human CD3 and cynomolgus monkey CD3.

FIG. 7A to FIG. 7G show the binding ability of the CD3 antibodies obtained in the Example 4.2 (including PR000260 and its mutants) to human pan-T cells, respectively. The fluorescence intensity MFI of the CD3 antibody binding to human pan-T cells and the relative ratio relative to the initial antibody PR000260 were calculated when the antibody concentration was 7.4 or 10 µg/ml. Specifically, after SP34 IgG antibody sequence optimization, PR000512, PR000513, PR001849, and PR002837 have comparable binding ability as PR000260 (i.e., SP34 chimeric antibody); while PR000514 has slightly higher binding ability than PR000260; PR000511, PR001848 PR002469, PR002472, PR002742, PR002833, PR002834, PR002835, PR002836, PR003886, and PR004616 have lower binding ability to T cells; PR002467, PR002468, PR002470, PR002471, and PR002743, on the other hand, barely bind T cells (or the signal cannot be detected at the current antibody concentration). The above results indicate that the present invention has obtained several new antibodies by sequence optimization of the CD3 antibody, which have different binding abilities to human T cells and can be applied to different application scenarios.

Figure 8:
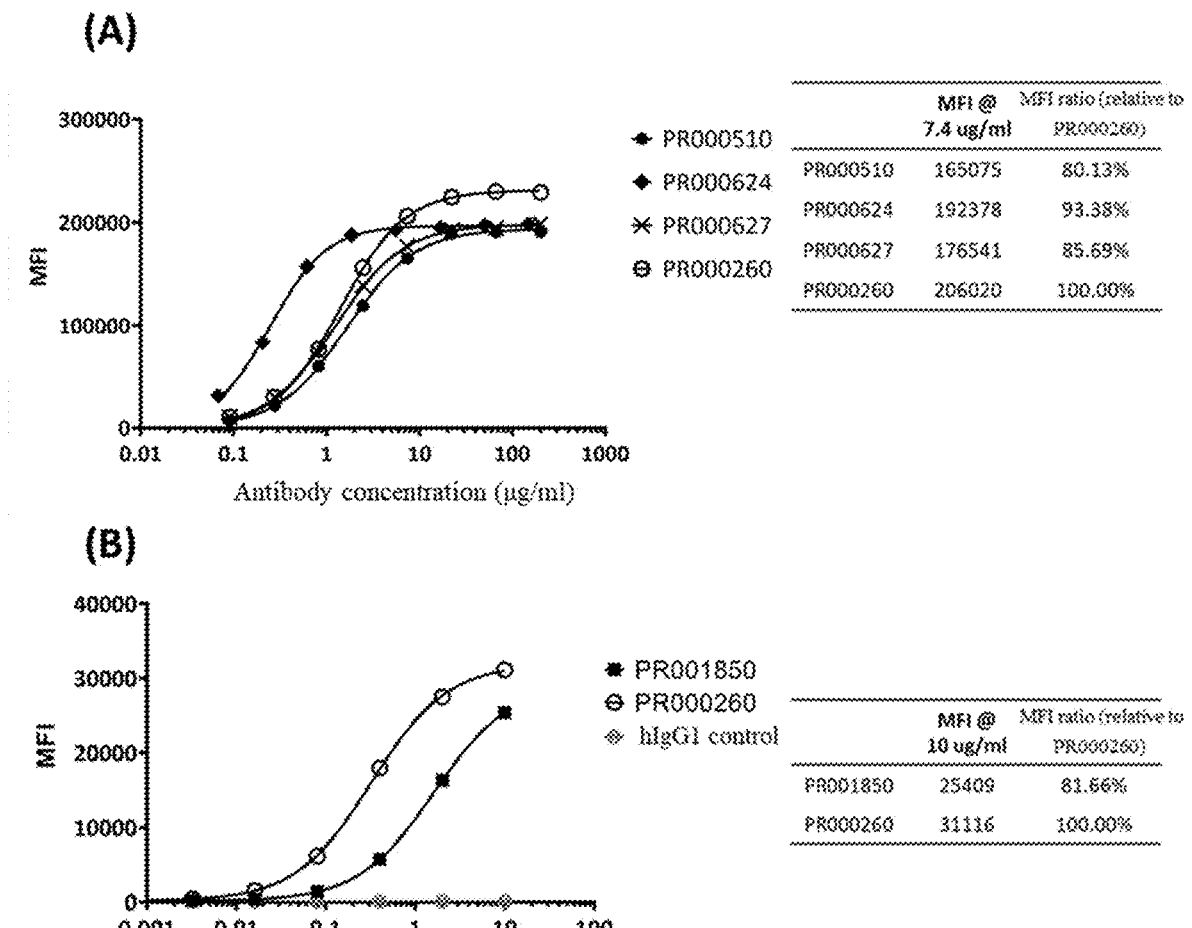
FIG. 8 shows the binding capacity of the CD3 single-chain antibody to human T cells, including the binding curve and MFI relative intensity (fluorescence intensity MFI of the antibody binding to human T cells at specific concentration, and relative ratio compared to the initial antibody PR000260 (SP34)), wherein (A) PR000510, PR000624, PR000627 and PR000260 bind to human T cells, (B) PR001850 and PR000260 bind to human T cells.

FIG. 8 (A) and (B) show the binding capacity of the anti-CD3 scFv-Fc single chain antibody obtained in the Example 4.3 to human pan-T cellsThe fluorescence intensity MFI of the CD3 antibody binding to human pan-T cells and the relative ratio relative to the initial antibody PR000260 were calculated when the antibody concentration was 7.4 or 10 µg/ml. Specifically, after optimization of the humanization of SP34 scFv antibody, PR000624 has a comparable or slightly higher binding capacity than PR000260; PR000510 and PR000627 have a comparable or slightly lower binding capacity than PR000260; and PR001850 has a significantly lower binding capacity to T cells than PR000260. The above results indicate that, the present invention also obtained several stable single-chain antibodies in the form of scFv by sequence optimization of the CD3 antibody, which are able to bind to human T cells and are suitable for application scenarios such as the construction of bispecific antibodies.

Figure 9:
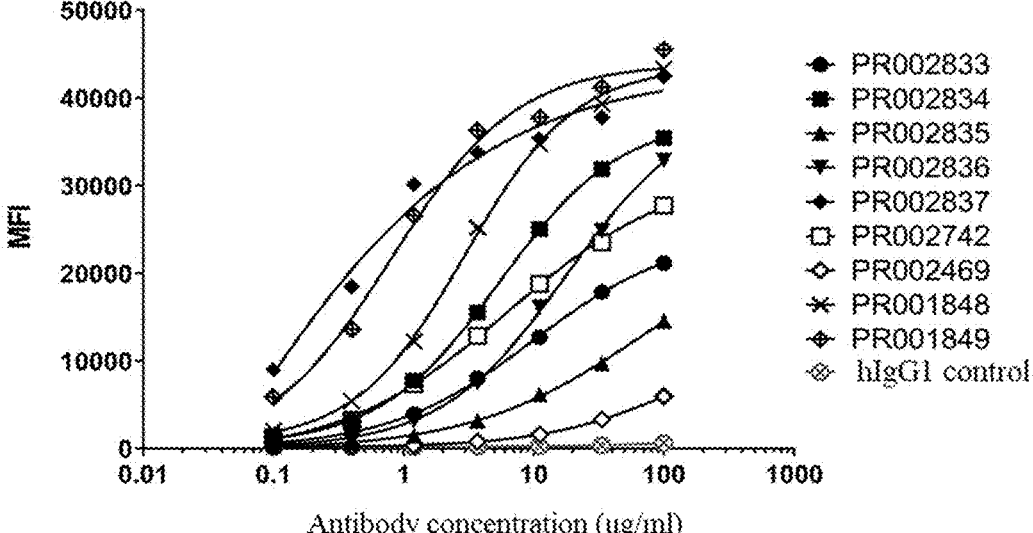
FIG. 9 shows the binding capacity of the CD3 antibody to cynomolgus monkey T cells.

FIG. 9 shows the binding ability of some of the CD3 antibodies obtained in the Example 4.2 to cynomolgus monkey pan-T cells. It can be seen that different molecules have different binding abilities to cynomolgus monkey pan-T cells and are positively correlated with their binding abilities to human pan-T cells; that is, molecules that strongly bind to human pan-T cells also strongly bind to cynomolgus monkey pan-T cells, and vice versa.

Example 6 Determination of Activation of CD3
Antibody on Human T Cells

The gradient dilutions of CD3 antibody (e.g., 50, 10, 5, 1, 0.5, 0.05 µg/ml) were coated in 96 well cell culture plates at three replicate wells per concentration and 50 µl per well, incubating overnight at 4° C. The cell density of human PBMC (MiaoTong Biology) or human pan-T cells (isolated with the human pan-T cell isolation kit (Miltenyi, #130-096-535) from PBMC) was adjusted to $7.5 \times 10^5$/ml, and human CD28 antibody was added at a concentration of 1 µg/ml, thereafter adding 200 µl the resulted mixture per well to the cell culture plate and incubating in $CO_2$ incubator. After 72 hours of incubation, the supernatant was taken and the content of IFN-γ therein was determined using use the IFN-γ ELISA kit (Thermo, #88-7316-77). Used the software GraphPad Prism 8 for data processing and graphical analysis.

Figure 10A:
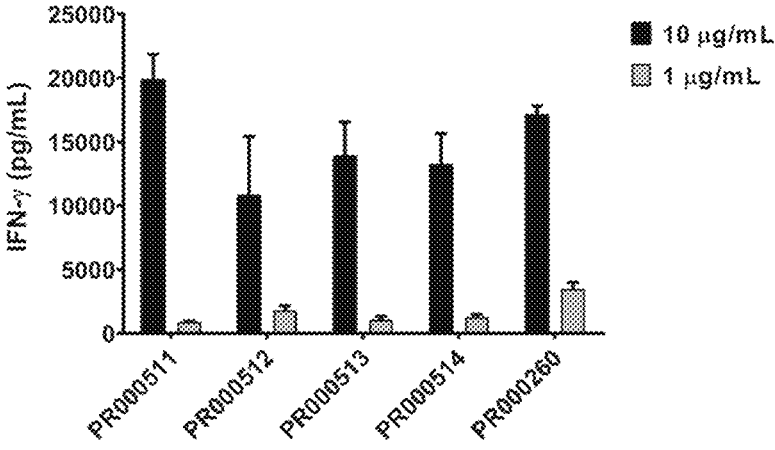
Figure 10B:
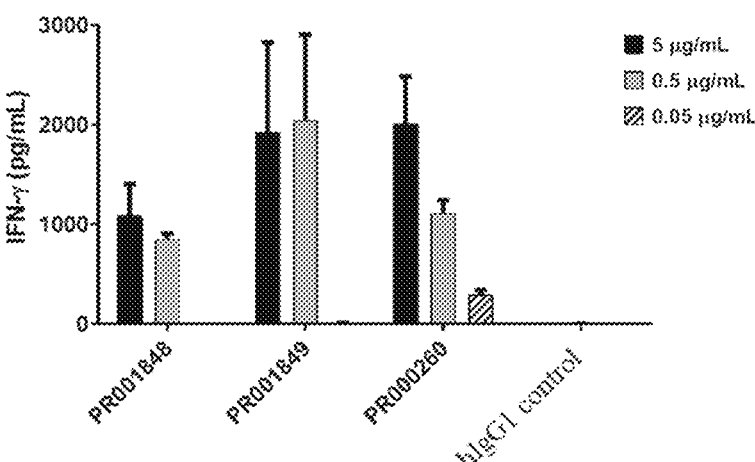
Figure 10C:
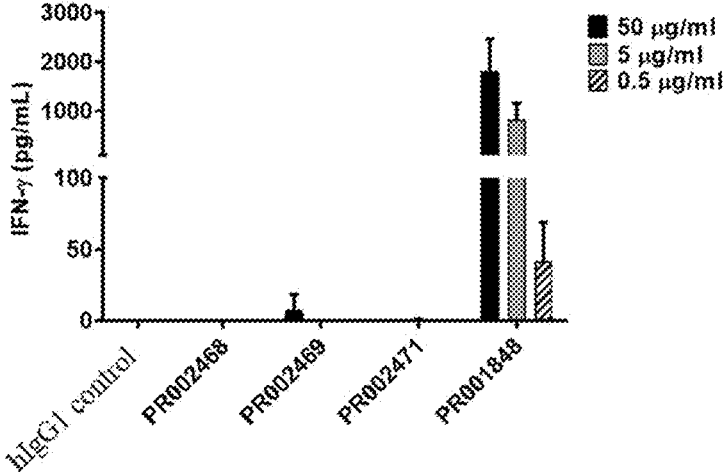
Figure 10D:
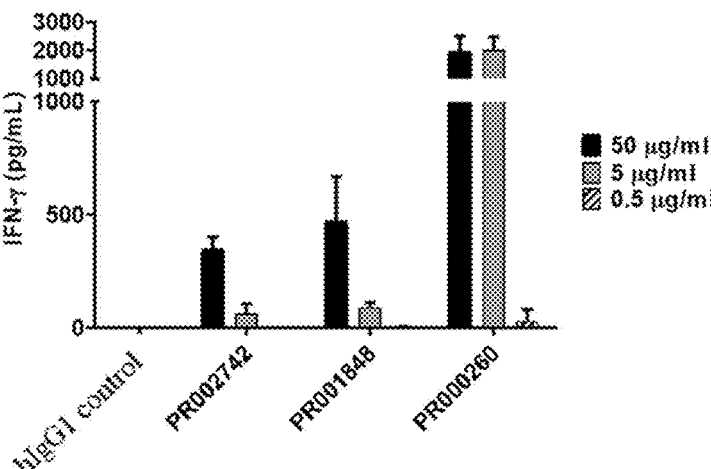
Figure 10E:
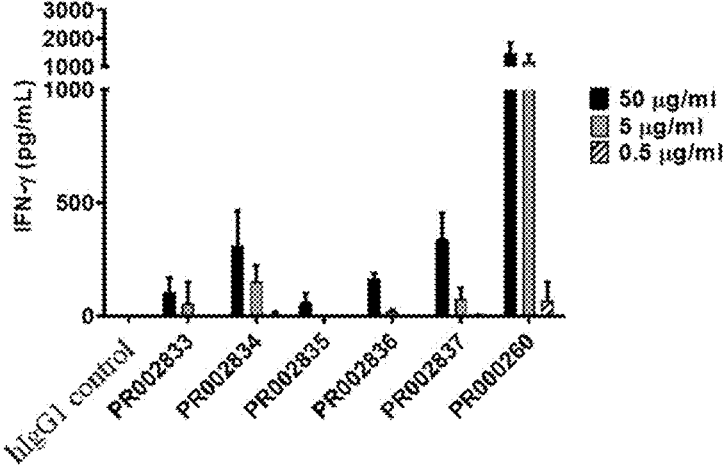
Figure 10F:
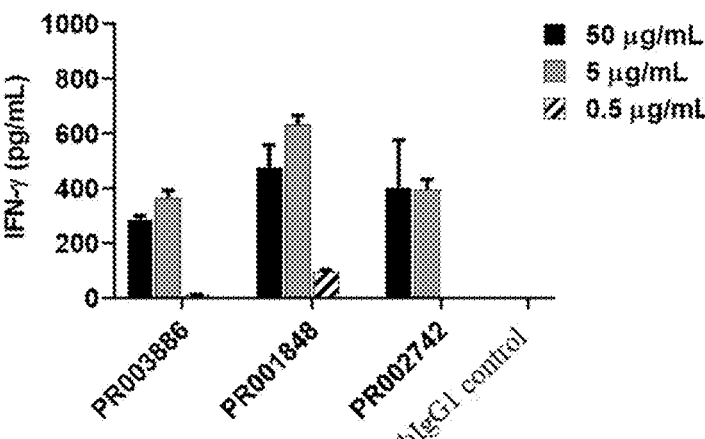
Figure 10G:
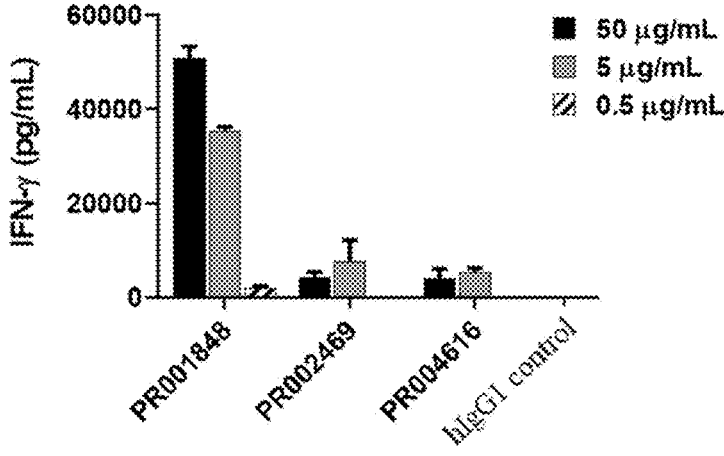

FIG. 10A to FIG. 10G show the ability of each CD3 antibody (including SP34 chimeric antibody) obtained in the Example 4.2 to activate human T cells, respectively. When the antibody concentration is 1 g/mL, PR000511, PR000512, PR000513, and PR000514 produced significantly lower levels of IFN-γ after activating T cells than PR000260; when the antibody concentration is 10 g/mL, PR000512, PR000513, and PR000514 activate slightly lower levels of IFN-γ than PR000260 (FIG. 10A). When the antibody concentration is 0.5 g/mL and 5 g/mL, the level of IFN-γ activated by PR001848 is significantly lower than that of PR000260 (FIG. 10B). In addition, the effect of activating T cells of antibodies PR002468, PR002469, PR002471, PR002742, PR002833, PR002834, PR002835, PR002836, PR002837, PR001848, PR003886 and PR004616 was also detected (FIG. 10C to FIG. 10G), in concentration of 0.5 g/mL, 5 g/mL and 50 g/mL, the results indicated that the level of IFN-γ produced by T cells activated by these antibodies are much lower than those activated by PR000260, wherein, no release of IFN-γ was detected by T cells activated by PR002468 and PR002471, and only weak level of IFN-γ were detected at 50 g/mL of PR002469 and PR002835; the level of IFN-γ produced by T cells activated by PR002742 and PR003886 were comparable and slightly weaker than PR001848; the level of IFN-γ produced by T cells activated by PR002469 and PR004616 were comparable and significantly weaker than PR001848. The above results indicate that the present invention has obtained several new antibodies by sequence optimization of the CD3 antibody, which have different activation abilities on human T cells, and can control different levels of cytokine release and can be applied to different application scenarios.

Figure 11:
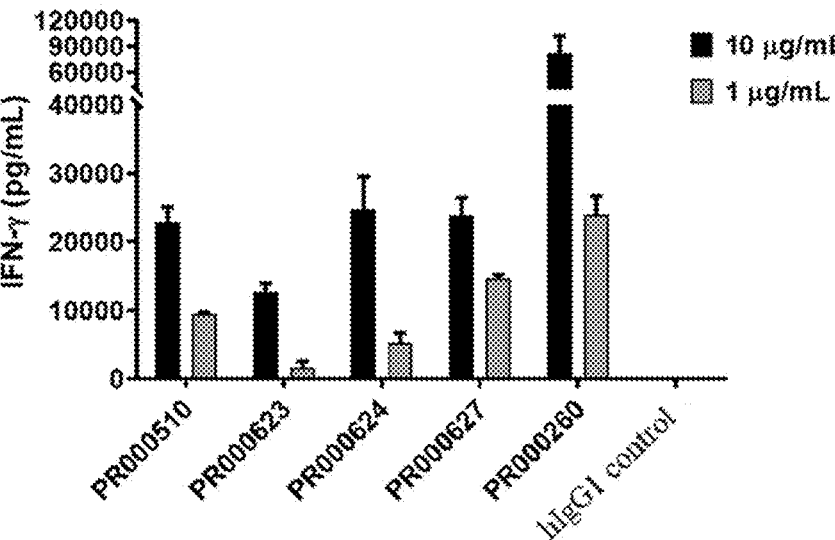
FIG. 11 shows the capacity of the CD3 single-chain antibody (PR000510, PR000623, PR000624, PR000627 and PR000260) to activate human T cells to produce cytokine IFN-γ.

FIG. 11 shows the ability of the anti-CD3 scFv-Fc antibody obtained in the Example 4.3 to activate human T cells. PR000510, PR000623, PR000624, and PR000627 at concentrations of 1 g/mL and 10 g/mL all exhibited lower levels of IFN-γ than PR000260 but higher than the isotype control antibody, indicating that these four molecules limited the release of cytokines by regulating the activation levels of T cells. The above results indicate that the present invention also obtained several stable single-chain antibodies in the form of scFv by sequence optimization of the CD3 antibody, which have weaker activation on human T cells showing lower levels of cytokine release, and are suitable for application scenarios such as the construction of bispecific antibodies.

Example 7 Bispecific Antibody Targeting B7H4 Containing Anti-CD3 scFv Antibody B7H4, a member of the B7 family of transmembrane proteins, is highly expressed in a variety of solid tumor tissues such as breast, ovarian and endometrial cancers, while it is not expressed or very faintly expressed in normal tissues, making B7H4 a very specific tumor-associated target antigen. A bispecific antibody molecule targeting both B7H4 and CD3 were constructed, which can selectively activate T cells near tumor cells by targeting and binding to B7H4 on the surface of tumor cells, thus providing specific killing of tumor cells.

7.1 Preparation of B7H4 Antibody

The sequence of the variable region of the B7H4 antibody can be derived from WO2016040724, and the recombinant IgG antibody PR000014 target B7H4 was constructed according to the methods of the Example 1.1. The following Table 10 lists the sequence information of the B7H4 antibody PR000014.

TABLE 10

| Sequence information of light chain and heavy chain of B7H4 antibody PR000014 | | | |
|---|---|---|---|
| Antibody number | Target | Heavy chain SEQ ID NO: | Light chain SEQ ID NO: |
| PR000014 | B7H4 | 82 | 83 |

Figure 16:
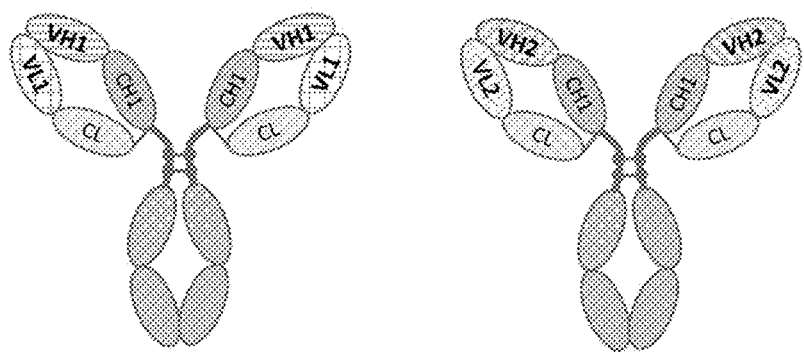
FIG. 16 shows the structure of the monoclonal antibody or the bispecific antibody; (A) IgG structure, (B) asymmetric "four chain" structure, (C) asymmetric "three chain" structure containing the single chain antibody.
Figure 16:
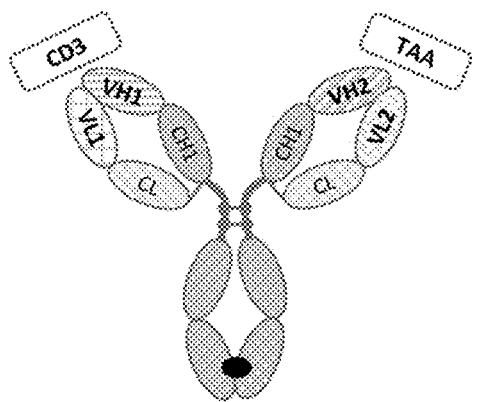
Figure 16:
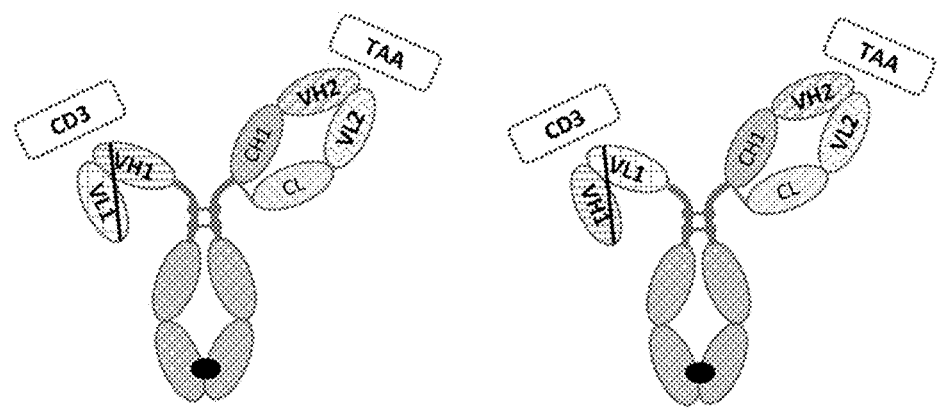

7.2 Preparation of Bispecific Antibody Targeting B7H4 Containing Anti-CD3 scFv Antibody Using the sequence of the B7H4 antibody PR000014 obtained in the Example 7.1 and the sequence of the CD3 single chain antibody PR000627 obtained in the Example 4.3 to construct the bispecific antibody molecule PR002883 targeting B7H4×CD3, which contains three polypeptide chains: a heavy chain containing the CD3 single chain antibody scFv (SEQ ID NO: 88), a heavy chain containing the VH of B7H4 antibody (SEQ ID NO: 86), and a light chain containing the VL of B7H4 antibody (SEQ ID NO: 83). The structure is shown in FIG. 16(C). Since the molecule has a special asymmetric structure, different amino acid mutations were introduced in the constant regions of the two heavy chains in order to reduce the generation of homologous heavy chain dimers. At the same time, the "LALAPG" triple mutation (L234A/L235A/P329G) was introduced in the constant region of the heavy chain to prevent cross-linking and reduce effector function caused by Fcγ receptor binding.

Recombinant protein of the bispecific antibody PR002883 was prepared by using the method described in the Example 1.1 in combination with plasmids in ratio (e.g., 1:1:1 or other ratios), and the follow-up one-step affinity purification. The sequence of bispecific antibody PR002883 is listed in Table 11; the expression of the bispecific antibody is listed in Table 12.

TABLE 11

| Chains of the bispecific antibody and the corresponding sequence information | | | | | |
|---|---|---|---|---|---|
| Bispecific antibodies | Anti-B7H4 antibody | Anti-CD3 scFv | Heavy Chain 1 SEQ ID NO: | Heavy Chain 2 SEQ ID NO: | Light chain SEQ ID NO: |
| PR002883 | PR000014 | PR000627 | 88 | 86 | 83 |

TABLE 12

| Expression of the bispecific antibody | | |
|---|---|---|
| Bispecific antibody | Yield in HEK293 (mg/L) | SDS-PAGE purity (%) |
| PR002883 | 94.0 | 70 |

Figure 12:
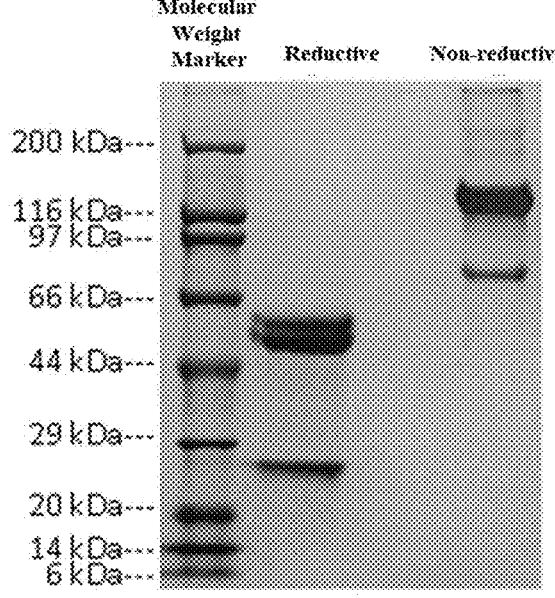
FIG. 12 shows the SDS-PAGE results of samples of the bispecific antibody (A) PR002883 and (B) PR002885 obtained one-step purification.
Figure 12:
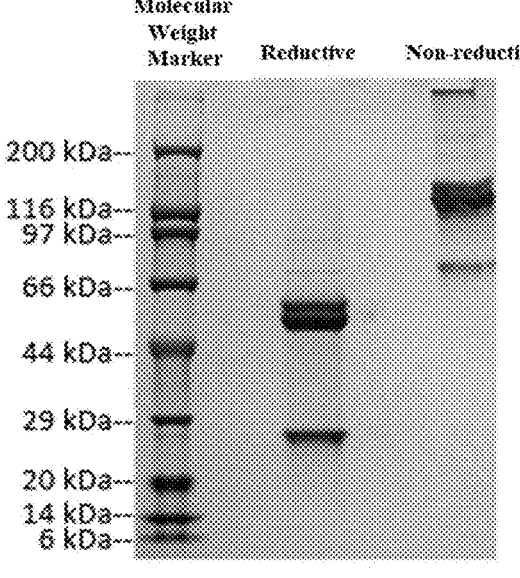

FIG. 12(A) shows the results of the bispecific antibody PR002883 after one-step purification by SDS-PAGE analysis. It shows that its main by-products are incompletely assembled molecules with few high polymer components, which can be reduced by optimizing the purification step or by optimizing the plasmid transfection ratio.

7.3 Binding to Tumor Cells Expressing B7H4

This Example investigates the ability of the bispecific antibody binding tumor cell SK-BR-3 (ATCC, HTB-30)

expressing human B7H4. Specifically, collected cell SK-BR-3 suspension, adjusted the cell density to $1\times10^6$/ml, and inoculated them at 100 μl/well in a 96 well V-bottom plate (Corning, #3894); subsequently, the antibody to be tested with a concentration 2-fold of final concentration obtained by 3-fold gradient dilution was added at volume of 100 μl/well. Cells were incubated at 4° C. in the dark for 2 hours. Afterwards, the cells were rinsed twice with 100 μl/well of pre-chilled PBS, centrifuged at 500 g, 4° C. for 5 minutes. The supernatant was discarded. Then added 100 μl/well of secondary antibody Alexa Fluor 488 AffiniPure Goat Anti-Human IgG, Fcγ fragment specific (Jackson ImmunoResearch, #109-545-098), and incubated the cells from light at 4° C. in the dark for 1 hour. Then the cells were rinsed twice with 100 μl/well of pre-chilled PBS, centrifuged at 500 g, for 5 minutes. The supernatant was discarded. Finally, the cells were resuspended with 200 L/well of pre-chilled PBS. The fluorescent luminescence signal value were read by flow cytometry (BD FACS CANTOII or ACEA NovoCyte), and the resulted data were processed and analyzed by software FlowJo v10 (FlowJo, LLC). The software GraphPad Prism 8 was used for data processing and graphical analysis, and parameters such as binding curves and EC50 values can be obtained by four-parameter nonlinear fitting.

FIG. 13(A) shows the binding ability of the monoclonal antibody obtained in the Example 7.1 and the bispecific antibody obtained in the Example 7.2 to cell SK-BR-3. It can be seen that the bispecific antibody PR002883 has a comparable or even better binding capacity compared to the monoclonal antibody PR000014.

7.4 Binding to Human T Cells

Figure 13:
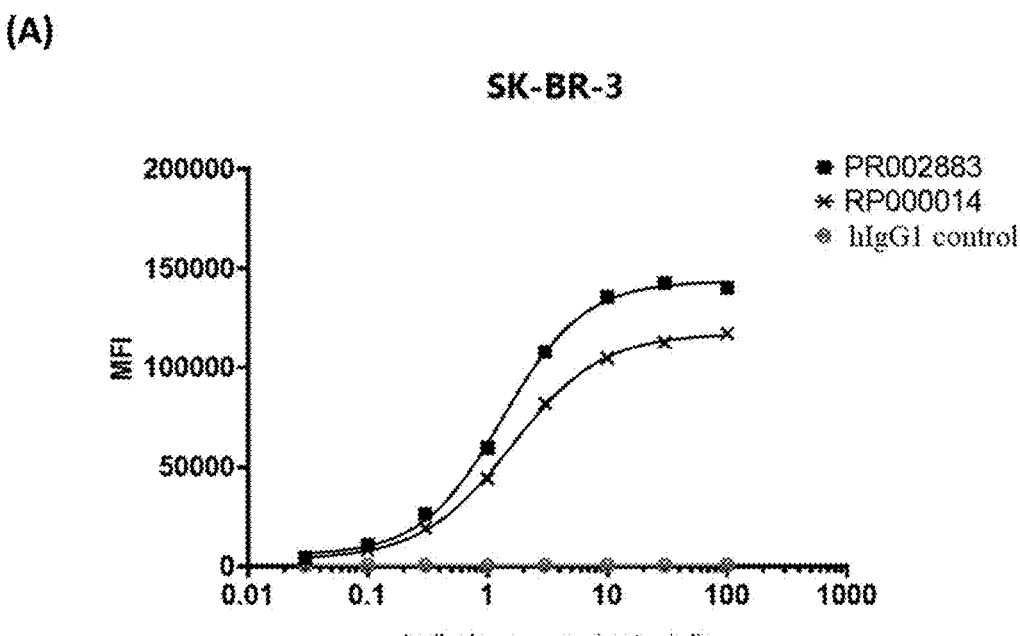
FIG. 13 shows the binding capacity of the monoclonal antibody and the bispecific antibody to (A) SK-BR-3 cells and (B) human T cells.
Figure 13:
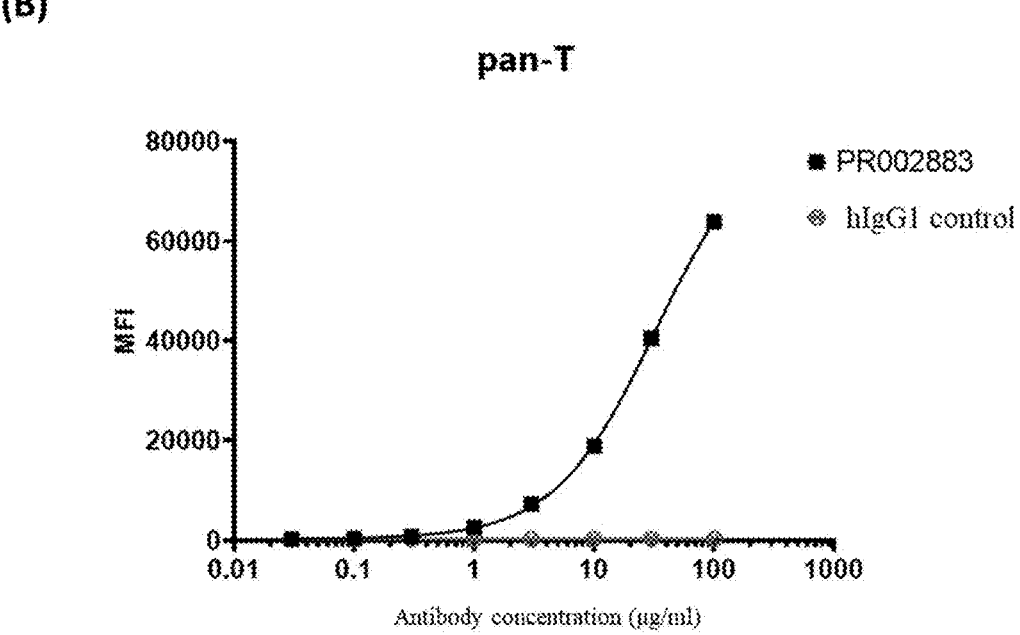

The ability of the bispecific antibody PR002883 binding to human pan-T cells was detected by the method described in the Example 5. As shown in FIG. 13 (B), PR002883 is able to bind to human pan-T cells.

7.5 Killing and Cytokine Releasing Effect of the Bispecific Antibody on B7H4 High-Expressing Cell Line SK-BR-3 In Vitro To investigate the ability of killing target cell mediated by B7H4×CD3 bispecific antibody in vitro, human PBMC was used as effector cells, and B7H4 high-express cell line SK-BR-3 (ATCC, HTB-30) was used as target cells for killing assays in vitro and cytokine release detection. Specifically, 50 μL of RPMI1640/10% FBS medium was added to each well of E-plate (ACEA Biosciences Inc., #05232368001), thereafter balancing in incubator containing 5% $CO_2$ at 37° C. for 30 minutes, and then the E-plate was placed in the instrument xCELLigence RTCA (ACEA Biosciences) to test for normality. The density of SK-BR-3 was adjusted to $0.4\times10^6$ cells/mL with RPMI1640/10% FBS medium, then inoculated into E-plate at 50 μL cells/well, and then the E-plate was placed on xCELLigence RTCA overnight to detect the cell index. The density of PBMC was adjusted to $4\times10^6$ cells/mL with RPMI1640/10% FBS medium, and inoculated into E-plate at 50 μL cells/well, then the antibody to be tested with a concentration 4-flod of final concentration obtained by 5-fold gradient dilution was added at 50 μL/well, wherein the highest final concentration of the antibody was 0.2 nM, and there were 7 concentrations for each antibody, the final ratio of effector cells to target cells was 10:1, with two replicates set up. Meanwhile, blank control was set up in the plate: SKBR3+PBMC+RPMI1640/10% FBS medium; the E-plate was incubated in 37° C., incubator containing 5% $CO_2$ for 24 hours. After incubation, the E-plate was placed on the xCELLigence RTCA instrument to detect the cell index.

The specific killing effect of the antibody was calculated by applying the assayed cell index to the following formula:

$$\text{Cell Killing }\% = (1-\text{Test Sample/Blank Control}) * 100\%.$$

The supernatant of cell culture was collected for detecting the release of cytokine IFN-γ. Refer to the operation instructions of IFN-γ kit (IFN gamma Human Uncoated ELISA Kit, Thermo, #88-7316-77) for ELISA detection.

Figure 14:
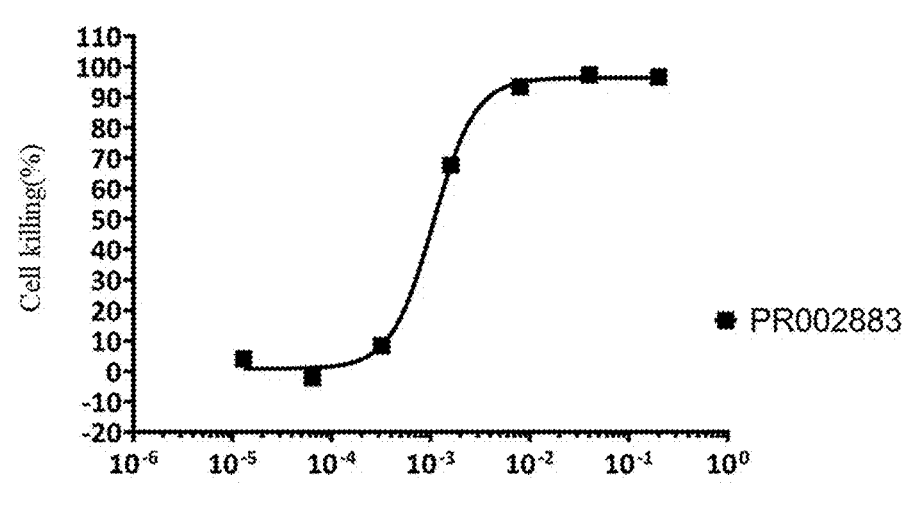
FIG. 14 shows the target cell killing capacity mediated by the bispecific antibody PR002883 in vitro; wherein, (A) shows SK-BR-3 cell killing and (B) shows IFN-γ release levels.
Figure 14:
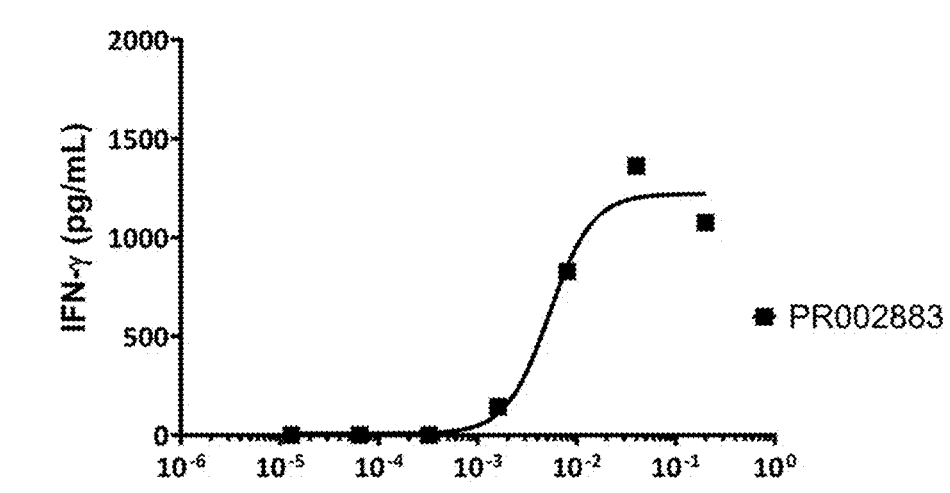

As shown in FIG. 14 (A) and (B), the bispecific antibody PR002883 can activate T cells to release cytokines such as IFN-γ and kill tumor cell SK-BR-3 effectively. Almost 100% of tumor cells were killed when the concentration of the bispecific antibody was at 0.01 μg/ml (FIG. 14(A)).

Example 8 Bispecific Antibody Targeting ROR1 Containing Anti-CD3 scFv Antibody ROR1 is an inactive tyrosine protein kinase transmembrane protein that is overexpressed in many tumors but virtually not expressed in normal tissues. ROR1 contributes to cell proliferation and migration in chronic lymphocytic leukemia by transducing the Wnt signaling pathway after interacting with Wnt5a as a receptor, and contributes to epithelial-mesenchymal-transformation (EMT) in solid tumors. The tumor-specific expression of ROR1 makes it a suitable tumor-associated antigen target for the development of therapeutic agents. The construction of a bispecific antibody molecule targeting both ROR1 and CD3 can selectively activate T cells near tumor cells by targeting and binding to ROR1 on the surface of tumor cells, thus providing specific killing of tumor cells.

8.1 Preparation of ROR1 Antibody

The sequence of the variable region of the ROR1 antibody can be derived from WO2016094873, and construct the recombinant IgG antibody PR000374 targeting ROR1 according to the methods of the Example 1.1. The following Table 13 lists the sequence information of the ROR1 antibody PR000374.

TABLE 13

| Sequence list of the ROR1 antibody PR000374. | | | |
|---|---|---|---|
| Antibody number | Target | Heavy chain SEQ ID NO: | Light chain SEQ ID NO: |
| PR000374 | ROR1 | 84 | 85 |

8.2 Preparation of Bispecific Antibody Targeting ROR1 Containing Anti-CD3 scFv Antibody Construction of the bispecific antibody molecule PR002885 targeting ROR1×CD3 was performed by using the sequence of the ROR1 antibody PR000374 obtained in the Example 8.1 and the sequence of the CD3 single chain antibody PR000627 obtained in the Example 4.3, which contains three polypeptide chains: a heavy chain containing the CD3 single chain antibody scFv (SEQ ID NO: 88), a heavy chain containing the ROR1 antibody VH (SEQ ID NO: 87), and a light chain containing the ROR1 antibody VL (SEQ ID NO: 85). The structure is shown in FIG. 16(C).

Since the molecule has a special asymmetric structure, different amino acid mutations were introduced into the constant regions of the two heavy chains in order to reduce the generation of homologous heavy chain dimers. At the same time, the "LALAPG" triple mutation (L234A/L235A/ P329G) was introduced into the constant region of the heavy chain to prevent cross-linking and reduce effector function caused by Fcγ receptor binding.

Recombinant protein of the bispecific antibody PR002885 was prepared by using the method described in the Example 1.1 in combination with plasmids ratio (e.g., 1:1:1 or other ratios), and the follow-up one-step affinity purification. The sequence of bispecific antibody PR002885 is listed in Table 14; the expression of the bispecific antibody is listed in Table 15.

TABLE 14

Chains of the bispecific antibody and the corresponding sequence number

| Bispecific antibody | Anti-ROR1 antibody | Anti-CD3 scFv | Heavy chain1 SEQ ID NO: | Heavy chain2 SEQ ID NO: | Light chain SEQ ID NO: |
|---|---|---|---|---|---|
| PR002885 | PR000374 | PR000627 | 88 | 87 | 85 |

TABLE 15

Expression of the bi specific antibody

| Bispecific antibody | Yield in HEK293 (mg/L) | SDS-PAGE purity (%) |
|---|---|---|
| PR002885 | 90.0 | 70 |

FIG. 12(B) shows the results of the bispecific antibody PR002885 after one-step purification by SDS-PAGE analysis. It shows that its main by-products are incompletely assembled molecules with few high polymer components, which can be reduced by optimizing the purification step or by optimizing the plasmid transfection ratio.

8.3 Binding to Tumor Cells Expressing ROR1

This Example investigates the ability of the bispecific antibody binding tumor cell Panc-1(ATCC, CRL-1469) expressing human ROR1. Specifically, collected cell Panc-1 suspension, adjusted the cell density to $1\times10^6$/ml, and inoculated them at 100 μl/well in a 96 well V-bottom plate (Corning, #3894); subsequently, the antibody to be tested with a concentration 2-flod of final concentration obtained by 3-fold gradient dilution was added at volume of 100 μl/well. Cells were incubated at 4° C. in the dark for 2 hours. Afterwards, the cells were rinsed twice with 100 μl/well of pre-chilled PBS, centrifuged at 500 g, 4° C. for 5 minutes. The supernatant was discarded. Then added 100 μl/well of fluorescent secondary antibody Alexa Fluor 488 AffiniPure Goat Anti-Human IgG, Fcγ fragment specific (Jackson ImmunoResearch, #109-545-098), and incubated the cells from light at 4° C. in the dark for 1 hour. Then the cells were rinsed twice with 100 μl/well of pre-chilled PBS, centrifuged at 500 g, for 5 minutes. The supernatant was discarded. Finally, the cells were resuspended with 200 μL/well of pre-chilled PBS. The fluorescent luminescence signal value were read by flow cytometry (BD FACS CANTOII or ACEA NovoCyte), and the resulted data were processed and analyzed by software FlowJo v10 (FlowJo, LLC). The software GraphPad Prism 8 was used for data processing and graphical analysis, and parameters such as binding curves and EC50 values can be obtained by four-parameter nonlinear fitting.

FIG. 15(A) shows the binding ability of the monoclonal antibody obtained in the Example 8.1 and the bispecific antibody obtained in the Example 8.2 to cell Panc-1. It can be seen that both the bispecific antibody PR002885 and the monoclonal antibody PR000374 can bind Panc-1.

8.4 Binding to Human T Cells

Figure 15:
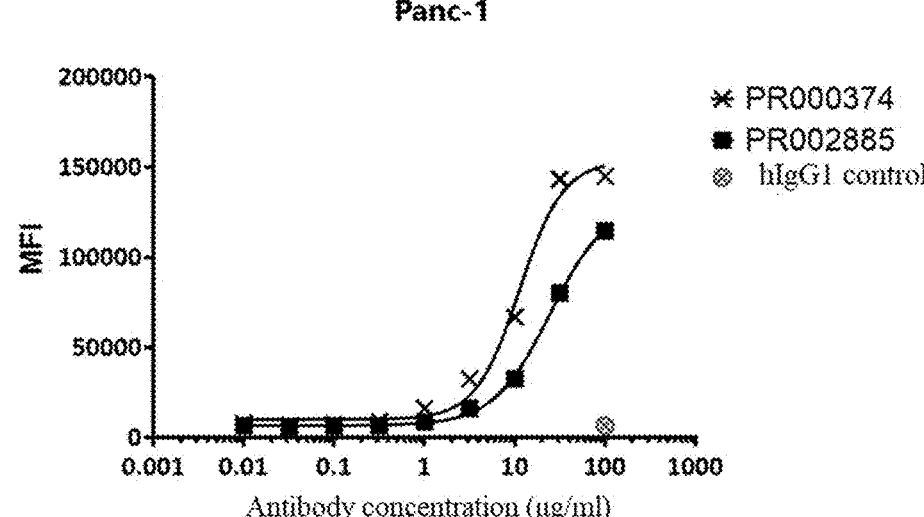
FIG. 15 shows the binding capacity of the monoclonal antibody and the bispecific antibody to (A) Panc-1 cells and (B) human T cells.
Figure 15:
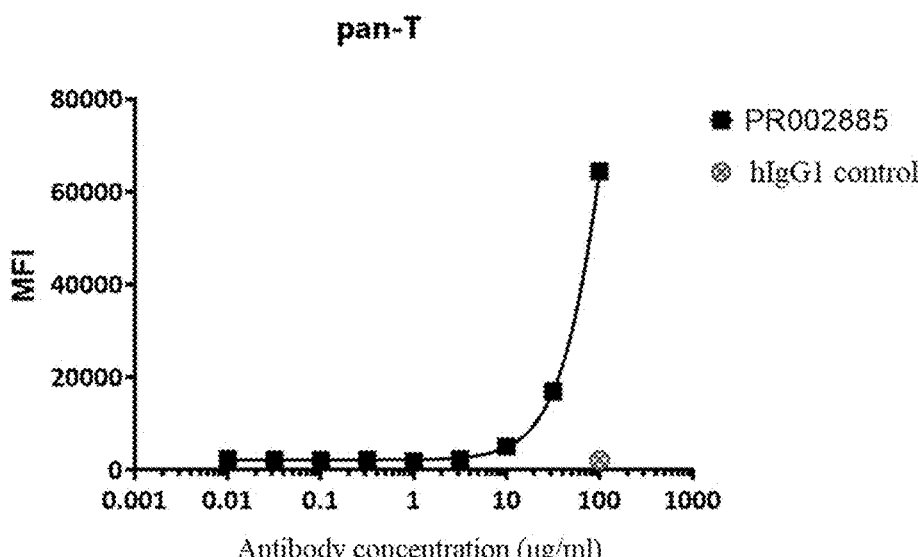

The ability of the bispecific antibody PR002885 binding to human pan-T cells was detected by the method described in the Example 5. As shown in FIG. 15 (B), PR002885 is able to bind to human pan-T cells.

---

What is claimed is:

1. A CD3-targeting antibody, comprising a light chain variable region (VL) and a heavy chain variable region (VH), wherein, the amino acid sequence of the VH is set forth in SEQ ID NO: 44, and the amino acid sequence of the VL is set forth in SEQ ID NO: 58; or, the amino acid sequence of the VH is set forth in SEQ ID NO: 51, and the amino acid sequence of the VL is set forth in SEQ ID NO: 58; or, the amino acid sequence of the VH is set forth in SEQ ID NO: 45, and the amino acid sequence of the VL is set forth in SEQ ID NO: 58; or, the amino acid sequence of the VH is set forth in SEQ ID NO: 52, and the amino acid sequence of the VL is set forth in SEQ ID NO: 58; or, the amino acid sequence of the VH is set forth in SEQ ID NO: 43, and the amino acid sequence of the VL is set forth in SEQ ID NO: 58; or, the amino acid sequence of the VH is set forth in SEQ ID NO: 50, and the amino acid sequence of the VL is set forth in SEQ ID NO: 58; or, the amino acid sequence of the VH is set forth in SEQ ID NO: 47, and the amino acid sequence of the VL is set forth in SEQ ID NO: 58; or, the amino acid sequence of the VH is set forth in SEQ ID NO: 48, and the amino acid sequence of the VL is set forth in SEQ ID NO: 58; or, the amino acid sequence of the VH is set forth in SEQ ID NO: 49, and the amino acid sequence of the VL is set forth in SEQ ID NO: 58; or, the amino acid sequence of the VH is set forth in SEQ ID NO: 53, and the amino acid sequence of the VL is set forth in SEQ ID NO: 58; or, the amino acid sequence of the VH is set forth in SEQ ID NO: 54, and the amino acid sequence of the VL is set forth in SEQ ID NO: 58; or, the amino acid sequence of the VH is set forth in SEQ ID NO: 55, and the amino acid sequence of the VL is set forth in SEQ ID NO: 58; or, the amino acid sequence of the VH is set forth in SEQ ID NO: 46 and the amino acid sequence of the VL is set forth in SEQ ID NO: 58.

2. The CD3-targeting antibody of claim 1, wherein the antibody comprises a single chain antibody (scFv) of VL linker-VH or VH-linker-VL.

3. The CD3-targeting antibody of claim 1, wherein the antibody further comprises a constant region.

4. A bispecific antibody, comprising a first protein functional region and a second protein functional region, wherein the first protein functional region comprises the CD3-targeting antibody of claim 1, and the second protein functional region is a ROR1 targeting antibody.

5. The bispecific antibody of claim 4, wherein the bispecific antibody comprises the following three chains: (1) VL1-linker-VH1-Hinge-CH2-CH3 (knob) or VH1-linker-VL1-Hinge-CH2-CH3 (knob) of the first protein functional region, (2) VH2-CH1-Hinge-CH2-CH3 (hole) of the second protein functional region, and (3) VL2-CL of the second protein functional region; the second protein functional region is a non-CD3-targeting antibody.

6. The bispecific antibody of claim 5, wherein the bispecific antibody comprises VL1-linker-VH1-Hinge-CH2-CH3 (knob) as shown in SEQ ID NO: 88, VH2-CH1-Hinge-CH2-CH3 (hole) as shown in SEQ ID NO: 87, and VL2-CL as shown in SEQ ID NO: 85.

7. An isolated nucleic acid, encoding the CD3-targeting antibody of claim 1 or a bispecific antibody comprising a first protein functional region and a second protein functional region, wherein the first protein functional region comprises the CD3-targeting antibody, and the second protein functional region is a ROR1 targeting antibody.

8. An expression vector, comprising the isolated nucleic acid of claim 7.

9. A genetically modified cell, transfected with the expression vector of claim 8.

10. A pharmaceutical composition, comprising the CD3-targeting antibody of claim 1, a bispecific antibody, and a pharmaceutically acceptable carrier;

wherein the bispecific antibody comprises a first protein functional region and a second protein functional region, wherein the first protein functional region comprises the CD3-targeting antibody, and the second protein functional region is a ROR1 targeting antibody.

11. A method for treating a patient in need of a medicament for tumor, comprising administering to the patient a medicament comprising an effective amount of the CD3-targeting antibody of claim 1, a bispecific antibody or a pharmaceutical composition;

wherein the bispecific antibody comprises a first protein functional region and a second protein functional region, wherein the first protein functional region comprises the CD3-targeting antibody, and the second protein functional region is a ROR1 targeting antibody;

wherein the pharmaceutical composition comprises the CD3-targeting antibody, the bispecific antibody and a pharmaceutically acceptable carrier.

12. The CD3-targeting antibody of claim 2, wherein the linker is $(G_4S)_n$ or a variant thereof, wherein n is a non-zero natural number.

13. The CD3-targeting antibody of claim 12, wherein the amino acid sequence of the scFv is set forth in SEQ ID NO: 73, SEQ ID NO: 78, SEQ ID NO: 79 or SEQ ID NO: 80.

14. The CD3-targeting antibody of claim 13, wherein the antibody further comprises the Fc, wherein the Fc is linked to the scFv by a hinge.

15. The CD3-targeting antibody of claim 3, wherein the constant region is a human constant region comprising a human light chain constant region and a human heavy chain constant region.

16. The CD3-targeting antibody of claim 15, wherein the human heavy chain constant region is from hIgG1, hIgG2, hIgG3, hIgG4, or a variant thereof.

17. The bispecific antibody of claim 5, wherein the linker is $(G_4S)_n$, and n is a non-zero natural number of 1 to 20.

18. The CD3-targeting antibody of claim 16, wherein the human heavy chain constant region is a heavy chain constant region as shown in SEQ ID NO: 63 or SEQ ID NO: 64.

\* \* \* \* \*

SEQUENCE LISTING

<160> NUMBER OF SEQ ID NOS: 92

<210> SEQ ID NO 1
<211> LENGTH: 7
<212> TYPE: PRT
<213> ORGANISM: Artificial Sequence
<220> FEATURE:
<223> OTHER INFORMATION: SP34_VH|HCDR1|Chothia; VH3230|HCDR1|Chothia;
     VH3231|HCDR1|Chothia; VH3

<400> SEQUENCE: 1

Gly Phe Thr Phe Asn Thr Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: VH3232|HCDR1|Chothia; VH3233|HCDR1|Chothia;
     VH3234|HCDR1|Chothia; VH32

<400> SEQUENCE: 2

```
Gly Phe Thr Phe Ser Thr Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: SP34_VH|HCDR2|Chothia; VH3230|HCDR2|Chothia;
      VH3231|HCDR2|Chothia; VH3

<400> SEQUENCE: 3

Arg Ser Lys Tyr Asn Asn Tyr Ala
1               5

<210> SEQ ID NO 4
<211> LENGTH: 14
<212> TYPE: PRT
<213> ORGANISM: Artificial Sequence
<220> FEATURE:
<223> OTHER INFORMATION: SP34_VH|HCDR3|Chothia; VH3230|HCDR3|Chothia;
      VH3231|HCDR3|Chothia; VH3

<400> SEQUENCE: 4

His Gly Asn Phe Gly Asn Ser Tyr Val Ser Trp Phe Ala Tyr
1               5                   10

<210> SEQ ID NO 5
<211> LENGTH: 25
<212> TYPE: PRT
<213> ORGANISM: Artificial Sequence
<220> FEATURE:
<223> OTHER INFORMATION: SP34_VH|HFWR1|Chothia

<400> SEQUENCE: 5

Glu Val Gln Leu Val Glu Ser Gly Gly Gly Leu Val Gln Pro Lys Gly
1               5                   10                  15

Ser Leu Lys Leu Ser Cys Ala Ala Ser
            20                  25

<210> SEQ ID NO 6
<211> LENGTH: 25
<212> TYPE: PRT
<213> ORGANISM: Artificial Sequence
<220> FEATURE:
<223> OTHER INFORMATION: VH3230|HFWR1|Chothia; VH3231|HFWR1|Chothia;
      VH3232|HFWR1|Chothia; VH32

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 7
<211> LENGTH: 25
<212> TYPE: PRT
<213> ORGANISM: Artificial Sequence
<220> FEATURE:
<223> OTHER INFORMATION: VH3730|HFWR1|Chothia; VH3731|HFWR1|Chothia;
      VH3732|HFWR1|Chothia; VH37

<400> SEQUENCE: 7

Glu Val Gln Leu Val Glu Ser Gly Gly Gly Leu Val Gln Pro Gly Gly
1               5                   10                  15
```

-continued

```
Ser Leu Lys Leu Ser Cys Ala Ala Ser
            20                  25

<210> SEQ ID NO 8
<211> LENGTH: 19
<212> TYPE: PRT
<213> ORGANISM: Artificial Sequence
<220> FEATURE:
<223> OTHER INFORMATION: SP34_VH|HFWR2|Chothia

<400> SEQUENCE: 8

Ala Met Asn Trp Val Arg Gln Ala Pro Gly Lys Gly Leu Glu Trp Val
1               5                   10                  15

Ala Arg Ile

<210> SEQ ID NO 9
<211> LENGTH: 19
<212> TYPE: PRT
<213> ORGANISM: Artificial Sequence
<220> FEATURE:
<223> OTHER INFORMATION: VH3230|HFWR2|Chothia; VH3231|HFWR2|Chothia;
      VH3232|HFWR2|Chothia; VH32

<400> SEQUENCE: 9

Ala Met Asn Trp Val Arg Gln Ala Pro Gly Lys Gly Leu Glu Trp Val
1               5                   10                  15

Ser Arg Ile

<210> SEQ ID NO 10
<211> LENGTH: 19
<212> TYPE: PRT
<213> ORGANISM: Artificial Sequence
<220> FEATURE:
<223> OTHER INFORMATION: VH3730|HFWR2|Chothia; VH3731|HFWR2|Chothia;
      VH3732|HFWR2|Chothia; VH37

<400> SEQUENCE: 10

Ala Met Asn Trp Val Arg Gln Ala Ser Gly Lys Gly Leu Glu Trp Val
1               5                   10                  15

Gly Arg Ile

<210> SEQ ID NO 11
<211> LENGTH: 41
<212> TYPE: PRT
<213> ORGANISM: Artificial Sequence
<220> FEATURE:
<223> OTHER INFORMATION: SP34_VH|HFWR3|Chothia

<400> SEQUENCE: 11

Thr Tyr Tyr Ala Asp Ser Val Lys Asp Arg Phe Thr Ile Ser Arg Asp
1               5                   10                  15

Asp Ser Gln Ser Ile Leu Tyr Leu Gln Met Asn Asn Leu Lys Thr Glu
            20                  25                  30

Asp Thr Ala Met Tyr Tyr Cys Val Arg
        35                  40

<210> SEQ ID NO 12
<211> LENGTH: 41
<212> TYPE: PRT
<213> ORGANISM: Artificial Sequence
<220> FEATURE:
<223> OTHER INFORMATION: VH3230|HFWR3|Chothia; VH3233|HFWR3|Chothia

<400> SEQUENCE: 12
```

```
Thr Tyr Tyr Ala Asp Ser Val Lys Asp Arg Phe Thr Ile Ser Arg Asp
1               5                   10                  15

Asn Ser Lys Asn Thr Leu Tyr Leu Gln Met Asn Ser Leu Arg Ala Glu
            20                  25                  30

Asp Thr Ala Val Tyr Tyr Cys Ala Lys
        35                  40
```

<210> SEQ ID NO 13
<211> LENGTH: 41
<212> TYPE: PRT
<213> ORGANISM: Artificial Sequence
<220> FEATURE:
<223> OTHER INFORMATION: VH3231|HFWR3|Chothia; VH3232|HFWR3|Chothia

<400> SEQUENCE: 13

```
Thr Tyr Tyr Ala Asp Ser Val Lys Asp Arg Phe Thr Ile Ser Arg Asp
1               5                   10                  15

Asp Ser Lys Ser Thr Leu Tyr Leu Gln Met Asn Ser Leu Arg Ala Glu
            20                  25                  30

Asp Thr Ala Val Tyr Tyr Cys Val Arg
        35                  40
```

<210> SEQ ID NO 14
<211> LENGTH: 41
<212> TYPE: PRT
<213> ORGANISM: Artificial Sequence
<220> FEATURE:
<223> OTHER INFORMATION: VH3234|HFWR3|Chothia

<400> SEQUENCE: 14

```
Thr Tyr Tyr Ala Asp Ser Val Lys Asp Arg Phe Thr Ile Ser Arg Asp
1               5                   10                  15

Asn Ser Lys Asn Thr Leu Tyr Leu Gln Met Asn Ser Leu Arg Ala Glu
            20                  25                  30

Asp Thr Ala Val Tyr Tyr Cys Val Arg
        35                  40
```

<210> SEQ ID NO 15
<211> LENGTH: 41
<212> TYPE: PRT
<213> ORGANISM: Artificial Sequence
<220> FEATURE:
<223> OTHER INFORMATION: VH3235|HFWR3|Chothia

<400> SEQUENCE: 15

```
Thr Tyr Tyr Ala Asp Ser Val Lys Asp Arg Phe Thr Ile Ser Arg Asp
1               5                   10                  15

Asp Ser Lys Ser Thr Leu Tyr Leu Gln Met Asn Ser Leu Arg Ala Glu
            20                  25                  30

Asp Thr Ala Val Tyr Tyr Cys Ala Lys
        35                  40
```

<210> SEQ ID NO 16
<211> LENGTH: 41
<212> TYPE: PRT
<213> ORGANISM: Artificial Sequence
<220> FEATURE:
<223> OTHER INFORMATION: VH3236|HFWR3|Chothia

<400> SEQUENCE: 16

```
Thr Tyr Tyr Ala Asp Ser Val Lys Asp Arg Phe Thr Ile Ser Arg Asp
1               5                   10                  15
```

```
Asn Ser Lys Ser Thr Leu Tyr Leu Gln Met Asn Ser Leu Arg Ala Glu
            20                  25                  30

Asp Thr Ala Val Tyr Tyr Cys Ala Arg
        35                  40

<210> SEQ ID NO 17
<211> LENGTH: 41
<212> TYPE: PRT
<213> ORGANISM: Artificial Sequence
<220> FEATURE:
<223> OTHER INFORMATION: VH3730|HFWR3|Chothia; VH3735|HFWR3|Chothia

<400> SEQUENCE: 17

Thr Tyr Tyr Ala Asp Ser Val Lys Asp Arg Phe Thr Ile Ser Arg Asp
1               5                   10                  15

Asp Ser Lys Asn Thr Ala Tyr Leu Gln Met Asn Ser Leu Lys Thr Glu
            20                  25                  30

Asp Thr Ala Val Tyr Tyr Cys Thr Arg
        35                  40

<210> SEQ ID NO 18
<211> LENGTH: 41
<212> TYPE: PRT
<213> ORGANISM: Artificial Sequence
<220> FEATURE:
<223> OTHER INFORMATION: VH3731|HFWR3|Chothia; VH3732|HFWR3|Chothia

<400> SEQUENCE: 18

Thr Tyr Tyr Ala Asp Ser Val Lys Asp Arg Phe Thr Ile Ser Arg Asp
1               5                   10                  15

Asp Ser Lys Ser Thr Leu Tyr Leu Gln Met Asn Ser Leu Lys Thr Glu
            20                  25                  30

Asp Thr Ala Val Tyr Tyr Cys Val Arg
        35                  40

<210> SEQ ID NO 19
<211> LENGTH: 41
<212> TYPE: PRT
<213> ORGANISM: Artificial Sequence
<220> FEATURE:
<223> OTHER INFORMATION: VH3733|HFWR3|Chothia

<400> SEQUENCE: 19

Thr Tyr Tyr Ala Asp Ser Val Lys Asp Arg Phe Thr Ile Ser Arg Asp
1               5                   10                  15

Asp Ser Lys Ser Thr Leu Tyr Leu Gln Met Asn Ser Leu Lys Thr Glu
            20                  25                  30

Asp Thr Ala Val Tyr Tyr Cys Thr Arg
        35                  40

<210> SEQ ID NO 20
<211> LENGTH: 41
<212> TYPE: PRT
<213> ORGANISM: Artificial Sequence
<220> FEATURE:
<223> OTHER INFORMATION: VH3734|HFWR3|Chothia

<400> SEQUENCE: 20

Thr Tyr Tyr Ala Asp Ser Val Lys Asp Arg Phe Thr Ile Ser Arg Asp
1               5                   10                  15

Asp Ser Lys Asn Thr Ala Tyr Leu Gln Met Asn Ser Leu Lys Thr Glu
            20                  25                  30
```

-continued

```
Asp Thr Ala Val Tyr Tyr Cys Val Arg
        35                  40

<210> SEQ ID NO 21
<211> LENGTH: 11
<212> TYPE: PRT
<213> ORGANISM: Artificial Sequence
<220> FEATURE:
<223> OTHER INFORMATION: SP34_VH|HFWR4|Chothia

<400> SEQUENCE: 21

Trp Gly Gln Gly Thr Leu Val Thr Val Ser Ala
1               5                   10

<210> SEQ ID NO 22
<211> LENGTH: 11
<212> TYPE: PRT
<213> ORGANISM: Artificial Sequence
<220> FEATURE:
<223> OTHER INFORMATION: VH3230|HFWR4|Chothia; VH3231|HFWR4|Chothia;
      VH3232|HFWR4|Chothia; VH32

<400> SEQUENCE: 22

Trp Gly Gln Gly Thr Leu Val Thr Val Ser Ser
1               5                   10

<210> SEQ ID NO 23
<211> LENGTH: 14
<212> TYPE: PRT
<213> ORGANISM: Artificial Sequence
<220> FEATURE:
<223> OTHER INFORMATION: SP34_VL|LCDR1|Chothia; VK1392|LCDR1|Chothia;
      VK1393|LCDR1|Chothia; VL7

<400> SEQUENCE: 23

Arg Ser Ser Thr Gly Ala Val Thr Thr Ser Asn Tyr Ala Asn
1               5                   10

<210> SEQ ID NO 24
<211> LENGTH: 7
<212> TYPE: PRT
<213> ORGANISM: Artificial Sequence
<220> FEATURE:
<223> OTHER INFORMATION: SP34_VL|LCDR2|Chothia; VK1392|LCDR2|Chothia;
      VK1393|LCDR2|Chothia; VL7

<400> SEQUENCE: 24

Gly Thr Asn Lys Arg Ala Pro
1               5

<210> SEQ ID NO 25
<211> LENGTH: 9
<212> TYPE: PRT
<213> ORGANISM: Artificial Sequence
<220> FEATURE:
<223> OTHER INFORMATION: SP34_VL|LCDR3|Chothia; VK1392|LCDR3|Chothia;
      VK1393|LCDR3|Chothia; VL7

<400> SEQUENCE: 25

Ala Leu Trp Tyr Ser Asn Leu Trp Val
1               5

<210> SEQ ID NO 26
<211> LENGTH: 22
<212> TYPE: PRT
<213> ORGANISM: Artificial Sequence
<220> FEATURE:
<223> OTHER INFORMATION: SP34_VL|LFWR1|Chothia
```

```
<400> SEQUENCE: 26

Gln Ala Val Val Thr Gln Glu Ser Ala Leu Thr Thr Ser Pro Gly Glu
1               5                   10                  15

Thr Val Thr Leu Thr Cys
            20

<210> SEQ ID NO 27
<211> LENGTH: 22
<212> TYPE: PRT
<213> ORGANISM: Artificial Sequence
<220> FEATURE:
<223> OTHER INFORMATION: VL7460|LFWR1|Chothia; VL7461|LFWR1|Chothia

<400> SEQUENCE: 27

Gln Ala Val Val Thr Gln Glu Pro Ser Leu Thr Val Ser Pro Gly Gly
1               5                   10                  15

Thr Val Thr Leu Thr Cys
            20

<210> SEQ ID NO 28
<211> LENGTH: 23
<212> TYPE: PRT
<213> ORGANISM: Artificial Sequence
<220> FEATURE:
<223> OTHER INFORMATION: VK1392|LFWR1|Chothia

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 29
<211> LENGTH: 23
<212> TYPE: PRT
<213> ORGANISM: Artificial Sequence
<220> FEATURE:
<223> OTHER INFORMATION: VK1393|LFWR1|Chothia

<400> SEQUENCE: 29

Asp Ala Gln Met Thr Gln Ser Pro Ser Ser Leu Ser Ala Ser Val Gly
1               5                   10                  15

Asp Arg Val Thr Ile Thr Cys
            20

<210> SEQ ID NO 30
<211> LENGTH: 15
<212> TYPE: PRT
<213> ORGANISM: Artificial Sequence
<220> FEATURE:
<223> OTHER INFORMATION: SP34_VL|LFWR2|Chothia

<400> SEQUENCE: 30

Trp Val Gln Glu Lys Pro Asp His Leu Phe Thr Gly Leu Ile Gly
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: VK1392|LFWR2|Chothia

<400> SEQUENCE: 31
```

```
Trp Tyr Gln Gln Lys Pro Gly Lys Ala Pro Lys Leu Leu Ile Tyr
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: VK1393|LFWR2|Chothia

<400> SEQUENCE: 32

Trp Val Gln Gln Lys Pro Gly Lys Ala Pro Lys Gly Leu Ile Gly
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: VL7460|LFWR2|Chothia

<400> SEQUENCE: 33

Trp Phe Gln Gln Lys Pro Gly Gln Ala Pro Arg Thr Leu Ile Tyr
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: VL7461|LFWR2|Chothia

<400> SEQUENCE: 34

Trp Val Gln Gln Lys Pro Gly Gln Ala Pro Arg Gly Leu Ile Gly
1               5                   10                  15

<210> SEQ ID NO 35
<211> LENGTH: 32
<212> TYPE: PRT
<213> ORGANISM: Artificial Sequence
<220> FEATURE:
<223> OTHER INFORMATION: SP34_VL|LFWR3|Chothia

<400> SEQUENCE: 35

Gly Val Pro Ala Arg Phe Ser Gly Ser Leu Ile Gly Asp Lys Ala Ala
1               5                   10                  15

Leu Thr Ile Thr Gly Ala Gln Thr Glu Asp Glu Ala Ile Tyr Phe Cys
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: VK1392|LFWR3|Chothia

<400> SEQUENCE: 36

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 37
<211> LENGTH: 32
<212> TYPE: PRT
```

<213> ORGANISM: Artificial Sequence
<220> FEATURE:
<223> OTHER INFORMATION: VK1393|LFWR3|Chothia

<400> SEQUENCE: 37

Gly Val Pro Ser Arg Phe Ser Gly Ser Leu Ser Gly Asp Asp Ala Thr
1               5                   10                  15

Leu Thr Ile Ser Ser Leu Gln Pro Glu Asp Phe Ala Thr Tyr Phe Cys
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: VL7460|LFWR3|Chothia

<400> SEQUENCE: 38

Trp Thr Pro Ala Arg Phe Ser Gly Ser Leu Leu Gly Gly Lys Ala Ala
1               5                   10                  15

Leu Thr Leu Leu Gly Ala Gln Pro Glu Asp Glu Ala Glu Tyr Tyr Cys
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: VL7461|LFWR3|Chothia

<400> SEQUENCE: 39

Trp Thr Pro Ala Arg Phe Ser Gly Ser Leu Leu Gly Asp Lys Ala Ala
1               5                   10                  15

Leu Thr Leu Leu Gly Ala Gln Pro Glu Asp Glu Ala Glu Tyr Phe Cys
            20                  25                  30

<210> SEQ ID NO 40
<211> LENGTH: 10
<212> TYPE: PRT
<213> ORGANISM: Artificial Sequence
<220> FEATURE:
<223> OTHER INFORMATION: SP34_VL|LFWR4|Chothia; VL7460|LFWR4|Chothia;
     VL7461|LFWR4|Chothia

<400> SEQUENCE: 40

Phe Gly Gly Gly Thr Lys Leu Thr Val Leu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: VK1392|LFWR4|Chothia; VK1393|LFWR4|Chothia

<400> SEQUENCE: 41

Phe Gly Gly Gly Thr Lys Val Glu Ile Lys
1               5                   10

<210> SEQ ID NO 42
<211> LENGTH: 125
<212> TYPE: PRT
<213> ORGANISM: Artificial Sequence
<220> FEATURE:
<223> OTHER INFORMATION: SP34_VH|VH|Chothia

```
<400> SEQUENCE: 42

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 43
<211> LENGTH: 125
<212> TYPE: PRT
<213> ORGANISM: Artificial Sequence
<220> FEATURE:
<223> OTHER INFORMATION: VH3230|VH|Chothia

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 44
<211> LENGTH: 125
<212> TYPE: PRT
<213> ORGANISM: Artificial Sequence
<220> FEATURE:
<223> OTHER INFORMATION: VH3231|VH|Chothia

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45
```

-continued

```
Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 45
<211> LENGTH: 125
<212> TYPE: PRT
<213> ORGANISM: Artificial Sequence
<220> FEATURE:
<223> OTHER INFORMATION: VH3232|VH|Chothia

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 46
<211> LENGTH: 125
<212> TYPE: PRT
<213> ORGANISM: Artificial Sequence
<220> FEATURE:
<223> OTHER INFORMATION: VH3233|VH|Chothia

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys His Gly Asn Phe Gly Asn Ser Tyr Val Ser Trp Phe
            100                 105                 110
```

-continued

```
Ala Tyr Trp Gly Gln Gly Thr Leu Val Thr Val Ser Ser
        115                 120                 125

<210> SEQ ID NO 47
<211> LENGTH: 125
<212> TYPE: PRT
<213> ORGANISM: Artificial Sequence
<220> FEATURE:
<223> OTHER INFORMATION: VH3234|VH|Chothia

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 48
<211> LENGTH: 125
<212> TYPE: PRT
<213> ORGANISM: Artificial Sequence
<220> FEATURE:
<223> OTHER INFORMATION: VH3235|VH|Chothia

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Ala Lys His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 49
<211> LENGTH: 125
<212> TYPE: PRT
<213> ORGANISM: Artificial Sequence
<220> FEATURE:
<223> OTHER INFORMATION: VH3236|VH|Chothia
```

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 50
<211> LENGTH: 125
<212> TYPE: PRT
<213> ORGANISM: Artificial Sequence
<220> FEATURE:
<223> OTHER INFORMATION: VH3730|VH|Chothia

<400> SEQUENCE: 50

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 51
<211> LENGTH: 125
<212> TYPE: PRT
<213> ORGANISM: Artificial Sequence
<220> FEATURE:
<223> OTHER INFORMATION: VH3731|VH|Chothia

<400> SEQUENCE: 51

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

```
Gly Arg Ile Arg Ser Lys Tyr Asn Asn Tyr Ala Thr Tyr Tyr Ala Asp
    50              55              60
```

```
Ser Val Lys Asp Arg Phe Thr Ile Ser Arg Asp Asp Ser Lys Ser Thr
65              70              75              80
```

```
Leu Tyr Leu Gln Met Asn Ser Leu Lys Thr Glu Asp Thr Ala Val Tyr
                85              90              95
```

```
Tyr Cys Val Arg His Gly Asn Phe Gly Asn Ser Tyr Val Ser Trp Phe
            100             105             110
```

```
Ala Tyr Trp Gly Gln Gly Thr Leu Val Thr Val Ser Ser
        115             120             125
```

<210> SEQ ID NO 52
<211> LENGTH: 125
<212> TYPE: PRT
<213> ORGANISM: Artificial Sequence
<220> FEATURE:
<223> OTHER INFORMATION: VH3732|VH|Chothia

<400> SEQUENCE: 52

```
Glu Val Gln Leu Val Glu Ser Gly Gly Gly Leu Val Gln Pro Gly Gly
1               5               10              15
```

```
Ser Leu Lys Leu Ser Cys Ala Ala Ser Gly Phe Thr Phe Ser Thr Tyr
                20              25              30
```

```
Ala Met Asn Trp Val Arg Gln Ala Ser Gly Lys Gly Leu Glu Trp Val
            35              40              45
```

```
Gly Arg Ile Arg Ser Lys Tyr Asn Asn Tyr Ala Thr Tyr Tyr Ala Asp
    50              55              60
```

```
Ser Val Lys Asp Arg Phe Thr Ile Ser Arg Asp Asp Ser Lys Ser Thr
65              70              75              80
```

```
Leu Tyr Leu Gln Met Asn Ser Leu Lys Thr Glu Asp Thr Ala Val Tyr
                85              90              95
```

```
Tyr Cys Val Arg His Gly Asn Phe Gly Asn Ser Tyr Val Ser Trp Phe
            100             105             110
```

```
Ala Tyr Trp Gly Gln Gly Thr Leu Val Thr Val Ser Ser
        115             120             125
```

<210> SEQ ID NO 53
<211> LENGTH: 125
<212> TYPE: PRT
<213> ORGANISM: Artificial Sequence
<220> FEATURE:
<223> OTHER INFORMATION: VH3733|VH|Chothia

<400> SEQUENCE: 53

```
Glu Val Gln Leu Val Glu Ser Gly Gly Gly Leu Val Gln Pro Gly Gly
1               5               10              15
```

```
Ser Leu Lys Leu Ser Cys Ala Ala Ser Gly Phe Thr Phe Ser Thr Tyr
                20              25              30
```

```
Ala Met Asn Trp Val Arg Gln Ala Ser Gly Lys Gly Leu Glu Trp Val
            35              40              45
```

```
Gly Arg Ile Arg Ser Lys Tyr Asn Asn Tyr Ala Thr Tyr Tyr Ala Asp
    50              55              60
```

```
Ser Val Lys Asp Arg Phe Thr Ile Ser Arg Asp Asp Ser Lys Ser Thr
65              70              75              80
```

```
Leu Tyr Leu Gln Met Asn Ser Leu Lys Thr Glu Asp Thr Ala Val Tyr
                85              90              95
```

```
Tyr Cys Thr Arg His Gly Asn Phe Gly Asn Ser Tyr Val Ser Trp Phe
```

-continued

```
             100              105              110

Ala Tyr Trp Gly Gln Gly Thr Leu Val Thr Val Ser Ser
        115              120              125

<210> SEQ ID NO 54
<211> LENGTH: 125
<212> TYPE: PRT
<213> ORGANISM: Artificial Sequence
<220> FEATURE:
<223> OTHER INFORMATION: VH3734|VH|Chothia

<400> SEQUENCE: 54

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100              105              110

Ala Tyr Trp Gly Gln Gly Thr Leu Val Thr Val Ser Ser
        115              120              125

<210> SEQ ID NO 55
<211> LENGTH: 125
<212> TYPE: PRT
<213> ORGANISM: Artificial Sequence
<220> FEATURE:
<223> OTHER INFORMATION: VH3735|VH|Chothia

<400> SEQUENCE: 55

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100              105              110

Ala Tyr Trp Gly Gln Gly Thr Leu Val Thr Val Ser Ser
        115              120              125

<210> SEQ ID NO 56
<211> LENGTH: 109
<212> TYPE: PRT
<213> ORGANISM: Artificial Sequence
<220> FEATURE:
```

<223> OTHER INFORMATION: SP34_VL|VL|Chothia

<400> SEQUENCE: 56

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 57
<211> LENGTH: 109
<212> TYPE: PRT
<213> ORGANISM: Artificial Sequence
<220> FEATURE:
<223> OTHER INFORMATION: VL7460|VL|Chothia

<400> SEQUENCE: 57

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Thr
        35                  40                  45

Leu Ile Tyr Gly Thr Asn Lys Arg Ala Pro Trp Thr Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 58
<211> LENGTH: 109
<212> TYPE: PRT
<213> ORGANISM: Artificial Sequence
<220> FEATURE:
<223> OTHER INFORMATION: VL7461|VL|Chothia

<400> SEQUENCE: 58

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Asp Lys Ala Ala Leu Thr Leu Leu Gly Ala

-continued

```
65              70              75              80

Gln Pro Glu Asp Glu Ala Glu Tyr Phe Cys Ala Leu Trp Tyr Ser Asn
                85              90              95

Leu Trp Val Phe Gly Gly Gly Thr Lys Leu Thr Val Leu
            100             105

<210> SEQ ID NO 59
<211> LENGTH: 110
<212> TYPE: PRT
<213> ORGANISM: Artificial Sequence
<220> FEATURE:
<223> OTHER INFORMATION: VK1392|VL|Chothia

<400> SEQUENCE: 59

Asp Ile Gln Met Thr Gln Ser Pro Ser Ser Leu Ser Ala Ser Val Gly
1               5               10              15

Asp Arg Val Thr Ile Thr Cys Arg Ser Ser Thr Gly Ala Val Thr Thr
                20              25              30

Ser Asn Tyr Ala Asn Trp Tyr Gln Gln Lys Pro Gly Lys Ala Pro Lys
            35              40              45

Leu Leu Ile Tyr Gly Thr Asn Lys Arg Ala Pro Gly Val Pro Ser Arg
        50              55              60

Phe Ser Gly Ser Gly Ser Gly Thr Asp Phe Thr Leu Thr Ile Ser Ser
65              70              75              80

Leu Gln Pro Glu Asp Phe Ala Thr Tyr Tyr Cys Ala Leu Trp Tyr Ser
                85              90              95

Asn Leu Trp Val Phe Gly Gly Gly Thr Lys Val Glu Ile Lys
            100             105             110

<210> SEQ ID NO 60
<211> LENGTH: 110
<212> TYPE: PRT
<213> ORGANISM: Artificial Sequence
<220> FEATURE:
<223> OTHER INFORMATION: VK1393|VL|Chothia

<400> SEQUENCE: 60

Asp Ala Gln Met Thr Gln Ser Pro Ser Ser Leu Ser Ala Ser Val Gly
1               5               10              15

Asp Arg Val Thr Ile Thr Cys Arg Ser Ser Thr Gly Ala Val Thr Thr
                20              25              30

Ser Asn Tyr Ala Asn Trp Val Gln Gln Lys Pro Gly Lys Ala Pro Lys
            35              40              45

Gly Leu Ile Gly Gly Thr Asn Lys Arg Ala Pro Gly Val Pro Ser Arg
        50              55              60

Phe Ser Gly Ser Leu Ser Gly Asp Asp Ala Thr Leu Thr Ile Ser Ser
65              70              75              80

Leu Gln Pro Glu Asp Phe Ala Thr Tyr Phe Cys Ala Leu Trp Tyr Ser
                85              90              95

Asn Leu Trp Val Phe Gly Gly Gly Thr Lys Val Glu Ile Lys
            100             105             110

<210> SEQ ID NO 61
<211> LENGTH: 107
<212> TYPE: PRT
<213> ORGANISM: Artificial Sequence
<220> FEATURE:
<223> OTHER INFORMATION: human Ck

<400> SEQUENCE: 61
```

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 62
<211> LENGTH: 106
<212> TYPE: PRT
<213> ORGANISM: Artificial Sequence
<220> FEATURE:
<223> OTHER INFORMATION: human C_lambda

<400> SEQUENCE: 62
```

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

```
<210> SEQ ID NO 63
<211> LENGTH: 330
<212> TYPE: PRT
<213> ORGANISM: Artificial Sequence
<220> FEATURE:
<223> OTHER INFORMATION: human IgG1 heavy chain constant regions(with
      L234A, L235A)

<400> SEQUENCE: 63
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

-continued

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 64
<211> LENGTH: 330
<212> TYPE: PRT
<213> ORGANISM: Artificial Sequence
<220> FEATURE:
<223> OTHER INFORMATION: human IgG1 heavy chain constant regions(with
      L234A, L235A, P329G)

<400> SEQUENCE: 64
```

```
Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

-continued

```
Pro Ala Pro Glu Ala Ala Gly Gly Pro Ser Val Phe Leu Phe Pro Pro
        115                 120             125

Lys Pro Lys Asp Thr Leu Met Ile Ser Arg Thr Pro Glu Val Thr Cys
    130             135                 140

Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 65
<211> LENGTH: 15
<212> TYPE: PRT
<213> ORGANISM: Artificial Sequence
<220> FEATURE:
<223> OTHER INFORMATION: (G4S)3 linker

<400> SEQUENCE: 65

Gly Gly Gly Gly Ser Gly Gly Gly Gly Ser Gly Gly Gly Gly Ser
1               5                   10                  15
```

```
<210> SEQ ID NO 66
<211> LENGTH: 20
<212> TYPE: PRT
<213> ORGANISM: Artificial Sequence
<220> FEATURE:
<223> OTHER INFORMATION: (G4S)4 linker

<400> SEQUENCE: 66

Gly Gly Gly Gly Ser Gly Gly Gly Gly Ser Gly Gly Gly Gly Ser Gly
1               5                   10                  15

Gly Gly Gly Ser
            20
```

```
<210> SEQ ID NO 67
<211> LENGTH: 15
<212> TYPE: PRT
<213> ORGANISM: Artificial Sequence
<220> FEATURE:
<223> OTHER INFORMATION: (G4S)3 linker variant
```

-continued

<400> SEQUENCE: 67

Gly Gly Gly Gln Ser Gly Gln Gly Gly Ser Gly Gly Gly Gly Ser
1               5                   10                  15

<210> SEQ ID NO 68
<211> LENGTH: 258
<212> TYPE: PRT
<213> ORGANISM: Artificial Sequence
<220> FEATURE:
<223> OTHER INFORMATION: synthetic antibody PR000275 anti-CD3e
      SP34_scFv_L3H-6His

<400> SEQUENCE: 68

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Gly Gly Gly
                100                 105                 110

Gly Ser Gly Gly Gly Gly Ser Gly Gly Gly Ser Glu Val Gln Leu
            115                 120                 125

Val Glu Ser Gly Gly Gly Leu Val Gln Pro Lys Gly Ser Leu Lys Leu
            130                 135                 140

Ser Cys Ala Ala Ser Gly Phe Thr Phe Asn Thr Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
                180                 185                 190

Arg Phe Thr Ile Ser Arg Asp Asp Ser Gln Ser Ile Leu Tyr Leu Gln
            195                 200                 205

Met Asn Asn Leu Lys Thr Glu Asp Thr Ala Met Tyr Tyr Cys Val Arg
        210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ala Gly Gly Ser His His His His
                245                 250                 255

His His

<210> SEQ ID NO 69
<211> LENGTH: 258
<212> TYPE: PRT
<213> ORGANISM: Artificial Sequence
<220> FEATURE:
<223> OTHER INFORMATION: synthetic antibody PR000276 anti-CD3e
      SP34_scFv_H3L-6His

<400> SEQUENCE: 69

Glu Val Gln Leu Val Glu Ser Gly Gly Gly Leu Val Gln Pro Lys Gly

-continued

```
1               5                   10                  15
Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala Gly Gly Gly
            115                 120                 125

Gly Ser Gly Gly Gly Gly Ser Gly Gly Gly Gly Ser Gln Ala Val Val
    130                 135                 140

Thr Gln Glu Ser Ala Leu Thr Thr Ser Pro Gly Glu Thr Val Thr Leu
145                 150                 155                 160

Thr Cys Arg Ser Ser Thr Gly Ala Val Thr Thr Ser Asn Tyr Ala Asn
            165                 170                 175

Trp Val Gln Glu Lys Pro Asp His Leu Phe Thr Gly Leu Ile Gly Gly
            180                 185                 190

Thr Asn Lys Arg Ala Pro Gly Val Pro Ala Arg Phe Ser Gly Ser Leu
            195                 200                 205

Ile Gly Asp Lys Ala Ala Leu Thr Ile Thr Gly Ala Gln Thr Glu Asp
    210                 215                 220

Glu Ala Ile Tyr Phe Cys Ala Leu Trp Tyr Ser Asn Leu Trp Val Phe
225                 230                 235                 240

Gly Gly Gly Thr Lys Leu Thr Val Leu Gly Gly Ser His His His His
            245                 250                 255

His His
```

```
<210> SEQ ID NO 70
<211> LENGTH: 262
<212> TYPE: PRT
<213> ORGANISM: Artificial Sequence
<220> FEATURE:
<223> OTHER INFORMATION: synthetic antibody PR000307 anti-CD3e
      SP34_scFv_L4H-6His

<400> SEQUENCE: 70
```

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Gly Gly Gly
```

-continued

```
                100                 105                 110
Gly Ser Gly Gly Gly Gly Ser Gly Gly Gly Gly Ser Gly Gly Gly
            115                 120                 125

Ser Glu Val Gln Leu Val Glu Ser Gly Gly Gly Leu Val Gln Pro Lys
    130                 135                 140

Gly Ser Leu Lys Leu Ser Cys Ala Ala Ser Gly Phe Thr Phe Asn Thr
145                 150                 155                 160

Tyr Ala Met Asn Trp Val Arg Gln Ala Pro Gly Lys Gly Leu Glu Trp
                165                 170                 175

Val Ala Arg Ile Arg Ser Lys Tyr Asn Asn Tyr Ala Thr Tyr Tyr Ala
                180                 185                 190

Asp Ser Val Lys Asp Arg Phe Thr Ile Ser Arg Asp Asp Ser Gln Ser
            195                 200                 205

Ile Leu Tyr Leu Gln Met Asn Asn Leu Lys Thr Glu Asp Thr Ala Met
    210                 215                 220

Tyr Tyr Cys Val Arg His Gly Asn Phe Gly Asn Ser Tyr Val Ser Trp
225                 230                 235                 240

Phe Ala Tyr Trp Gly Gln Gly Thr Leu Val Thr Val Ser Ala Ala Ser
                245                 250                 255

His His His His His His
            260
```

```
<210> SEQ ID NO 71
<211> LENGTH: 262
<212> TYPE: PRT
<213> ORGANISM: Artificial Sequence
<220> FEATURE:
<223> OTHER INFORMATION: synthetic antibody PR000308 anti-CD3e
      SP34_scFv_H4L-6His

<400> SEQUENCE: 71

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala Gly Gly Gly
            115                 120                 125

Gly Ser Gly Gly Gly Gly Ser Gly Gly Gly Gly Ser Gly Gly Gly Gly
            130                 135                 140

Ser Gln Ala Val Val Thr Gln Glu Ser Ala Leu Thr Thr Ser Pro Gly
145                 150                 155                 160

Glu Thr Val Thr Leu Thr Cys Arg Ser Ser Thr Gly Ala Val Thr Thr
                165                 170                 175

Ser Asn Tyr Ala Asn Trp Val Gln Glu Lys Pro Asp His Leu Phe Thr
            180                 185                 190
```

```
Gly Leu Ile Gly Gly Thr Asn Lys Arg Ala Pro Gly Val Pro Ala Arg
        195                 200                 205

Phe Ser Gly Ser Leu Ile Gly Asp Lys Ala Ala Leu Thr Ile Thr Gly
        210                 215                 220

Ala Gln Thr Glu Asp Glu Ala Ile Tyr Phe Cys Ala Leu Trp Tyr Ser
225                 230                 235                 240

Asn Leu Trp Val Phe Gly Gly Gly Thr Lys Leu Thr Val Leu Ala Ser
                245                 250                 255

His His His His His His
        260

<210> SEQ ID NO 72
<211> LENGTH: 483
<212> TYPE: PRT
<213> ORGANISM: Artificial Sequence
<220> FEATURE:
<223> OTHER INFORMATION: synthetic antibody PR000509 anti-CD3 SP34
      hum-scFv(VH3731-GS-VL7461)-hFc(LALA)

<400> SEQUENCE: 72

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Gly
            115                 120                 125

Gln Ser Gly Gln Gly Gly Ser Gly Gly Gly Ser Gln Ala Val Val
        130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Gln Lys Pro Gly Gln Ala Pro Arg Gly Leu Ile Gly Gly
            180                 185                 190

Thr Asn Lys Arg Ala Pro Trp Thr Pro Ala Arg Phe Ser Gly Ser Leu
        195                 200                 205

Leu Gly Asp Lys Ala Ala Leu Thr Leu Leu Gly Ala Gln Pro Glu Asp
        210                 215                 220

Glu Ala Glu Tyr Phe Cys Ala Leu Trp Tyr Ser Asn Leu Trp Val Phe
225                 230                 235                 240

Gly Gly Gly Thr Lys Leu Thr Val Leu Ala Ser Glu Pro Lys Ser Cys
                245                 250                 255

Asp Lys Thr His Thr Cys Pro Pro Cys Pro Ala Pro Glu Ala Ala Gly
            260                 265                 270

Gly Pro Ser Val Phe Leu Phe Pro Pro Lys Pro Lys Asp Thr Leu Met
            275                 280                 285
```

-continued

```
Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Glu Tyr Lys Cys Lys Val Ser Asn Lys Ala Leu Pro Ala Pro Ile
                355                 360                 365

Glu Lys Thr Ile Ser Lys Ala Lys Gly Gln Pro Arg Glu Pro Gln Val
                370                 375                 380

Tyr Thr Leu Pro Pro Ser Arg Glu Glu Met Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys
```

```
<210> SEQ ID NO 73
<211> LENGTH: 483
<212> TYPE: PRT
<213> ORGANISM: Artificial Sequence
<220> FEATURE:
<223> OTHER INFORMATION: synthetic antibody PR000510 anti-CD3 SP34
      hum-scFv(VL7461-GS-VH3731)-hFc(LALA)

<400> SEQUENCE: 73
```

```
Gln Ala Val Val Thr Gln Glu Pro Ser Leu Thr Val Ser Pro Gly Gly
1                   5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
    50                  55                  60

Ser Gly Ser Leu Leu Gly Asp Lys Ala Ala Leu Thr Leu Leu Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gly Gly
                100                 105                 110

Gln Ser Gly Gln Gly Gly Ser Gly Gly Gly Gly Ser Glu Val Gln Leu
            115                 120                 125

Val Glu Ser Gly Gly Gly Leu Val Gln Pro Gly Gly Ser Leu Lys Leu
            130                 135                 140

Ser Cys Ala Ala Ser Gly Phe Thr Phe Asn Thr Tyr Ala Met Asn Trp
145                 150                 155                 160
```

Val Arg Gln Ala Ser Gly Lys Gly Leu Glu Trp Val Gly Arg Ile Arg
              165                 170                 175

Ser Lys Tyr Asn Asn Tyr Ala Thr Tyr Tyr Ala Asp Ser Val Lys Asp
              180                 185                 190

Arg Phe Thr Ile Ser Arg Asp Asp Ser Lys Ser Thr Leu Tyr Leu Gln
              195                 200                 205

Met Asn Ser Leu Lys Thr Glu Asp Thr Ala Val Tyr Tyr Cys Val Arg
          210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser Ala Ser Glu Pro Lys Ser Cys
              245                 250                 255

Asp Lys Thr His Thr Cys Pro Pro Cys Pro Ala Pro Glu Ala Ala Gly
              260                 265                 270

Gly Pro Ser Val Phe Leu Phe Pro Pro Lys Pro Lys Asp Thr Leu Met
              275                 280                 285

Ile Ser Arg Thr Pro Glu Val Thr Cys Val Val Val Asp Val Ser His
          290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
              325                 330                 335

Arg Val Val Ser Val Leu Thr Val Leu His Gln Asp Trp Leu Asn Gly
              340                 345                 350

Lys Glu Tyr Lys Cys Lys Val Ser Asn Lys Ala Leu Pro Ala Pro Ile
              355                 360                 365

Glu Lys Thr Ile Ser Lys Ala Lys Gly Gln Pro Arg Glu Pro Gln Val
          370                 375                 380

Tyr Thr Leu Pro Pro Ser Arg Glu Glu Met Thr Lys Asn Gln Val Ser
385                 390                 395                 400

Leu Thr Cys Leu Val Lys Gly Phe Tyr Pro Ser Asp Ile Ala Val Glu
              405                 410                 415

Trp Glu Ser Asn Gly Gln Pro Glu Asn Asn Tyr Lys Thr Thr Pro Pro
              420                 425                 430

Val Leu Asp Ser Asp Gly Ser Phe Phe Leu Tyr Ser Lys Leu Thr Val
              435                 440                 445

Asp Lys Ser Arg Trp Gln Gln Gly Asn Val Phe Ser Cys Ser Val Met
          450                 455                 460

His Glu Ala Leu His Asn His Tyr Thr Gln Lys Ser Leu Ser Leu Ser
465                 470                 475                 480

Pro Gly Lys

<210> SEQ ID NO 74
<211> LENGTH: 484
<212> TYPE: PRT
<213> ORGANISM: Artificial Sequence
<220> FEATURE:
<223> OTHER INFORMATION: synthetic antibody PR000623 anti-CD3E SP34
      hum-scFv(VH3231_GS_VK1393)-hFc(C220S,LALA)

<400> SEQUENCE: 74

Glu Val Gln Leu Leu Glu Ser Gly Gly Gly Leu Val Gln Pro Gly Gly
1                 5                 10                 15

Ser Leu Arg Leu Ser Cys Ala Ala Ser Gly Phe Thr Phe Asn Thr Tyr
              20                 25                 30

```
Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Gly
            115                 120                 125

Gln Ser Gly Gln Gly Gly Ser Gly Gly Gly Gly Ser Asp Ala Gln Met
    130                 135                 140

Thr Gln Ser Pro Ser Ser Leu Ser Ala Ser Val Gly Asp Arg Val Thr
145                 150                 155                 160

Ile Thr Cys Arg Ser Ser Thr Gly Ala Val Thr Thr Ser Asn Tyr Ala
                165                 170                 175

Asn Trp Val Gln Gln Lys Pro Gly Lys Ala Pro Lys Gly Leu Ile Gly
            180                 185                 190

Gly Thr Asn Lys Arg Ala Pro Gly Val Pro Ser Arg Phe Ser Gly Ser
            195                 200                 205

Leu Ser Gly Asp Asp Ala Thr Leu Thr Ile Ser Ser Leu Gln Pro Glu
    210                 215                 220

Asp Phe Ala Thr Tyr Phe Cys Ala Leu Trp Tyr Ser Asn Leu Trp Val
225                 230                 235                 240

Phe Gly Gly Gly Thr Lys Val Glu Ile Lys Ala Ser Glu Pro Lys Ser
                245                 250                 255

Ser Asp Lys Thr His Thr Cys Pro Pro Cys Pro Ala Pro Glu Ala Ala
            260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
            355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
            435                 440                 445
```

```
Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys
```

```
<210> SEQ ID NO 75
<211> LENGTH: 484
<212> TYPE: PRT
<213> ORGANISM: Artificial Sequence
<220> FEATURE:
<223> OTHER INFORMATION: synthetic antibody PR000624 anti-CD3E SP34
      hum-scFv(VH3731_GS_VK1393)-hFc(C220S,LALA)

<400> SEQUENCE: 75
```

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
            35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Gly
            115                 120                 125

Gln Ser Gly Gln Gly Gly Ser Gly Gly Gly Ser Asp Ala Gln Met
    130                 135                 140

Thr Gln Ser Pro Ser Ser Leu Ser Ala Ser Val Gly Asp Arg Val Thr
145                 150                 155                 160

Ile Thr Cys Arg Ser Ser Thr Gly Ala Val Thr Thr Ser Asn Tyr Ala
            165                 170                 175

Asn Trp Val Gln Gln Lys Pro Gly Lys Ala Pro Lys Gly Leu Ile Gly
            180                 185                 190

Gly Thr Asn Lys Arg Ala Pro Gly Val Pro Ser Arg Phe Ser Gly Ser
            195                 200                 205

Leu Ser Gly Asp Asp Ala Thr Leu Thr Ile Ser Ser Leu Gln Pro Glu
    210                 215                 220

Asp Phe Ala Thr Tyr Phe Cys Ala Leu Trp Tyr Ser Asn Leu Trp Val
225                 230                 235                 240

Phe Gly Gly Gly Thr Lys Val Glu Ile Lys Ala Ser Glu Pro Lys Ser
                245                 250                 255

Ser Asp Lys Thr His Thr Cys Pro Pro Cys Pro Ala Pro Glu Ala Ala
            260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320
```

-continued

```
Val His Asn Ala Lys Thr Lys Pro Arg Glu Glu Gln Tyr Asn Ser Thr
            325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
            355                 360                 365

Ile Glu Lys Thr Ile Ser Lys Ala Lys Gly Gln Pro Arg Glu Pro Gln
        370                 375                 380

Val Tyr Thr Leu Pro Pro Ser Arg Glu Glu Met Thr Lys Asn Gln Val
385                 390                 395                 400

Ser Leu Thr Cys Leu Val Lys Gly Phe Tyr Pro Ser Asp Ile Ala Val
            405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
            435                 440                 445

Val Asp Lys Ser Arg Trp Gln Gln Gly Asn Val Phe Ser Cys Ser Val
        450                 455                 460

Met His Glu Ala Leu His Asn His Tyr Thr Gln Lys Ser Leu Ser Leu
465                 470                 475                 480

Ser Pro Gly Lys
```

```
<210> SEQ ID NO 76
<211> LENGTH: 484
<212> TYPE: PRT
<213> ORGANISM: Artificial Sequence
<220> FEATURE:
<223> OTHER INFORMATION: synthetic antibody PR000625 anti-CD3E SP34
      hum-scFv(VK1393_GS_VH3231)-hFc(C220S,LALA)

<400> SEQUENCE: 76
```

```
Asp Ala Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ser Gly Asp Asp Ala Thr Leu Thr Ile Ser Ser
65                  70                  75                  80

Leu Gln Pro Glu Asp Phe Ala Thr Tyr Phe Cys Ala Leu Trp Tyr Ser
                85                  90                  95

Asn Leu Trp Val Phe Gly Gly Gly Thr Lys Val Glu Ile Lys Gly Gly
            100                 105                 110

Gly Gln Ser Gly Gln Gly Gly Ser Gly Gly Gly Gly Ser Glu Val Gln
        115                 120                 125

Leu Leu Glu Ser Gly Gly Gly Leu Val Gln Pro Gly Gly Ser Leu Arg
    130                 135                 140

Leu Ser Cys Ala Ala Ser Gly Phe Thr Phe Asn Thr Tyr Ala Met Asn
145                 150                 155                 160

Trp Val Arg Gln Ala Pro Gly Lys Gly Leu Glu Trp Val Ser Arg Ile
            165                 170                 175

Arg Ser Lys Tyr Asn Asn Tyr Ala Thr Tyr Tyr Ala Asp Ser Val Lys
        180                 185                 190
```

```
Asp Arg Phe Thr Ile Ser Arg Asp Asp Ser Lys Ser Thr Leu Tyr Leu
        195                 200                 205

Gln Met Asn Ser Leu Arg Ala Glu Asp Thr Ala Val Tyr Tyr Cys Val
        210                 215                 220

Arg His Gly Asn Phe Gly Asn Ser Tyr Val Ser Trp Phe Ala Tyr Trp
225                 230                 235                 240

Gly Gln Gly Thr Leu Val Thr Val Ser Ser Ala Ser Glu Pro Lys Ser
                245                 250                 255

Ser Asp Lys Thr His Thr Cys Pro Pro Cys Pro Ala Pro Glu Ala Ala
        260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
        290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
                340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
        370                 375                 380

Val Tyr Thr Leu Pro Pro Ser Arg Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
                420                 425                 430

Pro Val Leu Asp Ser Asp Gly Ser Phe Phe Leu Tyr Ser Lys Leu Thr
                435                 440                 445

Val Asp Lys Ser Arg Trp Gln Gln Gly Asn Val Phe Ser Cys Ser Val
        450                 455                 460

Met His Glu Ala Leu His Asn His Tyr Thr Gln Lys Ser Leu Ser Leu
465                 470                 475                 480

Ser Pro Gly Lys

<210> SEQ ID NO 77
<211> LENGTH: 484
<212> TYPE: PRT
<213> ORGANISM: Artificial Sequence
<220> FEATURE:
<223> OTHER INFORMATION: synthetic antibody PR000626 anti-CD3E SP34
      hum-scFv(VK1393_GS_VH3731)-hFc(C220S,LALA)

<400> SEQUENCE: 77

Asp Ala Gln Met Thr Gln Ser Pro Ser Ser Leu Ser Ala Ser Val Gly
1                 5                 10                 15

Asp Arg Val Thr Ile Thr Cys Arg Ser Ser Thr Gly Ala Val Thr Thr
                20                 25                 30

Ser Asn Tyr Ala Asn Trp Val Gln Gln Lys Pro Gly Lys Ala Pro Lys
        35                 40                 45

Gly Leu Ile Gly Gly Thr Asn Lys Arg Ala Pro Gly Val Pro Ser Arg
        50                 55                 60
```

```
Phe Ser Gly Ser Leu Ser Gly Asp Asp Ala Thr Leu Thr Ile Ser Ser
65              70                  75                  80

Leu Gln Pro Glu Asp Phe Ala Thr Tyr Phe Cys Ala Leu Trp Tyr Ser
                85                  90                  95

Asn Leu Trp Val Phe Gly Gly Gly Thr Lys Val Glu Ile Lys Gly Gly
            100                 105                 110

Gly Gln Ser Gly Gln Gly Gly Ser Gly Gly Gly Ser Glu Val Gln
            115                 120                 125

Leu Val Glu Ser Gly Gly Gly Leu Val Gln Pro Gly Gly Ser Leu Lys
    130                 135                 140

Leu Ser Cys Ala Ala Ser Gly Phe Thr Phe Asn Thr Tyr Ala Met Asn
145                 150                 155                 160

Trp Val Arg Gln Ala Ser Gly Lys Gly Leu Glu Trp Val Gly Arg Ile
                165                 170                 175

Arg Ser Lys Tyr Asn Asn Tyr Ala Thr Tyr Tyr Ala Asp Ser Val Lys
            180                 185                 190

Asp Arg Phe Thr Ile Ser Arg Asp Asp Ser Lys Ser Thr Leu Tyr Leu
            195                 200                 205

Gln Met Asn Ser Leu Lys Thr Glu Asp Thr Ala Val Tyr Tyr Cys Val
    210                 215                 220

Arg His Gly Asn Phe Gly Asn Ser Tyr Val Ser Trp Phe Ala Tyr Trp
225                 230                 235                 240

Gly Gln Gly Thr Leu Val Thr Val Ser Ser Ala Ser Glu Pro Lys Ser
                245                 250                 255

Ser Asp Lys Thr His Thr Cys Pro Pro Cys Pro Ala Pro Glu Ala Ala
            260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
            355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
                420                 425                 430

Pro Val Leu Asp Ser Asp Gly Ser Phe Phe Leu Tyr Ser Lys Leu Thr
            435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys
```

<210> SEQ ID NO 78
<211> LENGTH: 483
<212> TYPE: PRT
<213> ORGANISM: Artificial Sequence
<220> FEATURE:
<223> OTHER INFORMATION: synthetic antibody PR000627 anti-CD3E SP34
    hum-scFv(VL7461_GS_VH3731)-hFc(C220S,LALA)

<400> SEQUENCE: 78

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Asp Lys Ala Ala Leu Thr Leu Leu Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gln Ser Gly Gln Gly Gly Ser Gly Gly Gly Ser Glu Val Gln Leu
            115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Thr Tyr Ala Met Asn Trp
145                 150                 155                 160

Val Arg Gln Ala Ser Gly Lys Gly Leu Glu Trp Val Gly Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Ser Thr Leu Tyr Leu Gln
            195                 200                 205

Met Asn Ser Leu Lys Thr Glu Asp Thr Ala Val Tyr Tyr Cys Val Arg
    210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser Ala Ser Glu Pro Lys Ser Ser
                245                 250                 255

Asp Lys Thr His Thr Cys Pro Pro Cys Pro Ala Pro Glu Ala Ala Gly
            260                 265                 270

Gly Pro Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
```

```
                355                 360                 365
Glu Lys Thr Ile Ser Lys Ala Lys Gly Gln Pro Arg Glu Pro Gln Val
    370                 375                 380

Tyr Thr Leu Pro Pro Ser Arg Glu Glu Met Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys
```

```
<210> SEQ ID NO 79
<211> LENGTH: 483
<212> TYPE: PRT
<213> ORGANISM: Artificial Sequence
<220> FEATURE:
<223> OTHER INFORMATION: synthetic antibody PR000914 anti-CD3E SP34
      hum-scFv(VH3231_GS_VL7461)-hFc(C220S,LALA)

<400> SEQUENCE: 79
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Gly Gly Gly
            115                 120                 125

Gln Ser Gly Gln Gly Gly Ser Gly Gly Gly Gly Ser Gln Ala Val Val
    130                 135                 140

Thr Gln Glu Pro Ser Leu Thr Val Ser Pro Gly Gly Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Gln Lys Pro Gly Gln Ala Pro Arg Gly Leu Ile Gly Gly
            180                 185                 190

Thr Asn Lys Arg Ala Pro Trp Thr Pro Ala Arg Phe Ser Gly Ser Leu
            195                 200                 205

Leu Gly Asp Lys Ala Ala Leu Thr Leu Leu Gly Ala Gln Pro Glu Asp
    210                 215                 220

Glu Ala Glu Tyr Phe Cys Ala Leu Trp Tyr Ser Asn Leu Trp Val Phe
```

-continued

```
225                 230                 235                 240

Gly Gly Gly Thr Lys Leu Thr Val Leu Ala Ser Glu Pro Lys Ser Ser
                245                 250                 255

Asp Lys Thr His Thr Cys Pro Pro Cys Pro Ala Pro Glu Ala Ala Gly
            260                 265                 270

Gly Pro Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Glu Tyr Lys Cys Lys Val Ser Asn Lys Ala Leu Pro Ala Pro Ile
            355                 360                 365

Glu Lys Thr Ile Ser Lys Ala Lys Gly Gln Pro Arg Glu Pro Gln Val
    370                 375                 380

Tyr Thr Leu Pro Pro Ser Arg Glu Glu Met Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys
```

```
<210> SEQ ID NO 80
<211> LENGTH: 483
<212> TYPE: PRT
<213> ORGANISM: Artificial Sequence
<220> FEATURE:
<223> OTHER INFORMATION: synthetic antibody PR000915 anti-CD3E SP34
      hum-scFv(VL7461_GS_VH3231)-hFc(C220S,LALA)

<400> SEQUENCE: 80
```

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
    50                  55                  60

Ser Gly Ser Leu Leu Gly Asp Lys Ala Ala Leu Thr Leu Leu Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gly Gly
```

-continued

```
              100             105             110
Gln Ser Gly Gln Gly Gly Ser Gly Gly Gly Gly Ser Glu Val Gln Leu
            115             120             125

Leu Glu Ser Gly Gly Gly Leu Val Gln Pro Gly Gly Ser Leu Arg Leu
    130             135             140

Ser Cys Ala Ala Ser Gly Phe Thr Phe Asn Thr Tyr Ala Met Asn Trp
145             150             155             160

Val Arg Gln Ala Pro Gly Lys Gly Leu Glu Trp Val Ser Arg Ile Arg
            165             170             175

Ser Lys Tyr Asn Asn Tyr Ala Thr Tyr Tyr Ala Asp Ser Val Lys Asp
            180             185             190

Arg Phe Thr Ile Ser Arg Asp Asp Ser Lys Ser Thr Leu Tyr Leu Gln
            195             200             205

Met Asn Ser Leu Arg Ala Glu Asp Thr Ala Val Tyr Tyr Cys Val Arg
    210             215             220

His Gly Asn Phe Gly Asn Ser Tyr Val Ser Trp Phe Ala Tyr Trp Gly
225             230             235             240

Gln Gly Thr Leu Val Thr Val Ser Ser Ala Ser Glu Pro Lys Ser Ser
            245             250             255

Asp Lys Thr His Thr Cys Pro Pro Cys Pro Ala Pro Glu Ala Ala Gly
            260             265             270

Gly Pro Ser Val Phe Leu Phe Pro Pro Lys Pro Lys Asp Thr Leu Met
            275             280             285

Ile Ser Arg Thr Pro Glu Val Thr Cys Val Val Val Asp Val Ser His
    290             295             300

Glu Asp Pro Glu Val Lys Phe Asn Trp Tyr Val Asp Gly Val Glu Val
305             310             315             320

His Asn Ala Lys Thr Lys Pro Arg Glu Glu Gln Tyr Asn Ser Thr Tyr
            325             330             335

Arg Val Val Ser Val Leu Thr Val Leu His Gln Asp Trp Leu Asn Gly
            340             345             350

Lys Glu Tyr Lys Cys Lys Val Ser Asn Lys Ala Leu Pro Ala Pro Ile
            355             360             365

Glu Lys Thr Ile Ser Lys Ala Lys Gly Gln Pro Arg Glu Pro Gln Val
    370             375             380

Tyr Thr Leu Pro Pro Ser Arg Glu Glu Met Thr Lys Asn Gln Val Ser
385             390             395             400

Leu Thr Cys Leu Val Lys Gly Phe Tyr Pro Ser Asp Ile Ala Val Glu
            405             410             415

Trp Glu Ser Asn Gly Gln Pro Glu Asn Asn Tyr Lys Thr Thr Pro Pro
            420             425             430

Val Leu Asp Ser Asp Gly Ser Phe Phe Leu Tyr Ser Lys Leu Thr Val
            435             440             445

Asp Lys Ser Arg Trp Gln Gln Gly Asn Val Phe Ser Cys Ser Val Met
    450             455             460

His Glu Ala Leu His Asn His Tyr Thr Gln Lys Ser Leu Ser Leu Ser
465             470             475             480

Pro Gly Lys
```

```
<210> SEQ ID NO 81
<211> LENGTH: 483
<212> TYPE: PRT
<213> ORGANISM: Artificial Sequence
<220> FEATURE:
```

-continued

<223> OTHER INFORMATION: synthetic antibody PR001850 anti-CD3 SP34
      hum-scFv(VL7461-GS-VH3732)-hFc(AAG)

<400> SEQUENCE: 81

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Asp Lys Ala Ala Leu Thr Leu Leu Gly Ala
65                  70                  75                  80

Gln Pro Glu Asp Glu Ala Glu Tyr Phe Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gln Ser Gly Gln Gly Gly Ser Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Ser Thr Tyr Ala Met Asn Trp
145                 150                 155                 160

Val Arg Gln Ala Ser Gly Lys Gly Leu Glu Trp Val Gly Arg Ile Arg
                165                 170                 175

Ser Lys Tyr Asn Asn Tyr Ala Thr Tyr Tyr Ala Asp Ser Val Lys Asp
                180                 185                 190

Arg Phe Thr Ile Ser Arg Asp Asp Ser Lys Ser Thr Leu Tyr Leu Gln
            195                 200                 205

Met Asn Ser Leu Lys Thr Glu Asp Thr Ala Val Tyr Tyr Cys Val Arg
    210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser Ala Ser Glu Pro Lys Ser Ser
            245                 250                 255

Asp Lys Thr His Thr Cys Pro Pro Cys Pro Ala Pro Glu Ala Ala Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Gly Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Glu Glu Met Thr Lys Asn Gln Val Ser
385                 390                 395                 400
```

-continued

```
Leu Thr Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys

<210> SEQ ID NO 82
<211> LENGTH: 451
<212> TYPE: PRT
<213> ORGANISM: Artificial Sequence
<220> FEATURE:
<223> OTHER INFORMATION: synthetic antibody PR000014 B7H4 heavychain

<400> SEQUENCE: 82

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
            35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
            85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270
```

-continued

```
Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
        450

<210> SEQ ID NO 83
<211> LENGTH: 214
<212> TYPE: PRT
<213> ORGANISM: Artificial Sequence
<220> FEATURE:
<223> OTHER INFORMATION: synthetic antibody PR000014 B7H4 lightchain;
        PR002883 B7H4 lightchain

<400> SEQUENCE: 83

Asp Ile Gln Met Thr Gln Ser Pro Ser Ser Leu Ser Ala Ser Val Gly
1                5                   10                  15

Asp Arg Val Thr Ile Thr Cys Lys Ala Ser Gln Gly Phe Asn Lys Tyr
                20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asp Leu Leu Tyr
                85                  90                  95

Ala Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 449
<212> TYPE: PRT
<213> ORGANISM: Artificial Sequence
<220> FEATURE:
<223> OTHER INFORMATION: synthetic antibody PR000374 ROR1 heavychain

<400> SEQUENCE: 84

Glu Val Gln Leu Val Glu Ser Gly Gly Gly Leu Val Gln Pro Gly Arg
1               5                   10                  15

Ser Leu Arg Leu Ser Cys Thr Ala Ser Gly Ser Asp Ile Asn Asp Tyr
            20                  25                  30

Pro Ile Thr Trp Val Arg Gln Ala Pro Gly Gln Gly Leu Glu Trp Ile
        35                  40                  45

Gly Phe Ile Asn Ser Gly Gly Ser Thr Trp Tyr Ala Ser Trp Val Lys
    50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Glu Asp Thr Ala Val Tyr Tyr Cys Ala
            85                  90                  95

Arg Gly Tyr Ser Thr Tyr Tyr Arg Asp Phe Asn Ile Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

-continued

```
Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 85
<211> LENGTH: 217
<212> TYPE: PRT
<213> ORGANISM: Artificial Sequence
<220> FEATURE:
<223> OTHER INFORMATION: synthetic antibody PR000374 ROR1 lightchain;
      PR002885 ROR1 lightchain

<400> SEQUENCE: 85
```

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Gln Pro Pro Lys Leu Leu Ile
        35                  40                  45

Tyr Arg Ala Ser Asn Leu Ala Ser Gly Val Pro Asp Arg Phe Ser Gly
    50                  55                  60

Ser Gly Ser Gly Thr Asp Phe Thr Leu Thr Ile Ser Ser Leu Glu Ala
65                  70                  75                  80

Glu Asp Val Ala Thr Tyr Tyr Cys Leu Gly Gly Val Gly Ala Val Ser
            85                  90                  95

Tyr Arg Thr Ser Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

-continued

<210> SEQ ID NO 86
<211> LENGTH: 451
<212> TYPE: PRT
<213> ORGANISM: Artificial Sequence
<220> FEATURE:
<223> OTHER INFORMATION: synthetic antibody PR002883 B7H4
      Hole-heavychain

<400> SEQUENCE: 86

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val Ser

-continued

```
              355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 87
<211> LENGTH: 449
<212> TYPE: PRT
<213> ORGANISM: Artificial Sequence
<220> FEATURE:
<223> OTHER INFORMATION: synthetic antibody PR002885 ROR1
      Hole-heavychain

<400> SEQUENCE: 87

Glu Val Gln Leu Val Glu Ser Gly Gly Gly Leu Val Gln Pro Gly Arg
1               5                   10                  15

Ser Leu Arg Leu Ser Cys Thr Ala Ser Gly Ser Asp Ile Asn Asp Tyr
                20                  25                  30

Pro Ile Thr Trp Val Arg Gln Ala Pro Gly Gln Gly Leu Glu Trp Ile
            35                  40                  45

Gly Phe Ile Asn Ser Gly Gly Ser Thr Trp Tyr Ala Ser Trp Val Lys
    50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Glu Asp Thr Ala Val Tyr Tyr Cys Ala
                85                  90                  95

Arg Gly Tyr Ser Thr Tyr Tyr Arg Asp Phe Asn Ile Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
        260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
        290             295             300

Val Ser Val Leu Thr Val Leu His Gln Asp Trp Leu Asn Gly Lys Glu
305             310             315             320

Tyr Lys Cys Lys Val Ser Asn Lys Ala Leu Gly Ala Pro Ile Glu Lys
            325             330             335

Thr Ile Ser Lys Ala Lys Gly Gln Pro Arg Glu Pro Gln Val Cys Thr
        340             345             350

Leu Pro Pro Ser Arg Glu Glu Met Thr Lys Asn Gln Val Ser Leu Ser
        355             360             365

Cys Ala Val Lys Gly Phe Tyr Pro Ser Asp Ile Ala Val Glu Trp Glu
        370             375             380

Ser Asn Gly Gln Pro Glu Asn Asn Tyr Lys Thr Thr Pro Pro Val Leu
385             390             395             400

Asp Ser Asp Gly Ser Phe Phe Leu Val Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys
```

<210> SEQ ID NO 88
<211> LENGTH: 483
<212> TYPE: PRT
<213> ORGANISM: Artificial Sequence
<220> FEATURE:
<223> OTHER INFORMATION: synthetic antibody PR002883 chain-2;synthetic
      antibody PR002885 chain-2; (synthetic antibody PR000627 in
      knob-Fc)

<400> SEQUENCE: 88

```
Gln Ala Val Val Thr Gln Glu Pro Ser Leu Thr Val Ser Pro Gly Gly
1               5               10              15

Thr Val Thr Leu Thr Cys Arg Ser Ser Thr Gly Ala Val Thr Thr Ser
        20              25              30

Asn Tyr Ala Asn Trp Val Gln Gln Lys Pro Gly Gln Ala Pro Arg Gly
        35              40              45

Leu Ile Gly Gly Thr Asn Lys Arg Ala Pro Trp Thr Pro Ala Arg Phe
    50              55              60

Ser Gly Ser Leu Leu Gly Asp Lys Ala Ala Leu Thr Leu Leu Gly Ala
65              70              75              80

Gln Pro Glu Asp Glu Ala Glu Tyr Phe Cys Ala Leu Trp Tyr Ser Asn
            85              90              95

Leu Trp Val Phe Gly Gly Gly Thr Lys Leu Thr Val Leu Gly Gly Gly
            100             105             110

Gln Ser Gly Gln Gly Gly Ser Gly Gly Gly Ser Glu Val Gln Leu
        115             120             125

Val Glu Ser Gly Gly Gly Leu Val Gln Pro Gly Gly Ser Leu Lys Leu
    130             135             140

Ser Cys Ala Ala Ser Gly Phe Thr Phe Asn Thr Tyr Ala Met Asn Trp
145             150             155             160
```

-continued

```
Val Arg Gln Ala Ser Gly Lys Gly Leu Glu Trp Val Gly Arg Ile Arg
            165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Ser Thr Leu Tyr Leu Gln
            195                 200                 205

Met Asn Ser Leu Lys Thr Glu Asp Thr Ala Val Tyr Tyr Cys Val Arg
            210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser Ala Ser Glu Pro Lys Ser Ser
            245                 250                 255

Asp Lys Thr His Thr Cys Pro Pro Cys Pro Ala Pro Glu Ala Ala Gly
            260                 265                 270

Gly Pro Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
            290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
            325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Gly Ala Pro Ile
            355                 360                 365

Glu Lys Thr Ile Ser Lys Ala Lys Gly Gln Pro Arg Glu Pro Gln Val
            370                 375                 380

Tyr Thr Leu Pro Pro Cys Arg Glu Glu Met Thr Lys Asn Gln Val Ser
385                 390                 395                 400

Leu Trp Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
            450                 455                 460

His Glu Ala Leu His Asn His Tyr Thr Gln Lys Ser Leu Ser Leu Ser
465                 470                 475                 480

Pro Gly Lys
```

```
<210> SEQ ID NO 89
<211> LENGTH: 117
<212> TYPE: PRT
<213> ORGANISM: Artificial Sequence
<220> FEATURE:
<223> OTHER INFORMATION: IGHV3-73*01|GHJ1*01

<400> SEQUENCE: 89

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30
```

```
Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Ala Glu Tyr Phe Gln His Trp Gly Gln Gly Thr Leu
            100                 105                 110

Val Thr Val Ser Ser
        115

<210> SEQ ID NO 90
<211> LENGTH: 115
<212> TYPE: PRT
<213> ORGANISM: Artificial Sequence
<220> FEATURE:
<223> OTHER INFORMATION: IGHV3-23*01|IGHJ1*01

<400> SEQUENCE: 90

Glu Val Gln Leu Leu Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Glu Tyr Phe Gln His Trp Gly Gln Gly Thr Leu Val Thr
            100                 105                 110

Val Ser Ser
        115

<210> SEQ ID NO 91
<211> LENGTH: 110
<212> TYPE: PRT
<213> ORGANISM: Artificial Sequence
<220> FEATURE:
<223> OTHER INFORMATION: IGLV7-46*02|IGLJ2*01

<400> SEQUENCE: 91

Gln Ala Val Val Thr Gln Glu Pro Ser Leu Thr Val Ser Pro Gly Gly
1                   5                   10                  15

Thr Val Thr Leu Thr Cys Gly Ser Ser Thr Gly Ala Val Thr Ser Gly
                20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Leu Leu Ser Tyr Ser Gly
                85                  90                  95
```

-continued

```
Ala Arg Val Val Phe Gly Gly Gly Thr Lys Leu Thr Val Leu
            100                 105                 110

<210> SEQ ID NO 92
<211> LENGTH: 107
<212> TYPE: PRT
<213> ORGANISM: Artificial Sequence
<220> FEATURE:
<223> OTHER INFORMATION: IGKV1-39*01|IGKJ4*01

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```